(12) United States Patent
Kong et al.

(10) Patent No.: US 11,674,182 B2
(45) Date of Patent: Jun. 13, 2023

(54) BIOMARKER FOR HER2-POSITIVE CANCER AND ANTI-HER2 THERAPY AND APPLICATIONS THEREOF

(71) Applicant: INDUSTRY-UNIVERSITY COOPERATION FOUNDATION HANYANG UNIVERSITY, Seoul (KR)

(72) Inventors: Gu Kong, Seoul (KR); Jeong-Yeon Lee, Seoul (KR); Hyeong-Seok Joo, Seoul (KR)

(73) Assignee: INDUSTRY-UNIVERSITY COOPERATION FOUNDATION HANYANG UNIVERSITY, Seoul (KR)

( * ) Notice: Subject to any disclaimer, the term of this patent is extended or adjusted under 35 U.S.C. 154(b) by 544 days.

(21) Appl. No.: 16/491,993

(22) PCT Filed: Mar. 8, 2018

(86) PCT No.: PCT/KR2018/002791
§ 371 (c)(1),
(2) Date: Sep. 6, 2019

(87) PCT Pub. No.: WO2018/164518
PCT Pub. Date: Sep. 13, 2018

(65) Prior Publication Data
US 2021/0010084 A1 Jan. 14, 2021

(30) Foreign Application Priority Data

Mar. 8, 2017 (KR) .................... 10-2017-0029627
Mar. 31, 2017 (KR) .................... 10-2017-0042224

(51) Int. Cl.
| | | |
|---|---|---|
| *C12Q 1/6886* | (2018.01) | |
| *A61K 39/00* | (2006.01) | |
| *A61K 31/18* | (2006.01) | |
| *A61K 31/216* | (2006.01) | |
| *A61K 31/426* | (2006.01) | |
| *A61K 31/438* | (2006.01) | |
| *A61K 31/4406* | (2006.01) | |
| *A61K 31/444* | (2006.01) | |
| *A61K 31/496* | (2006.01) | |
| *C07K 16/32* | (2006.01) | |
| *G01N 33/574* | (2006.01) | |

(52) U.S. Cl.
CPC ............ *C12Q 1/6886* (2013.01); *A61K 31/18* (2013.01); *A61K 31/216* (2013.01); *A61K 31/426* (2013.01); *A61K 31/438* (2013.01); *A61K 31/444* (2013.01); *A61K 31/4406* (2013.01); *A61K 31/496* (2013.01); *A61K 39/001106* (2018.08); *C07K 16/32* (2013.01); *G01N 33/5748* (2013.01); *C12Q 2600/106* (2013.01); *C12Q 2600/158* (2013.01)

(58) Field of Classification Search
CPC ...................................................... C12Q 1/6886
USPC ........................................................ 424/133.1
See application file for complete search history.

(56) References Cited

U.S. PATENT DOCUMENTS

2013/0178381 A1* 7/2013 Krijgsman ........... C12Q 1/6886
506/9
2016/0045596 A1  2/2016 Geretti et al.

FOREIGN PATENT DOCUMENTS

| KR | 10-2015-0024342 A | 3/2015 |
|---|---|---|
| KR | 10-20160110104 A | 9/2016 |
| KR | 10-2017-0002364 A | 1/2017 |
| WO | 2004089294 A2 | 10/2004 |
| WO | 2004089294 A3 | 10/2004 |
| WO | 2008028926 A2 | 3/2008 |
| WO | 2008028926 A3 | 3/2008 |
| WO | 2014/001232 A1 | 1/2014 |

OTHER PUBLICATIONS

Friedman et al (Cancer Research, 2009, 69(24_Supplement): 5056).*
Schulte et al (Cell Death and Differentiation, 2007, 14: 1040-1049).*
Sircoulomb et al (BMC Cancer, 2010, 10(539): 1-18).*
Riis et al (BMC Cancer, 2010, 10(686): 1-11).*
Michael J. Duffy et al., "ADAM10 and ADAM17: New Players in Trastuzumab Resistance", Oncotarget, Nov. 30, 2014, pp. 10963-10964, vol. 5, No. 22.
Katharina Feldinger et al., "ADAM 10 mediates trastuzumab resistance and is correlated with survival in HER2 positive breast cancer", Oncotarget, May 8, 2014, pp. 6633-6634, vol. 5, No. 16.
Hyeong-Seok Joo, "A study on MEL-18 Amplification in HER2-positive Breast Cancer", Master's thesis, Graduate School of Hanyang University, Department of Personalized Genome Mediicine, Jan. 1, 2018, pp. 1-44.
Jeong-Yeon Lee et al., "MEL-18, a tumor suppressor for aggressive breast cancer", Oncotarget, Jun. 22, 2015, pp. 15710-15711, vol. 6, No. 18.

(Continued)

*Primary Examiner* — Sean E Aeder
(74) *Attorney, Agent, or Firm* — Sughrue Mion, PLLC

(57) ABSTRACT

The present invention provides MEL-18, which is a biomarker for human epidermal growth factor receptor2 (HER2)-positive cancer and anti-HER2 therapy, and a use thereof. According to the present invention, MEL-18 is a prognostic factor or predictor for a response of subjects to an anti-HER2-targeted drug in HER2-POSITIVE cancer and may be used in companion diagnostics for HER2-targeted drugs in subjects with HER2-positive cancer. Therefore, HER2-positive cancer may be more effectively treated by overcoming resistance to HER2 therapeutic agents and enhancing therapeutic efficacy by determining whether ADAM10/17 inhibitors are administered or co-administered with HER2-targeted drugs.

15 Claims, 29 Drawing Sheets
Specification includes a Sequence Listing.

(56) References Cited

OTHER PUBLICATIONS

Korean Office Action for 10-2018-0027663 dated Aug. 8, 2018.
International Search Report for PCT/JP2018/002791 dated, Jun. 7, 2018 (PCT/ISA/210).
Martin Sauvageau, et al., "Polycomb group proteins: multi-faceted regulators of somatic stem cells and cancer", Cell Stem Cell, Sep. 3, 2010, No. 7, pp. 299-313 (15 pages total).
Hengbin Wang, et al., "Role of histone H2A ubiquitination in Polycomb silencing", Nature, Oct. 14, 2004, vol. 431, pp. 873-878 (6 pages total).
Ru Cao, et al., "Role of histone H3 lysine 27 methylation in Polycomb-group silencing", Science, Nov. 1, 2002, vol. 298, pp. 1039-1043 (6 pages total).
Jeong-Yeon Lee, et al., "MEL-18, a tumor suppressor for aggressive breast cancer", Oncotarget, Impact Journal, 2015, pp. 1-2 (2 pages total).
Wei-Jian Guo, et al., "Mel-18 acts as a tumor suppressor by repressing Bmi-1 expression and down-regulating Akt activity in breast cancer cells", Cancer Res, Jun. 1, 2007, vol. 67, No. 11, pp. 5083-5089 (7 pages total).
Lluis Morey, et al., "Polycomb Regulates Mesoderm Cell Fate-Specification in Embryonic Stem Cells through Activation and Repression Mechanisms", Cell Stem Cell, Sep. 3, 2015, vol. 17 pp. 300-315 (17 pages total).
Margit LH Riis, et al., "Expression of BMI-1 and Mel-18 in breast tissue—a diagnostic marker in patients with breast cancer", BMC Cancer, 2010, vol. 10, No. 686, pp. 1-11 (11 pages total).
W. Wang, et al., "The novel tumor-suppressor Mel-18 in prostate cancer: its functional polymorphism, expression and clinical significance", International Journal of Cancer, 2009, vol. 125, pp. 2836-2843 (8 pages total).
Xiao-Wei Zhang, et al., "BMI1 and Mel-18 oppositely regulate carcinogenesis and progression of gastric cancer", Molecular Cancer, 2010, vol. 9, No. 40, pp. 2-12 (12 pages total).
B.-H. Guo, et al., "Low expression of Mel-18 predicts poor prognosis in patients with breast cancer", Annals of Oncology, Dec. 2010, vol. 21, No. 12, pp. 2361-2369 (9 pages total).
Jeong-Yeon Lee, et al., "Mel-18 negatively regulates INK4a/ARF-independent cell cycle progression via Akt inactivation in breast cancer", Cancer Res, Jun. 1, 2008, vol. 68, No. 11, pp. 4201-4209 (9 pages total).
J-H Park, et al., "Loss of Mel-18 induces tumor angiogenesis through enhancing the activity and expression of HIF-1α mediated by the PTEN/PI3K/Akt pathway", Oncogene, 2011, vol. 30, pp. 4578-4589 (12 pages total).
Hee-Young Won, et al., "Loss of Mel-18 enhances breast cancer stem cell activity and tumorigenicity through activating Notch signaling mediated by the Wnt/TCF pathway", The FASEB Journal, Dec. 2012, vol. 26, pp. 5002-5013 (12 pages total).
J-Y Lee, et al., "Loss of the polycomb protein Mel-18 enhances the epithelial-mesenchymal transition by ZEB1 and ZEB2 expression through the downregulation of miR-205 in breast cancer", Oncogene, 2013, pp. 1-11 (11 pages total).
Jeong-Yeon Lee, et al., "MEL-18, loss mediates estrogen receptor-α downregulation and hormone independence", The Journal of Clinical Investigation, May 2015, vol. 125, No. 5, pp. 1801-1814 (14 pages total).
Dennis J. Slamon, et al., "Human breast cancer: correlation of relapse and survival with amplification of the HER-2/neu oncogene", Science, Jan. 9, 1987, vol. 235, pp. 177-182 (7 pages total).
Yosef Yarden, et al., "The ERBB network: at last, cancer therapy meets systems biology", Nature Review, Cancer, Aug. 2012, vol. 12, pp. 553-563 (11 pages total).
Mothaffar F. Rimawi, et al., "Targeting HER2 for the treatment of breast cancer", Annual Review Medicine, 2015, vol. 66, pp. 111-128 (21 pages total).
A. Pandiella, et al., "Activation of an EGFR/neu chimeric receptor: early intracellular signals and cell proliferation responses", Oncogene, Nov. 1, 1989, vol. 4, No. 11, Abstract.

Kathryn S.R. Spencer, et al., "ErbB2 is necessary for induction of carcinoma cell invasion by ErbB family receptor tyrosine kinases", The Journal of Cell Biology, Jan. 24, 2000, vol. 148, No. 2, pp. 385-397 (13 pages total).
H. Korkaya, et al., "HER2 regulates the mammary stem/progenitor cell population driving tumorigenesis and invasion", Oncogene, 2008, vol. 27, pp. 6120-6130 (11 pages total).
Dennis J. Slamon, et al., "Use of chemotherapy plus a monoclonal antibody against HER2 for metastatic breast cancer that overexpresses HER2", The New England Journal of Medicine, Mar. 15, 2001, vol. 344, No. 11, pp. 783-792 (10 pages total).
Charles L. Vogel, et al., "Efficacy and safety of trastuzumab as a single agent in first-line treatment of HER2-overexpressing metastatic breast cancer", Journal of Clinical Oncology, Feb. 1, 2002, vol. 20, No. 3, pp. 719-726 (8 pages total).
Keng-Hsueh Lan, et al., "Mechanisms of trastuzumab resistance and their clinical implications", Annual New York Academy of Sciences, 2005, vol. 1059, 70-75 (6 pages total).
Andrew D. Seidman, et al., "Randomized phase III trial of weekly compared with every-3-weeks paclitaxel for metastatic breast cancer, with trastuzumab for all HER-2 overexpressors and random assignment to trastuzumab or not in HER-2 nonoverexpressors: final results of Cancer and Leukemia Group B protocol 9840", Journal of Clinical Oncology, Apr. 1, 2008, vol. 26, No. 10, pp. 1642-1649 (8 pages total).
Neil L. Spector, et al., "Understanding the mechanisms behind trastuzumab therapy for human epidermal growth factor receptor 2-positive breast cancer", Journal of Clinical Oncology, Dec. 1, 2009, vol. 27, No. 34, pp. 5838-5847 (10 pages total).
Judit Anido, et al., "Biosynthesis of tumorigenic HER2 C-terminal fragments by alternative initiation of translation", The EMBO Journal, 2006, vol. 25, No. 13, pp. 3234-3244 (11 pages total).
Peter Nagy, et al., "Decreased accessibility and lack of activation of ErbB2 in JIMT-1, a herceptin-resistant, MUC4-expressing breast cancer cell line", American Association for Cancer Research, Jan. 15, 2005, vol. 65, No. 2, pp. 473-482 (11 pages total).
Christoph A. Ritter, et al., "Human breast cancer cells selected for resistance to trastuzumab in vivo overexpress epidermal growth factor receptor and ErbB ligands and remain dependent on the ErbB receptor network", American Association for Clinical Cancer Research, Aug. 15, 2007, vol. 13, No. 16, pp. 4909-4919 (12 pages total).
Michael J. Duffy, et al., "ADAM10 and ADAM17: New players in trastuzumab resistance", Impact Journals, Oncotarget, 2014, vol. 5, No. 22, pp. 10963-10964 (2 pages total).
Andrea B. Motoyama, et al., "The efficacy of ErbB receptor-targeted anticancer therapeutics is influenced by the availability of epidermal growth factor-related peptides", Cancer Research, Jun. 1, 2002, vol. 62, pp. 3151-3158 (8 pages total).
Yoichi Nagata, et al., "PTEN activation contributes to tumor inhibition by trastuzumab, and loss of PTEN predicts trastuzumab resistance in patients", Cancer Cell, Aug. 2004, vol. 6, pp. 117-127 (11 pages total).
Yuhong Lu, et al., "Insulin-like growth factor-I receptor signaling and resistance to trastuzumab (Herceptin)", Journal of the National Cancer Institute, Dec. 19, 2001, vol. 93, No. 24, pp. 1852-1857 (6 pages total).
José Baselga, et al., "Novel anticancer targets: revisiting ERBB2 and discovering ERBB3", Nature Review, Cancer, Jul. 2009, vol. 9, pp. 463-475 (13 pages total).
H. J. Burstein, et al., "A phase II study of lapatinib monotherapy in chemotherapy-refractory HER2-positive and HER2-negative advanced or metastatic breast cancer", Annals of Oncology, Jun. 2008, vol. 19, No. 6, pp. 1068-1074 (7 pages total).
José Baselga, M.D., Ph.D., et al., "Pertuzumab plus trastuzumab plus docetaxel for metastatic breast cancer", The New England Journal of Medicine, Jan. 12, 2012, vol. 366, No. 2, pp. 109-119 (11 pages total).
The Cancer Genome Atlas Network, "Comprehensive molecular portraits of human breast tumours", Nature, Oct. 4, 2012, vol. 490, pp. 61-70 (10 pages total).
Christina Curtis, et al., "The genomic and transcriptomic architecture of 2,000 breast tumours reveals novel subgroups", Nature, Jun. 21, 2012, vol. 486, pp. 346-352 (7 pages total).

(56) References Cited

OTHER PUBLICATIONS

Merel Gijsen, et al., "HER2 phosphorylation is maintained by a PKB negative feedback loop in response to anti-HER2 herceptin in breast cancer", PLoS Biology, Dec. 2010, vol. 8, No. 12, pp. 1-16 (16 pages total).
Eva A. Ebbing, et al., "ADAM10-mediated release of heregulin confers resistance to trastuzumab by activating HER3", Oncotarget, 2016, vol. 7, pp. 1-12 (12 pages total).
Katharina Feldinger, et al., "ADAM10 mediates trastuzumab resistance and is correlated with survival in HER2 positive breast cancer", Oncotarget, 2014, vol. 5, No. 16, pp. 6633-6646 (14 pages total).
Lígia Tavares, et al., "RYBP-PRC1 complexes mediate H2A ubiquitylation at polycomb target sites independently of PRC2 and H3K27me3", Cell, Feb. 17, 2012, vol. 148, pp. 664-678 (15 pages total).
Julien Vandamme, et al., "Interaction proteomics analysis of polycomb proteins defines distinct PRC1 complexes in mammalian cells", ASBMB, Molecular & Cellular Proteomics, vol. 10, No. 4 (23 pages total).
Pierre-Jean Lamy, et al., "Quantification and clinical relevance of gene amplification at chromosome 17q12-q21 in human epidermal growth factor receptor 2-amplified breast cancers", Breast Cancer Research, 2011, vol. 13, No. R15 (12 pages total).
Max S. Mano, et al., "The 17q12-q21 amplicon: Her2 and topoisomerase-IIα and their importance to the biology of solid tumours", Science Direct, Cancer Treatment Reviews, 2007, vol. 33, pp. 64-77 (14 pages total).
Rastislav Tamaskovic, et al., "Intermolecular biparatopic trapping of ErbB2 prevents compensatory activation of PI3K/AKT via RAS-p110 crosstalk", Nature Communication, Jun. 3, 2016, vol. 7, No. 11672, pp. 1-18 (18 pages total).
Jessica L. Christenson, et al.,"t-Darpp overexpression in HER2-positive breast cancer confers a survival advantage in lapatinib", Oncotarget, Sep. 28, 2015, vol. 6, No. 32, pp. 33134-33145 (12 pages total).
Sophie Hamel, et al., "Both t-Darpp and Darpp-32 can cause resistance to trastuzumab in breast cancer cells and are frequently expressed in primary breast cancers", Breast Cancer Res Treat, 2010, vol. 120, pp. 47-57 (11 pages total).
Jiajun Cui, et al., "Cross-talk between HER2 and MED1 regulates tamoxifen resistance of human breast cancer cells", American Association for Cancer Research, Nov. 1, 2012, vol. 72, No. 21, pp. 5625-5634 (11 pages total).
J. Malapeira, et al., "ADAM17 (TACE) regulates TGFβ signaling through the cleavage of vasorin", Oncogene, 2011, vol. 30, pp. 1912-1922 (11 pages total).
Maeve Mullooly, et al., "ADAM10: a new player in breast cancer progression?", British Journal of Cancer, 2015, vol. 113, pp. 945-951 (7 pages total).
Patricia M. McGowan, et al., "ADAM-17 expression in breast cancer correlates with variables of tumor progression", Clin Cancer Res, Apr. 15, 2007, vol. 13, No. 8, pp. 2335-2343 (9 pages total).
Gillian Murphy, "The ADAMs: signalling scissors in the tumor microenvironment", Nature Reviews, Cancer, Dec. 2008, vol. 8, pp. 929-941 (13 pages total).

Xiangdong Liu, et al., "Selective inhibition of ADAM metalloproteases blocks HER-2 extracellular domain (ECD) cleavage and potentiates the anti-tumor effects of trastuzumab", Cancer Biology & Therapy, Jun. 2006, vol. 5, No. 6, pp. 648-656 (10 pages total).
Lois Witters, et al., "Synergistic inhibition with a dual epidermal growth factor receptor/HER-2/neu tyrosine kinase inhibitor and a disintegrin and metalloprotease inhibitor", American Association for Cancer Research, Sep. 1, 2008, vol. 68, No. 17, pp. 7083-7089 (8 pages total).
Timothy A. Yap, et al., "First-in-man clinical trial of the oral pan-AKT inhibitor MK-2206 in patients with advanced solid tumors", Journal of Clinical Oncology, Dec. 10, 2011, vol. 29, No. 35, pp. 4688-4695 (8 pages total).
Masamoto Kanno, et al., "mel-18, a Polycomb group-related mammalian gene, encodes a transcriptional negative regulator with tumor suppressive activity", The EMBO Journal, 1995, vol. 14, No. 22, pp. 5672-5678 (7 pages total).
Ru Cao, et al., "Role of Bmi-1 and Ring1A in H2A ubiquitylation and Hox gene silencing", Molecular Cell, Dec. 22, 2005, vol. 20, pp. 845-854 (10 pages total).
Sarah Elderkin, et al., "A phosphorylated form of Mel-18 targets the Ring1B histone H2A ubiquitin ligase to chromatin", Molecular Cell, Oct. 12, 2007, vol. 28, pp. 107-120 (14 pages total).
Min-Hyung Cho, et al., "DOT1L cooperates with the c-Myc-p300 complex to epigenetically derepress CDH1 transcription factors in breast cancer progression", Nature Communications. Jul. 22, 2015, vol. 6, No. 7821, pp. 1-14 (14 pages total).
Da Wei Huang, et al., "Systematic and integrative analysis of large gene lists using DAVID bioinformatics resources", Nature Protocols, 2009, vol. 4, No. 1, pp. 44-57 (14 pages total).
Da Wei Huang, et al., "Bioinformatics enrichment tools: paths toward the comprehensive functional analysis of large gene lists", Nucleic Acids Research, 2009, vol. 37, No. 1, pp. 1-13 (13 pages total).
Vamsi K Mootha, et al., "PGC-1α-responsive genes involved in oxidative phosphorylation are coordinately downregulated in human diabetes", Nature Genetics, Jul. 2003, vol. 34, No. 3, pp. 267-273 (7 pages total).
Aravind Subramanian, et al., "Gene set enrichment analysis: a knowledge-based approach for interpreting genome-wide expression profiles", PNAS, Oct. 25, 2005, vol. 102, No. 43, pp. 15545-15550 (6 pages total).
Ethan Cerami, et al., "The eBio cancer genomics portal: an open platform for exploring multidimensional cancer genomics data", Cancer Discov., May 2012, vol. 2, No. 5, pp. 401-404 (7 pages total).
Jianjiong Gao, et al., "Integrative analysis of complex cancer genomics and clinical profiles using the cBioPortal", Sci Signal., 2013, vol. 6, No. 269, pp. 1-34 (34 pages total).
Lorenzo Castagnoli, et al., "Activated d16HER2 homodimers and SRC kinase mediate optimal efficacy for trastuzumab", American Association for Cancer Research, Nov. 1, 2014, vol. 74, No. 21, pp. 6248-6659 (13 pages total).
Tiziana Triulzi, et al., "Whole-transcriptome analysis links trastuzumab sensitivity of breast tumors to both HER2 dependence and immune cell infiltration", Oncotarget, Jul. 1, 2015, vol. 6, No. 29, 28173-28182 (10 pages total).

\* cited by examiner

FIG. 8A

| NAME | SIZE | ES | NES | P-value |
|---|---|---|---|---|
| EPIDERMAL_GROWTH_FACTOR_RECEPTOR_SIGNALING_PATHWAY | 22 | 0.414 | 1.365 | 0.000 |
| GROWTH_FACTOR_ACTIVITY | 54 | 0.443 | 1.415 | 0.000 |
| POSITIVE_REGULATION_OF_CELL_PROLIFERATION | 147 | 0.288 | 1.281 | 0.000 |
| REGULATION_OF_G_PROTEIN_COUPLED_RECEPTOR_PROTEIN_SIGNALING_PATHWAY | 23 | 0.404 | 1.278 | 0.000 |
| POSITIVE_REGULATION_OF_TRANSCRIPTION | 139 | 0.327 | 1.418 | 0.000 |
| POSITIVE_REGULATION_OF_CELL_PROLIFERATION | 147 | 0.288 | 1.281 | 0.000 |
| POSITIVE_REGULATION_OF_CELL_CYCLE | 16 | 0.595 | 1.512 | 0.000 |
| PROTEIN_SERINE_THREONINE_PHOSPHATASE_ACTIVITY | 23 | 0.529 | 1.525 | 0.000 |
| TRANSMEMBRANE_RECEPTOR_PROTEIN_PHOSPHATASE_ACTIVITY | 19 | 0.516 | 1.517 | 0.000 |
| LIGAND_DEPENDENT_NUCLEAR_RECEPTOR_ACTIVITY | 25 | 0.458 | 1.412 | 0.000 |
| POSITIVE_REGULATION_OF_MAP_KINASE_ACTIVITY | 47 | 0.388 | 1.388 | 0.000 |
| DNA_HELICASE_ACTIVITY | 25 | 0.386 | 1.502 | 0.000 |
| CHROMOSOME_SEGREGATION | 31 | 0.442 | 1.482 | 0.000 |
| INDUCTION_OF_APOPTOSIS_BY_EXTRACELLULAR_SIGNALS | 27 | -0.581 | -1.535 | 0.000 |
| KINASE_INHIBITOR_ACTIVITY | 25 | -0.581 | -1.480 | 0.000 |
| PROTEIN_KINASE_INHIBITOR_ACTIVITY | 24 | -0.590 | -1.478 | 0.000 |

SEQUENCE LISTING

<160> NUMBER OF SEQ ID NOS: 29

<210> SEQ ID NO 1
<211> LENGTH: 25
<212> TYPE: DNA
<213> ORGANISM: Artificial Sequence
<220> FEATURE:
<223> OTHER INFORMATION: MEL-18 forward primer

<400> SEQUENCE: 1
gtacttcatc gacgccacca ctatc                                            25

<210> SEQ ID NO 2
<211> LENGTH: 23
<212> TYPE: DNA
<213> ORGANISM: Artificial Sequence
<220> FEATURE:
<223> OTHER INFORMATION: MEL-18 reverse primer

<400> SEQUENCE: 2
ctcgtcctcg tacagaacct cca                                              23

<210> SEQ ID NO 3
<211> LENGTH: 20
<212> TYPE: DNA
<213> ORGANISM: Artificial Sequence
<220> FEATURE:
<223> OTHER INFORMATION: ADAM10 forward primer

<400> SEQUENCE: 3

```
gctacgggca caagtgacta                                              20

<210> SEQ ID NO 4
<211> LENGTH: 22
<212> TYPE: DNA
<213> ORGANISM: Artificial Sequence
<220> FEATURE:
<223> OTHER INFORMATION: ADAM10 reverse primer

<400> SEQUENCE: 4
agacgtaagc agaaaccaga ca                                           22

<210> SEQ ID NO 5
<211> LENGTH: 20
<212> TYPE: DNA
<213> ORGANISM: Artificial Sequence
<220> FEATURE:
<223> OTHER INFORMATION: ADAM17 forward primer

<400> SEQUENCE: 5
agctccaaaa ctggaccacc                                              20

<210> SEQ ID NO 6
<211> LENGTH: 20
<212> TYPE: DNA
<213> ORGANISM: Artificial Sequence
<220> FEATURE:
<223> OTHER INFORMATION: ADAM17 reverse primer

<400> SEQUENCE: 6
gctgctattt gggaagggt                                               20

<210> SEQ ID NO 7
<211> LENGTH: 20
<212> TYPE: DNA
<213> ORGANISM: Artificial Sequence
<220> FEATURE:
<223> OTHER INFORMATION: BCL-2 forward primer

<400> SEQUENCE: 7
gagacagcca ggagaaatca                                              20

<210> SEQ ID NO 8
<211> LENGTH: 20
<212> TYPE: DNA
<213> ORGANISM: Artificial Sequence
<220> FEATURE:
<223> OTHER INFORMATION: BCL-2 reverse primer

<400> SEQUENCE: 8
cctgtggatg actgagtacc                                              20

<210> SEQ ID NO 9
<211> LENGTH: 20
<212> TYPE: DNA
<213> ORGANISM: Artificial Sequence
<220> FEATURE:
<223> OTHER INFORMATION: TGF-alpha forward primer

<400> SEQUENCE: 9
tcagtcaatt tggccgggat                                              20

<210> SEQ ID NO 10
<211> LENGTH: 20
<212> TYPE: DNA
<213> ORGANISM: Artificial Sequence
```

```
<220> FEATURE:
<223> OTHER INFORMATION: TGF-alpha reverse primer

<400> SEQUENCE: 10
gggcaggttg gaagagatca                                               20

<210> SEQ ID NO 11
<211> LENGTH: 20
<212> TYPE: DNA
<213> ORGANISM: Artificial Sequence
<220> FEATURE:
<223> OTHER INFORMATION: S100A9 forward primer

<400> SEQUENCE: 11
acacatcatg gaggacctgg                                               20

<210> SEQ ID NO 12
<211> LENGTH: 20
<212> TYPE: DNA
<213> ORGANISM: Artificial Sequence
<220> FEATURE:
<223> OTHER INFORMATION: S100A9 reverse primer

<400> SEQUENCE: 12
tcaccctcgt gcatcttctc                                               20

<210> SEQ ID NO 13
<211> LENGTH: 20
<212> TYPE: DNA
<213> ORGANISM: Artificial Sequence
<220> FEATURE:
<223> OTHER INFORMATION: IGFBP3 forward primer

<400> SEQUENCE: 13
aactgtggcc atgactgagg                                               20

<210> SEQ ID NO 14
<211> LENGTH: 20
<212> TYPE: DNA
<213> ORGANISM: Artificial Sequence
<220> FEATURE:
<223> OTHER INFORMATION: IGFBP3 reverse primer

<400> SEQUENCE: 14
agtctccctg agcctgactt                                               20

<210> SEQ ID NO 15
<211> LENGTH: 18
<212> TYPE: DNA
<213> ORGANISM: Artificial Sequence
<220> FEATURE:
<223> OTHER INFORMATION: MDK forward primer

<400> SEQUENCE: 15
ctcccggaaa ggcactgg                                                 18

<210> SEQ ID NO 16
<211> LENGTH: 17
<212> TYPE: DNA
<213> ORGANISM: Artificial Sequence
<220> FEATURE:
<223> OTHER INFORMATION: MDK reverse primer

<400> SEQUENCE: 16
cacctggggc ggtttcc                                                  17
```

<210> SEQ ID NO 17
<211> LENGTH: 20
<212> TYPE: DNA
<213> ORGANISM: Artificial Sequence
<220> FEATURE:
<223> OTHER INFORMATION: CMTM3 forward primer

<400> SEQUENCE: 17
gtatctgggc agcaggtgtt                                              20

<210> SEQ ID NO 18
<211> LENGTH: 20
<212> TYPE: DNA
<213> ORGANISM: Artificial Sequence
<220> FEATURE:
<223> OTHER INFORMATION: CMTM3 reverse primer

<400> SEQUENCE: 18
accaagtgca gacaaaccca                                              20

<210> SEQ ID NO 19
<211> LENGTH: 20
<212> TYPE: DNA
<213> ORGANISM: Artificial Sequence
<220> FEATURE:
<223> OTHER INFORMATION: RALGAPA2 forward primer

<400> SEQUENCE: 19
cactcgaatg ccgtcagact                                              20

<210> SEQ ID NO 20
<211> LENGTH: 20
<212> TYPE: DNA
<213> ORGANISM: Artificial Sequence
<220> FEATURE:
<223> OTHER INFORMATION: RALGAPA2 reverse primer

<400> SEQUENCE: 20
tgcggtagtc tctggagtgt                                              20

<210> SEQ ID NO 21
<211> LENGTH: 21
<212> TYPE: DNA
<213> ORGANISM: Artificial Sequence
<220> FEATURE:
<223> OTHER INFORMATION: USP48 forward primer

<400> SEQUENCE: 21
ggccgtctgt ctcttggtat t                                            21

<210> SEQ ID NO 22
<211> LENGTH: 20
<212> TYPE: DNA
<213> ORGANISM: Artificial Sequence
<220> FEATURE:
<223> OTHER INFORMATION: USP48 reverse primer

<400> SEQUENCE: 22
tgcaccaaag caaaaagcct                                              20

<210> SEQ ID NO 23
<211> LENGTH: 19
<212> TYPE: DNA
<213> ORGANISM: Artificial Sequence
<220> FEATURE:
<223> OTHER INFORMATION: GAPDH forward primer

```
<400> SEQUENCE: 23
gaaggtgaag gtcggagtc                                               19

<210> SEQ ID NO 24
<211> LENGTH: 20
<212> TYPE: DNA
<213> ORGANISM: Artificial Sequence
<220> FEATURE:
<223> OTHER INFORMATION: GAPDH reverse primer

<400> SEQUENCE: 24
gaagatggtg atgggatttc                                              20

<210> SEQ ID NO 25
<211> LENGTH: 19
<212> TYPE: RNA
<213> ORGANISM: Artificial Sequence
<220> FEATURE:
<223> OTHER INFORMATION: GIPZ Human Lentiviral MEL-18 shRNA Clone Gene
      Set

<400> SEQUENCE: 25
agacaauguc uugaagugu                                               19

<210> SEQ ID NO 26
<211> LENGTH: 23
<212> TYPE: DNA
<213> ORGANISM: Artificial Sequence
<220> FEATURE:
<223> OTHER INFORMATION: ADAM10 promoter primer

<400> SEQUENCE: 26
gctcggaaaa ttacatctcg gac                                          23

<210> SEQ ID NO 27
<211> LENGTH: 20
<212> TYPE: DNA
<213> ORGANISM: Artificial Sequence
<220> FEATURE:
<223> OTHER INFORMATION: ADAM10 promoter primer

<400> SEQUENCE: 27
gccccagtga tgcgaacata                                              20

<210> SEQ ID NO 28
<211> LENGTH: 21
<212> TYPE: DNA
<213> ORGANISM: Artificial Sequence
<220> FEATURE:
<223> OTHER INFORMATION: ADAM17 promoter primer

<400> SEQUENCE: 28
gccgctttct acagctcctt t                                            21

<210> SEQ ID NO 29
<211> LENGTH: 20
<212> TYPE: DNA
<213> ORGANISM: Artificial Sequence
<220> FEATURE:
<223> OTHER INFORMATION: ADAM17 promoter primer

<400> SEQUENCE: 29
gcctcctttg tcttgatgcc                                              20
```

BIOMARKER FOR HER2-POSITIVE CANCER AND ANTI-HER2 THERAPY AND APPLICATIONS THEREOF

CROSS REFERENCE TO RELATED APPLICATIONS

This application is a National Stage of International Application No. PCT/KR2018/002791 filed Mar. 8, 2018, claiming priority based on Korean Patent Applications No. 10-2017-0029627, filed Mar. 8, 2017 and 10-2017-0042224 filed Mar. 31, 2017.

TECHNICAL FIELD

The present invention relates to a biomarker for human epidermal growth factor receptor2 (HER2)-positive cancer and anti-HER2 therapy, and a use thereof.

BACKGROUND ART

Although a drug is taken properly according to the doctor's prescription, it may have different actions depending on a person, and it has been reported that about 2 million patients have experienced drug side effects, and 0.5% of these patients died from the drug side effects. In addition, only one third of patients prescribed drugs exhibit a desired therapeutic effect, and the report that the leading cause of death in the United States results from adverse drug reactions is an example clearly showing the blind spot of "one size fits all" medication. The biggest reason for differences in drug response among individuals is a "genetic factor." Since different persons have different genes, they have a difference in the amounts of enzymes and proteins in the body, and thus also have a difference in drug metabolism. Such interpersonal diversity makes it difficult to estimate a drug effect and stability in a specific patient, and therefore, to overcome this problem, a personalized medical approach based on the genetic information of each patient is required.

MEL-18 is a protein of the polycomb group (PcG) belonging to polycomb-repressive complex 1 (PRC1). PcG proteins are important epigenetic regulators which consist of two multicomplexes: one is polycomb-repressive complex 2 (PRC2), which is an initiation complex of a silent gene, catalyzing histone 3 tri-methylation in lysine-27 (H3K27me3); and the other is PRC1, which recognizes H3K27me3 and maintains gene silencing via various mechanisms including histone H2A mono-ubiquitination on lysine-119 (H2AK119ub) and blockade of transcriptional initiation machinery (1-3). While MEL-18 homolog BMI-1 and the core components of PRC1 have been well established, the role of MEL-18 in PRC1/2-mediated epigenetic gene silencing is poorly understood. Previous studies showed that MEL-18 is associated with cell proliferation, angiogenesis, and inhibition of cancer stem cells (CSCs) and epithelial mesenchymal transition (EMT) in breast cancer (4, 11-14). In addition, it has been reported that MEL-18 loss mediates the decrease in estrogen receptors (ERs), hormone independence and tamoxifen resistance (15), leading to association with triple-negative breast cancer (TNBC), and also revealed that MEL-18 loss plays a decisive role in the more aggressive progression of breast cancer.

Breast cancer having HER2 amplification or overexpression, accounting for 15 to 25% of all types of breast cancer, is considered an aggressive phenotype (16, 17). HER2 (called ErbB/HER) is a member of the epidermal growth factor receptor family of receptor tyrosine kinases (RTKs). Since HER2 has no identified ligand but is present in a suitable structure for homo- or hetero dimerization with other ErbB family members, it induces various types of oncogenic signaling associated with cell proliferation, survival, CSC and metastasis (18-21). Over the past several decades, HER2 has been considered a major therapeutic target for HER2-positive (HER2+) breast cancer (16, 18). Trastuzumab, which is a humanized monoclonal antibody against the HER2 extracellular domain, is the most common drug for HER2+ breast cancer patients and has received FDA approval (22), but only 30% of metastatic breast cancer patients respond to treatment with trastuzumab alone, and many patients acquire resistance to continuous treatment (23-26). There are several mechanisms of trastuzumab resistance, including target alteration (27, 28), ligand production, dimerization between ErbB family members (29-31), downstream mutation (32), and bypass signaling (33). Particularly, heterodimerization between ErbB family receptors is the main cause of bypassing the trastuzumab inhibitory effect against HER2 (34). Therefore, various strategies for overcoming trastuzumab resistance using target drugs for ErbB signaling such as lapatinib (35) and pertuzumab (36) have been attempted. However, there is still a demand for complete understanding of trastuzumab resistance and new therapeutic strategies for HER2-positive cancers.

DISCLOSURE

Technical Problem

To solve the conventional problems, the inventors had continuously studied to identify that a tumor suppressor MEL-18 plays a pivotal role for mediating responses to HER2-targeted drugs against HER2-positive cancers and to suggest a new therapeutic strategy for HER2-positive cancers.

Specifically, it was confirmed that MEL-18 is amplified only in almost half of HER2+ cancer patients, and it was newly found that MEL-18 inhibits resistance to HER2-targeted drugs, particularly, trastuzumab, and inhibits downstream signaling through PcG-dependent epigenetic regulation of ErbB ligand sheddases ADAM10/17. Accordingly, it was confirmed that MEL-18 serves as a promising prognostic factor or predictor for responses to anti-HER2 therapy in HER2-positive cancers, and when MEL-18 is used, resistance to HER2-targeted therapy can be overcome, and thus the present invention was completed.

Technical Solution

The present invention provides a composition for companion diagnostics for HER2-targeted drugs against HER2-positive cancers, the composition including an agent for measuring the copy number of MEL-18 gene, the mRNA expression level of the MEL-18 gene and/or the expression level of MEL-18 protein in order to suggest a novel therapeutic strategy for HER2-positive cancers.

The composition for companion diagnostics may be for providing information on, specifically, the need for administration of HER2-targeted drugs; the need for administration of ADAM10 and/or ADAM17 inhibitor(s); the possibility of manifesting drug resistance to HER2-targeted drugs; the sensitivity to HER2-targeted drugs; prediction of prognosis after treatment with HER2-targeted drugs; or the need for co-administration of HER2-targeted drugs and ADAM10 and/or ADAM17 inhibitor(s).

The cancer may be, but is not limited to, selected from the group consisting of breast cancer, gastric cancer, lung cancer, esophageal carcinoma, bladder cancer and colon cancer.

In the composition, an agent for measuring the copy number of MEL-18 gene or the mRNA expression level of the MEL-18 gene may be selected from a sense primer, an antisense primer and a probe, which complementarily bind to the MEL-18 gene or mRNA thereof.

In the composition, an agent for measuring a protein level may be selected from the group consisting of an antibody, an aptamer and a probe, which specifically bind to MEL-18 protein.

The HER2-targeted drug may be any drug targeting HER2, and may be, but is not limited to, selected from the group consisting of trastuzumab, pertuzumab and trastuzumab emtansine (T-DM1).

In addition, the present invention provides a companion diagnostic method for HER2-targeted drugs against HER2-positive cancers, the method including measuring the copy number of MEL-18 gene; the mRNA expression level of the MEL-18 gene; or the expression level of MEL-18 protein in a sample obtained from subjects with HER2-positive cancers.

The companion diagnostic method may be for providing information on the need for administration of HER2-targeted drugs; the need for administration of ADAM10 and/or ADAM17 inhibitor(s); the possibility of manifesting drug resistance to HER2-targeted drugs; the sensitivity to HER2-targeted drugs; prediction of prognosis after treatment with HER2-targeted drugs; or the need for co-administration of HER2-targeted drugs and ADAM10 and/or ADAM17 inhibitor(s).

The companion diagnostic method may further include, when the copy number of the MEL-18 gene; the mRNA expression level of the MEL-18 gene; or the expression level of the MEL-18 protein in a sample is lower than a predetermined value, providing information on the possibility that subjects can fall under one or more of the following categories, determined from the measurement result:

the need for administration of ADAM10 and/or ADAM17 inhibitor(s);

a high possibility of manifesting drug resistance to HER2-targeted drugs;

low sensitivity to HER2-targeted drugs;

a poor prognosis after treatment with HER2-targeted drugs; or the need for co-administration of HER2-targeted drugs with ADAM10 and/or ADAM17 inhibitor(s).

The companion diagnostic method may further include providing information on one or more selected from the group consisting of MEL-18 gene; MEL-18 gene expression activators; MEL-18 proteins; MEL-18 protein expression activators; ADAM10 gene inhibitors; ADAM17 gene inhibitors; ADAM10 protein expression inhibitors; ADAM17 protein expression inhibitors; ADAM10 protein activity inhibitors; and ADAM17 protein activity inhibitors, or providing one or more thereof with HER2-targeted drugs in order to treat HER2-positive cancers of the individual.

The HER2-targeted drug may be any drug targeting HER2, and may be, but is not limited to, selected from the group consisting of trastuzumab, pertuzumab and T-DM1.

In this method, the gene copy number; the mRNA expression level of the MEL-18 gene; or the expression level of the MEL-18 protein may be verified by a method selected from the group consisting of fluorescent in situ hybridization (FISH), comparative genomic hybridization (CGH-based array), a single nucleotide polymorphism (SNP) array, sequence assembly comparison, paired-end sequencing, multiplex ligation dependent probe amplification (MLPA), multiplex amplifiable probe hybridization (MAPH), quantitative multiplex PCR of short fluorescent fragments (QMPSF), microsatellite genotyping, Southern blotting, immunohistochemistry (IHC), polymerase chain reaction (PCR), quantitative PCR (qPCR), quantitative real-time PCR (qRT-PCR), real-time PCR, microarray-based comparative genomic hybridization and ligase chain reaction (LCR).

In addition, the present invention provides a kit for companion diagnostics for HER2-targeted drugs, which includes an agent for measuring the copy number of MEL-18 gene; a MEL-18 mRNA expression level; and/or a MEL-18 protein expression level.

The kit may further include an agent for measuring the copy number of the HER2 gene, the mRNA expression level of the HER2 gene or the expression level of the HER2 protein.

In the kit, the agent for measuring the copy number of a gene or the mRNA expression level of the gene may be selected from the group consisting of a sense primer, an antisense primer and a probe, which complementarily bind to the MEL-18 gene or mRNA thereof or the HER2 gene or mRNA thereof.

In the kit, the agent for measuring a protein expression level may be selected from the group consisting of an antibody, an aptamer and a probe, which specifically bind to the MEL-18 protein or the HER2 protein.

The kit may be for providing information on the need for administration of HER2-targeted drugs; the need for administration of ADAM10 and/or ADAM17 inhibitor(s); the possibility of manifesting drug resistance to HER2-targeted drugs; the sensitivity to HER2-targeted drugs; prediction of prognosis after treatment with HER2-targeted drugs; or the need for co-administration of HER2-targeted drugs and ADAM10 and/or ADAM17 inhibitor(s).

In addition, the present invention provides an anticancer pharmaceutical composition, which includes one or more selected from the group consisting of MEL-18 genes, MEL-18 gene expression activators, MEL-18 proteins, MEL-18 protein activators, ADAM10 gene inhibitors, ADAM10 protein activity inhibitors, ADAM17 gene inhibitors, and ADAM17 protein activity inhibitors as an active ingredient, for treating subjects with HER2-positive cancers that have the copy number of MEL-18 gene, the mRNA expression level of the MEL-18 gene, and/or the expression level of MEL-18 protein, which are/is lower than predetermined value(s); and/or have or expected to have drug resistance to HER2-targeted drugs.

In addition, the present invention provides a pharmaceutical composition, which includes one or more selected from the group consisting of MEL-18 gene, MEL-18 gene expression activators, MEL-18 proteins, MEL-18 protein activators, ADAM10 gene inhibitors, ADAM10 protein activity inhibitors, ADAM17 gene inhibitors, and ADAM17 protein activity inhibitors as an active ingredient, for inhibiting or improving resistance to HER2-targeted drugs in HER2-positive cancer patients.

In addition, the present invention provides a pharmaceutical composition, which includes one or more selected from the group consisting of MEL-18 gene, MEL-18 gene expression activator, MEL-18 protein, the MEL-18 protein activator, ADAM10 gene inhibitors, ADAM10 protein activity inhibitor, ADAM17 gene inhibitor, and ADAM17 protein activity inhibitor as an active ingredient, for assisting treatment of a HER2+ cancer patient with HER2-targeted drugs.

In the pharmaceutical composition, the ADAM10 and/or ADAM17 gene inhibitor(s) may be one or more selected from the group consisting of an antisense nucleotide, small interfering RNA (siRNA) and short hairpin RNA (shRNA), which complementarily bind to mRNA of ADAM10 and/or ADAM17 gene(s).

In the composition, the ADAM10 and/or ADAM17 protein activity inhibitor(s) may be one or more selected from the group consisting of a compound, a peptide, a peptide mimetic, an aptamer, an antibody, and a natural substance, which specifically bind to ADAM10 and/or ADAM17 protein(s).

In the composition, the ADAM10 and/or ADAM17 protein activity inhibitor(s) may be one or more selected from the group consisting of INCB3619, INCB7839, WAY-022, TMI-2, CGS 27023, GW280264 and GI254023.

The composition may be administered together with HER2-targeted drugs, or simultaneously or sequentially co-administered with HER2-targeted drugs.

The HER2-targeted drug may be any drug targeting HER2, and may be, but is not limited to, selected from the group consisting of trastuzumab, pertuzumab and T-DM1.

In addition, the present invention provides a composition for screening an agent that improves resistance to HER2-targeted drugs or is co-administered with HER2-targeted drugs, which includes one or more selected from the group consisting of MEL-18 gene, MEL-18 protein, ADAM10 gene, ADAM10 protein, ADAM17 gene and ADAM17 protein.

In addition, the present invention provides a method of screening a drug that improves resistance to HER2-targeted drugs or is co-administered with HER2-targeted drugs, which includes: contacting candidate materials with one or more selected from the group consisting of MEL-18 gene, MEL-18 protein, ADAM10 gene, ADAM10 protein, ADAM17 gene and ADAM17 protein; and selecting a candidate material that increases the copy number of the MEL-18 gene, the mRNA expression level of the MEL-18 gene, or the expression level of a protein expressed from the gene, or inhibits the expression level(s) of the ADAM10 and/or ADAM17 gene(s) or the expression level of a protein expressed from the gene.

The screening method may further include judging a candidate material that promotes amplification of the MEL-18 gene; the mRNA expression level of the MEL-18 gene; or the expression level of a protein expressed from the gene or inhibits the mRNA expression level(s) of the ADAM10 and/or ADAM17 gene(s) or the expression level of a protein expressed from the gene to be a drug for inhibiting or improving resistance to HER2-targeted drugs.

In addition, the present invention provides a method of treating subjects having HER2-posivive cancers, which includes administering a pharmaceutical composition including one or more selected from the group consisting of MEL-18 gene; MEL-18 gene expression activators; MEL-18 proteins; MEL-18 protein expression activators; ADAM10 gene inhibitors; ADAM17 gene inhibitors; ADAM10 protein expression inhibitors; ADAM17 protein expression inhibitors; ADAM10 protein activity inhibitors; and ADAM17 protein activity inhibitors to the subjects with HER2-positive cancers, wherein subjects have the copy number of MEL-18 gene, the mRNA expression level of the MEL-18 gene, and/or the expression level of MEL-18 protein, which are/is lower than predetermined value(s); and/or subjects have or expected to have drug resistance to HER2-targeted drugs.

The method may further include co-administering HER2-targeted drugs to subjects receiving administration of the pharmaceutical composition.

Before administration of the pharmaceutical composition, the method may further include measuring the copy number of the MEL-18 gene, the mRNA expression level of the MEL-18 gene, or the expression level of the MEL-18 protein from a sample obtained from the individual with HER2-positive cancers.

In this method, the ADAM10 and/or ADAM17 gene or its mRNA expression inhibitor may be one or more selected from the group consisting of an antisense nucleotide, small interfering RNA (siRNA) and short hairpin RNA (shRNA), which complementarily bind to mRNA of ADAM10 and/or ADAM17 gene(s).

In this method, the ADAM10 and/or ADAM17 protein activity inhibitor may be one or more selected from the group consisting of a compound, a peptide, a peptide mimetic, an aptamer, an antibody, and a natural substance, which specifically bind to ADAM10 and/or ADAM17 protein(s).

In this method, the ADAM10 and/or ADAM17 protein activity inhibitor(s) may be one or more selected from the group consisting of INCB3619, INCB7839, WAY-022, TMI-2, CGS 27023, GW280264 and GI254023.

In addition, the present invention provides a use of an agent for measuring the copy number of MEL-18 gene; the mRNA expression level of the MEL-18 gene; and/or the expression level of MEL-18 protein in a sample obtained from subjects with HER2-positive cancers in companion diagnostics for HER2-targeted drugs.

In addition, the present invention provides a use of an agent for measuring the copy number of MEL-18 gene; the mRNA expression level of the MEL-18 gene; and/or the expression level of MEL-18 protein to prepare a composition for identifying subjects with HER2-positive cancers, wherein subjects have the copy number of MEL-18 gene, the mRNA expression level of the MEL-18 gene, and/or the expression level of MEL-18 protein, which are/is lower than predetermined value(s); and/or subjects have or expected to have drug resistance to HER2-targeted drugs.

The present invention also provides a use of an agent for measuring the copy number of MEL-18 gene; the mRNA expression level of the MEL-18 gene; and/or the expression level of MEL-18 protein to prepare a composition for companion diagnostics for HER2-targeted drugs with respect to subjects with HER2-positive cancers, wherein subjects have the copy number of MEL-18 gene, the mRNA expression level of the MEL-18 gene, and/or the expression level of MEL-18 protein, which are/is lower than predetermined value(s); and/or subjects have or expected to have drug resistance to HER2-targeted drugs.

In addition, the present invention provides a use of an agent for measuring the copy number of MEL-18 gene; the mRNA expression level of the MEL-18 gene; or the expression level of MEL-18 protein in a sample obtained from subjects with HER2-positive cancers to prepare a kit for companion diagnostics for HER2-targeted drugs.

In addition, the present invention provides an application of one or more selected from the group consisting of MEL-18 gene, MEL-18 gene expression activator, MEL-18 protein, the MEL-18 protein activator, ADAM10 gene inhibitors, ADAM10 protein activity inhibitors, ADAM17 gene inhibitors and ADAM17 protein activity inhibitors to prepare a drug for treating subjects with HER2-positive cancers, wherein subjects have the copy number of MEL-18 gene, the mRNA expression level of the MEL-18 gene, and/or the expression level of MEL-18 protein, which are/is lower than predetermined value(s); and/or subjects have or expected to have drug resistance to HER2-targeted drugs.

Advantageous Effects

MEL-18 of the present invention is a prognostic factor and a predictor for a response of subjects to an anti-HER2-targeted drug against HER2-positive cancers, and can be used in companion diagnostics for HER2-targeted drugs for subjects with HER2-positive cancers, thereby determining whether an ADAM10 or 17 inhibitor should be administered or should be co-administered with HER2-targeted drugs, and thus overcoming resistance to the anti-HER2 therapy and improving its therapeutic efficacy. Therefore, HER2-positive cancers can be more effectively treated.

BRIEF DESCRIPTION OF DRAWINGS

FIG. 8A shows the result of the functional analysis of MEL-18 target genes by a microarray using Gene Set Enrichment Analysis (GSEA) according to an exemplary embodiment of the present invention, indicating GSEA with genes differentially expressed from MEL-18-knockdown BT474 cells, determined by a microarray analysis.

MODES OF THE INVENTION

Figure 1A:
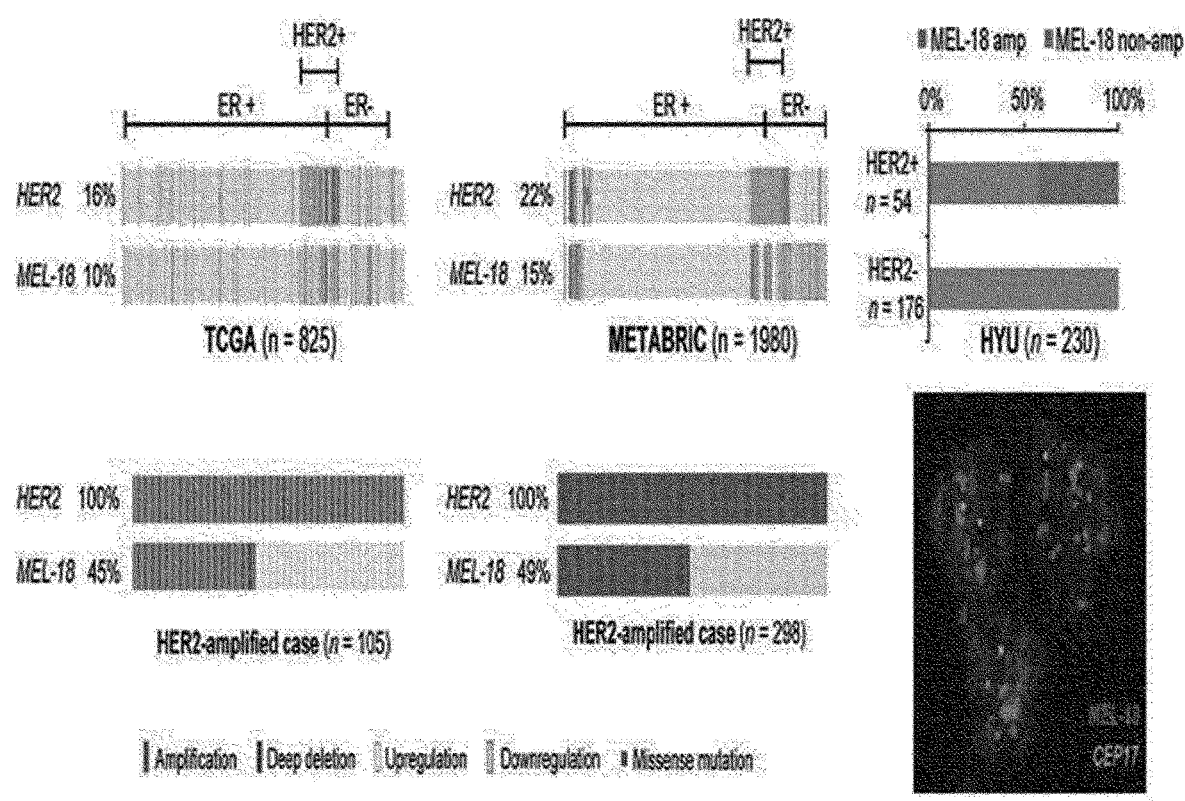
FIG. 1A shows that MEL-18 is associated with a positive survival result in HER2+ breast cancer, which represents the percentage of cases with genetic variation of MEL-18 in different breast cancer cohorts (TCGA and METABRIC; left) and a MEL-18 gene amplification status from a HYU cohort, determined by FISH analysis (right). In the lower right, there is the representative image of the case with MEL-18 amplification (MEL-18 signal: red; CEP17: green; DAPI: blue. MEL-18amp represents a MEL-18-amplified case; and MEL-18 non-amp represents a MEL-18 non-amplified case).

Hereinafter, the present invention will be described in detail.

However, the present invention can be modified in various ways, and have various forms, and thus specific embodiments and descriptions to be provided below are merely to help in understanding of the present invention, but not to limit the present invention to specific embodiments. It should be understood that the scope of the present invention includes all modifications, equivalents and alternatives within the idea and technical scope of the present invention.

The present invention relates to a composition for companion diagnostics for HER2-targeted drugs against HER2-positive cancers, which includes an agent for measuring the copy number of MEL-18 gene, the mRNA expression level of the MEL-18 gene and/or the expression level of MEL-18 protein.

MEL-18 is a protein of the polycomb group (PcG) belonging to polycomb-repressive complex 1 (PRC1). PcG proteins are a crucial epigenetic regulators consisting of two multicomplexes: one is PRC2, which is an initiation complex of a silencing gene, catalyzing histone 3 tri-methylation in lysine-27 (H3K27me3); and the other is PRC1, which recognizes H3K27me3 and maintains gene silencing via various mechanisms including histone H2A mono-ubiquitination on lysine-119 (H2AK119ub) and blockade of transcriptional initiation machinery (1-3). MEL-18 is also known as polycomb group ring finger 2, RNF110, or ZNF144, and NCBI or the like may be referenced for its gene, mRNA and protein data. For example, it is registered under NCBI Gene ID: 454614 (Homo sapiens (human)); NCBI Reference Sequence: NP_009075.1; or NCBI Gene ID: 7703, and includes all sequence data known as MEL-18, as well as the gene data.

In an exemplary embodiment of the present invention, it was confirmed that, when MEL-18 gene is not amplified or MEL-18 mRNA is less expressed in subjects with HER2+ breast cancer, MEL-18 has resistance to trastuzumab, which is HER2-targeted drugs, and when overexpression of MEL-18 is induced or ADAM10 and/or ADAM17 inhibitor(s) is(are) treated, resistance to trastuzumab is improved. In addition, MEL-18 is amplified only in half of individuals with HER2+ gastric cancer, lung cancer or esophageal carcinoma, similar to the breast cancer case. Accordingly, the MEL-18 of the present invention has a novel application as a marker for companion diagnostics to determine whether HER2-targeted drugs, or ADAM10 and/or ADAM17 inhibitor(s) should be applied, or applied individually or in combination to subjects with HER2-positive cancers.

The term "MEL-18" used herein is interpreted to include all of MEL-18 gene, mRNA of the MEL-18 gene, and MEL-18 protein. In addition, the MEL-18, MEL-18 gene or MEL-18 protein is understood to include a fragment or recombinant protein thereof having substantially the same activity as them, and codon-optimized cDNA. Accordingly, in the present invention, a MEL-18 expression level means the mRNA expression level of the MEL-18 gene or the expression level of the MEL-18 protein expressed from the gene. In addition, the term "HER2," "ADAM10," or "ADAM17" may be interpreted as a meaning including all of a gene, mRNA and a protein thereof.

The term "companion diagnostics" used herein means one of diagnostic tests for verifying the possibility of applying a specific drug to a specific patient, and in the present invention, to verify the possibility of applying HER2-targeted drugs or ADAM10 and/or ADAM17 inhibitor(s) to subjects with HER2-positive cancers, the copy number of the MEL-18 gene, its mRNA expression level or the expression level of the MEL-18 protein expressed from the gene may be measured, as a companion diagnostic marker, in individuals with the above-mentioned cancer. Therefore, in this aspect, the companion diagnostics used herein may be performed to provide information on the need for administration of HER2-targeted drugs; the need for administration of ADAM10 and/or ADAM17 inhibitor(s); the possibility of manifesting drug resistance to HER2-targeted drugs; the sensitivity to HER2-targeted drugs; prediction of prognosis after treatment with HER2-targeted drugs; or the need for co-administration of HER2-targeted drugs and ADAM10 and/or ADAM17 inhibitor(s).

The term "determination" used herein means distinguishing objects according to specific criteria. In the present invention, determination may be used as a meaning of distinguishing whether subjects diagnosed to have HER2-positive cancers or likely to have the cancer have or do not have drug resistance to HER2-targeted drugs, or whether the above-mentioned subjects have or do not have sensitivity to HER2-targeted drugs.

In addition, the expression "need for administration" is used herein for the purpose of determining whether a specific agent (drug) should be administered only to subjects expected to have a therapeutic effect with respect to the agent (drug), and such determination may be made by measurement of the level of a companion diagnostic marker. Specifically, in the present invention, to determine whether to administer HER2-targeted drugs; ADAM10 and/or ADAM17 inhibitor(s); or a combination of HER2-targeted drugs with ADAM10 and/or ADAM17 inhibitor(s), as a companion diagnostic marker, the copy number of the MEL-18 gene, the mRNA expression level thereof the expression level of the MEL-18 protein expressed from the gene may be measured.

The term "human epidermal growth factor receptor2 (HER2)-positive cancer" used herein means cancer exhibiting HER2 gene amplification or overexpression, and may be, but is not limited to, selected from the group consisting of HER2+ breast cancer, gastric cancer, lung cancer, esophageal carcinoma, bladder cancer and colon cancer. In an exemplary embodiment of the present invention, the HER2-positive cancers may be HER2+ breast cancer, HER2+ gastric cancer, or HER2+ lung cancer. Whether or not the cancer is HER2-positive (exhibiting gene amplification or overexpression) may be determined according to criteria generally used in the art to which the present invention belongs, which may vary according to clinical criteria for diagnosing HER2 positive in each country. In an exemplary embodiment of the present invention, it was confirmed that MEL-18 can be used as a companion diagnostic marker in HER2+ breast cancer cells, and in the cases of gastric cancer, lung cancer, esophageal carcinoma, bladder cancer and colon cancer, MEL-18 amplification characteristics similar to breast cancer were observed. It can be seen that the MEL-18 of the present invention can be used as a companion diagnostic marker for the above-mentioned types of cancer.

The composition for companion diagnostics according to the present invention includes an agent for measuring the copy number of the MEL-18 gene; the mRNA expression level thereof; and/or the expression level of the MEL-18 protein.

The term "copy number of a gene" is the number of specific genes in a specific genotype of each individual, meaning the number of a specific gene or gene fragment of which multiple copies are formed. It may be understood that the measurement of the copy number of a gene in the present invention is the same as measurement of a copy number variation (or copy number variant (CNV)) and a gene copy number (GCN), which are generally used in the art. In addition, when the copy number of a gene is same as or higher than a predetermined value, this can indicate that there is gene amplification, and when the copy number of a gene is the same as or lower than the predetermined value, this can indicate that there is no gene amplification. In the present invention, the "gene amplification" can be used interchangeably with gene duplication, which means that the number of gene copies is higher than the predetermined value. In an exemplary embodiment of the present invention, among values obtained by measuring the copy number of a gene through FISH in subjects with HER2+ breast cancer, when the copy number of the MEL-18 gene is higher than 6.0, which is the predetermined value, it is considered that there is gene amplification, followed by performing analysis.

The term "mRNA expression level" or "protein expression level" means the degree to which messenger RNA delivering the genetic information of a specific gene to a ribosome or a protein is expressed from the specific gene. When the mRNA or protein expression level is higher than a particular predetermined value (or a particular reference value), this indicates "overexpression". When the mRNA or protein expression level is the same as or less than the predetermined value, this indicates "low expression". In an exemplary embodiment of the present invention, a MEL-18 mRNA expression level (about 1 (TCGA in FIG. 1B), about 11 (METABRIC in FIG. 1B); measured through RNA-seq or a microarray, z-scores) corresponding to MEL-18 CNA 2 or more was set as a predetermined value for analysis. In another exemplary embodiment of the present invention, among the measured values obtained from a microarray, a group in which the mRNA expression value of MEL-18 corresponding to the top ⅔ (66%) was considered overexpressed (positive), followed by performing analysis.

The term "agent for measuring the copy number of a gene" or "agent for measuring an mRNA expression level" may be selected from the group consisting of a sense primer, an antisense primer and a probe, which complementarily bind to a gene or mRNA thereof, but the present invention is not limited thereto.

The "primer" used herein refers to a nucleic acid sequence having a short free 3' hydroxyl group, and a short nucleic acid sequence which can form a complementary template and base pair and serving as a starting point for the replication of a template strand. The primer may initiate DNA synthesis in a suitable buffer solution at a suitable temperature in the presence of a reagent for a polymerization reaction (DNA polymerase or reverse transcriptase) and four different dNTPs (deoxynucleoside triphosphates). In the present invention, the primer is a primer capable of specifically binding to the MEL-18 gene, preferably consisting of sense (forward) and antisense (reverse) nucleic acids having 7 to 50 nucleotide sequences. The primer may have an additional characteristic that does not change the basic property of the primer serving as the starting point of DNA synthesis. In addition, the primer nucleic acid sequence of the present invention may include a directly or indirectly detectable marker by spectroscopic, photochemical, biochemical, immunochemical or chemical means when needed.

In an exemplary embodiment of the present invention, the primer may be sense and/or antisense primer(s) complementary to the MEL-18 gene or its mRNA. The sense and antisense primers may be included alone or in combination. In addition, the primer may be a probe capable of specifically binding to MEL-18.

The "probe" used herein refers to a nucleic acid fragment such as RNA or DNA having a length of several nucleotides to several hundred bases, which can specifically bind to a specific nucleotide sequence. When labeled, the primer includes a form of an oligonucleotide probe, a single-stranded DNA probe, a double-stranded DNA probe or an RNA probe, which can confirm the presence or absence of a specific gene or its mRNA.

The primer or probe of the present invention may be chemically synthesized using a known method.

The "method of measuring the gene copy number" used herein may use all of conventional methods used in the art to which the present invention belongs. More specifically, both of full-length genome analysis and a target-specific method may be used. Specifically, a method selected from the group consisting of fluorescent in situ hybridization (FISH), comparative genomic hybridization (CGH-based array), a SNP array, sequence assembly comparison, paired-end sequencing, multiplex ligation dependent probe amplification (MLPA), multiplex amplifiable probe hybridization (MAPH), quantitative multiplex PCR of short fluorescent fragments (QMPSF), microsatellite genotyping, Southern blotting, immunohistochemistry (IHC), polymerase chain reaction (PCR), quantitative PCR (qPCR), quantitative real-time PCR (qRT-PCR), real-time PCR, microarray-based comparative genome hybridization and ligase chain reaction (LCR) may be used, but the present invention is not limited thereto.

The "method of measuring an mRNA expression level" used herein may use all of conventional methods used in the art to which the present invention belongs. More specifically, the method includes PCR, RT-PCR, competitive RT-PCR, real-time RT-PCR, RNase protection assay (RPA), Northern blotting, RNA-sequencing (RNA-seq), a nano string or a DNA chip, but the present invention is not limited thereto. The detection methods may be used to confirm overexpression/low expression of mRNA by comparing the mRNA expression level of a biological sample obtained from subjects requiring companion diagnostics with the mRNA expression level in a comparative sample, to confirm overexpression/low expression by measuring the mRNA expression levels of the samples and comparing them with the predetermined value, or to confirm an increase/decrease in the expression in a comparison in which the MEL-18 mRNA expression level after treatment with HER2-targeted drugs is lower than that before treatment with the HER2 agent.

The "agent for measuring a protein level" used herein may be selected from the group consisting of an antibody, an aptamer and a probe, which specifically bind to a protein, but the present invention is not limited thereto. In the present invention, the agent may be selected from the group consisting of an antibody, an aptamer and a probe, which specifically bind to the MEL-18 protein.

In addition, the "method of measuring a protein expression level" may use all of conventional methods used in the art to which the present invention belongs. More specifically, a protein chip analysis, an immunoassay, a ligand binding assay, Matrix Assisted Laser Desorption/Ionization Time of Flight Mass Spectrometry (MALDI-TOF), Surface-Enhanced Laser Desorption/Ionization Time of Flight Mass Spectrometry (SELDI-TOF), a radioimmunoas say, a radioimmunoprecipitation assay, Ouchteroni immunodiffusion, rocket immunoelectrophoresis, immunohistochemistry (IHC), a complement fixation assay, two-dimensional electrophoresis analysis, liquid chromatography-mass spectrometry (LC-MS), liquid chromatography-mass spectrometry/mass spectrometry (LC-MS/MS), Western blotting or an enzyme linked immunosorbent assay (ELISA) may be used, but the present invention is not limited thereto.

The term "drug resistance" used herein means that there is no statistically significant cellular or biological response to a specific drug. Specifically, it means that the death rate of cancer cells is reduced or there is no apoptosis of the cancer cells due to treatment with a drug.

The term "HER2-targeted drug(s)" are/is used in combination with a "HER2 gene or protein inhibitor," and has an effect of inhibiting or hindering the expression or activity of the HER2 gene or protein inhibitor by specifically acting on the HER2 gene or protein, and includes all types of anti-HER2 agents. Specifically, it may be an expression or activity inhibitor through the inhibition of HER2 dimerization.

The HER2 expression inhibitor may be one or more selected from the group consisting of an antisense nucleotide, small interfering RNA (siRNA) and short hairpin RNA (shRNA), which complementarily bind to mRNA of the gene.

The HER2 protein activity inhibitor may be one or more selected from the group consisting of a natural or synthetic compound, a peptide, a peptide mimetic, an aptamer and an antibody, which specifically bind to the protein.

The HER2-targeted drug means a therapeutic agent targeting a HER2 receptor, for example, an antibody therapeutic. In the present invention, as a HER2-targeted drug, any therapeutic targeting a HER2 receptor, which has already been disclosed in papers and patents, other than medications which are now commercially available, may be included. Specifically, it has been identified that, in the present invention, signaling of a HER2 receptor is mediated by MEL-18, and it can be seen that MEL-18-mediated companion diagnostics of determining resistance/sensitivity to HER2-targeted drugs, restoring sensitivity or determining treatment with an ADAM10/17 inhibitor may be widely applied regardless of the type of therapeutic agent, and therefore, all therapeutic agents targeting a HER2 receptor may be included in the present invention. Specifically, the therapeutic agent targeting a HER2 receptor may be selected from the group consisting of trastuzumab, pertuzumab and trastuzumab emtansine (T-DM1)), but the present invention is not limited thereto.

The trastuzumab, also called Herceptin™, is a therapeutic agent for metastatic cancer which is triggered by overexpression of the HER2 gene or its gene product, and an antibody therapeutic agent recognizing an extracellular moiety of HER2 as an antigen epitope.

Pertuzumab, an anti-HER2 therapeutic agent for a metastatic disease, is chemically available under the trade name Perjeta. Pertuzumab blocks HER2 signaling to inhibit HER2 dimerization. Pertuzumab may be used in combination with trastuzumab or docetaxel.

Trastuzumab emtansine (T-DM1), also called ado-trastuzumab emtansine, is an antibody-drug conjugate which is commercially available under the trade name Kadcyla. T-DM1 has a structure in which trastuzumab is linked to the cytotoxic agent emtansine (DM1).

The term "individual" or "patient" used herein may be a vertebrate, and particularly a mammal, and the mammal includes all of a dog, a horse, a cat, a cow, a primate, a mouse and a rat, and preferably, a human.

In addition, the present invention relates to a method for companion diagnostics for HER2-targeted drugs against HER2-positive cancers, which includes measuring the copy number of MEL-18 gene; the mRNA expression level of the MEL-18 gene; or the expression level of MEL-18 protein in samples obtained from individuals with HER2-positive cancers.

All descriptions regarding the composition for companion diagnostics may also be applied or applied mutatis mutandis to the method for companion diagnostics of the present invention.

The method for companion diagnostics may be for providing information on, specifically, the need for administration of HER2-targeted drugs; the need for administration of ADAM10 and/or ADAM17 inhibitor(s); the possibility of manifesting drug resistance to HER2-targeted drugs; the sensitivity to HER2-targeted drugs; prediction of prognosis after treatment with HER2-targeted drugs; or the need for co-administration of HER2-targeted drugs and ADAM10 and/or ADAM17 inhibitor(s).

The method for companion diagnostics may further include, when the copy number of the MEL-18 gene; the mRNA expression level of the MEL-18 gene; or the expression level of the MEL-18 protein in a sample is lower than a predetermined value, providing information on the possibility that subjects can fall under one or more of the following categories, determined from the measurement result:

the need for administration of ADAM10 and/or ADAM17 inhibitor(s);

a high possibility of manifesting drug resistance to HER2-targeted drugs;

low sensitivity to HER2-targeted drugs;
a poor prognosis after treatment with HER2-targeted drugs; or
the need for co-administration of HER2-targeted drugs with ADAM10 and/or ADAM17 inhibitor(s).

When the copy number of the gene and/or the mRNA expression level is the same or less than the predetermined value, or the protein activity level is the same or less than the predetermined value, it may be determined as non-amplification (or negative) of the MEL-18 gene or low MEL-18 expression, indicating no amplification or reduced expression of the MEL-18 gene.

An individual considered having non-amplification (negative) or low expression of MEL-18 through the measurement, that is, subjects exhibiting the copy number of the MEL-18 gene; the mRNA expression level of the MEL-18 gene; or the expression level of a protein encoded by the MEL-18 gene, which are lower than the predetermined values, may be classified as one having low sensitivity to HER2-targeted drugs, or one having resistance to the therapeutic agent. In addition, when the individual is one receiving administration of HER2-targeted drugs, the prognosis of treatment with HER2-targeted drugs may be predicted to be poor, and the individual is considered to have drug resistance to the administered HER2-targeted drug. Therefore, to increase sensitivity or reduce resistance to the HER2-targeted drug in an individual, it may be judged that there is a need for administration (or prescription) of an ADAM10 and/or ADAM17 inhibitor or co-administration of the HER2-targeted drug with an ADAM10 and/or ADAM17 inhibitor(s); or administration (or prescription) of the MEL-18 gene, MEL-18 gene expression activators, the MEL-18 protein or a MEL-18 protein activator.

The term "predetermined value (or reference value)" means a benchmark value for dividing amplification/non-amplification of a gene; or overexpression/low expression of mRNA or a protein. The reference value may be, for example, an average gene copy number or an average mRNA/protein expression level of subjects before treatment with a specific drug, or an average gene copy number or an average mRNA/protein expression level of a normal individual, but the present invention is not limited thereto. In addition, the reference value may be determined according to the distribution of the average gene copy number or the distribution of a mRNA/protein expression level of a specific patient group, but the present invention is not limited thereto.

Specifically, the gene copy number, the mRNA expression level or protein expression level is determined by measuring an average gene copy number, the mRNA expression level or protein expression level from a sample of each individual using a method of measuring a gene, mRNA or protein level, which is conventionally used in the art of the present invention, and a measured value in the distribution of measured values corresponding to the top 1%, 2%, 3%, 4%, 5%, 6%, 7%, 8%, 9% 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99% may be set as a predetermined value.

For example, in the case of a MEL-18 gene copy number, the predetermined value may be 1, 2, 3, 4, 5, 6, 7, 8, 9, or 10 copies or more.

In an exemplary embodiment of the present invention, a gene copy number of each individual was measured by FISH, and the gene copy number accounting for the approximate top 50% was set as the benchmark for dividing positive/negative of the MEL-18 gene. Here, the predetermined value was 6 copies, and when the gene copy number was more than 6.0 copies (gene/chromosome ratio >6.0), it was classified as amplification of the MEL-18 gene.

In another exemplary embodiment, copy number variation (CNV) was detected through whole-exome sequencing or the SNP array 6.0, and the results were classified as follows using the GISTIC algorithm: (+2 (amplification), +1 (duplication), 0 (neutral), −1 (deletion), −2 (homozygous deletion), +2 or more (in the case of a gene copy number of 4 or more, it was classified as amplification).

In another exemplary embodiment, a protein expression level is measured by immunohistochemistry using a MEL-18 antibody, and the intensity and area of staining were quantified, thereby obtaining the measured value of protein expression. The final measured value (score) for the protein expression is obtained by multiplying two scores obtained by grading the protein expression as follows: 0 (no cells stained), 1 (1% to 24% cells stained), 2 (25% to 49% cells stained), 3 (50% to 74% cells stained), and 4 (75% to 100% cells stained) according to the percentage of the immunostained cells, and 0 (no staining), 1 (weak staining), 2 (moderate staining) and 3 (strong staining) according to the intensity of the staining. The case in which the distribution of the final measured values corresponds to the top 25% was set as the benchmark for dividing positive/negative (or overexpression/low expression), and at this time, the measured value was 4. As a result, for samples or individuals with the measured value of 4 or more, the protein expression may be considered overexpressed or positive.

In still another exemplary embodiment, analysis was carried out with the MEL-18 mRNA expression levels (about 1 (TCGA of FIG. 1B), about 11 (METABRIC of FIG. 1B); measured through RNA-seq or microarray, z-scores), corresponding to MEL-18 CNA 2 or more, which were set as predetermined values, and in yet another exemplary embodiment, from the measured values obtained through a microarray, a group with MEL-18 mRNA expression levels corresponding to top ⅔ (66%) was determined as overexpressed (positive), followed by performing analysis.

Other than these, for the readout of the MEL-18 gene or protein, or the setting of predetermined values, [Jeong-Yeon Lee et al., jci.org Volume 125, Number 5, May 2015, "MEL-18 loss mediates estrogen receptor-α downregulation and hormone independence"] may be referenced.

As described above, the predetermined value of the present invention may be set according to a conventional method used in the art to which the present invention belongs, and may use various types of statistical methods and software for obtaining statistics. In the present invention, the predetermined value may vary according to the total number (n) of samples (or individuals) or a purpose of setting a predetermined value. While, when a kit is manufactured using the MEL-18 marker of the present invention, the predetermined value may vary according to an optimization extent of the product, the predetermined value may be set with reference to the present invention, and thus all of them are included in the present invention. In addition, the predetermined value of the present invention may be a predetermined value set by a conventional method.

In addition, the method may further include prescribing (or providing information for prescription) one or more selected from the group consisting of the MEL-18 gene, MEL-18 gene expression activators, the MEL-18 proteins, MEL-18 protein activators, ADAM10 gene inhibitors, ADAM10 protein activity inhibitors, ADAM17 gene inhibitors and ADAM17 protein activity inhibitors to subjects classified as exhibiting no (or negative) amplification of the MEL-18 gene or low MEL-18 expression. In addition, the method may further include prescribing (or providing information for prescription) one or more selected from the group consisting of the MEL-18 gene, MEL-18 gene expression activators, the MEL-18 proteins, MEL-18 protein activators, ADAM10 gene inhibitors, ADAM10 protein activity inhibitors, ADAM17 gene inhibitors and ADAM17 protein activity inhibitors in combination with HER2-targeted drugs to subjects classified as exhibiting no (or negative) amplification of the MEL-18 gene or low MEL-18 expression.

The term "sample" used herein may be urine, a body fluid (including blood, lymph, or tissue fluid), or biopsy tissue, and preferably, one obtained from subjects with cancer, and more preferably, one obtained from subjects suspected of, determined or diagnosed with HER2-positive cancers.

The present invention also provides a kit or system for companion diagnostics for HER2-targeted drugs, which includes an agent for measuring the copy number of the MEL-18 gene; the mRNA expression level of the MEL-18 gene; or the expression level of the MEL-18 protein.

All descriptions regarding the composition or method for companion diagnostics may also be applied mutatis mutandis to the kit or system for companion diagnostics of the present invention.

The kit or system may further include an agent for measuring the copy number of the HER2 gene; the mRNA expression level of the HER2 gene or the expression level of the HER2 protein. In this case, the kit for companion diagnostics of the present invention may simultaneously determine whether subjects who provided a sample is HER2+, and has resistance (or sensitivity) to HER2-targeted drugs. Whether or not one is HER2+ may be determined according to a method known in the art to which the present invention belongs, and for example, in the case of HER2+ breast cancer, it may be considered according to the criteria disclosed in [J Clin Oncol. 2007 Jan. 1; 25(1):118-45. Epub 2006 Dec. 11; PMID: 17159189], and when the HER2 gene copy number is more than 6, it may be considered positive. However, not limited to the above examples, the criteria may vary depending on the type of HER2-positive cancers, and if there are methods and/or criteria decided by each country according to clinical standards, whether or not one is HER2+ may be determined thereby.

The agent for measuring the copy number or mRNA expression level of the gene may be selected from the group consisting of a sense primer, an antisense primer and a probe, which complementarily bind to each of the MEL-18 gene/mRNA or the HER2 gene/mRNA.

The agent for measuring a protein level may be selected from the group consisting of an antibody, an aptamer and a probe, which specifically bind to the MEL-18 protein or the HER2 protein.

The kit or system may be for providing information on, specifically, the need for administration of HER2-targeted drugs; the need for administration of ADAM10 and/or ADAM17 inhibitor(s); the possibility of manifesting drug resistance to HER2-targeted drugs; the sensitivity to HER2-targeted drugs; prediction of prognosis after treatment with HER2-targeted drugs; or the need for co-administration of HER2-targeted drugs and ADAM10 and/or ADAM17 inhibitor(s).

In an exemplary embodiment, the need for prescription of an anti-HER2 agent may be determined by verifying whether or not one is HER2+ from a sample obtained from subjects with cancer, and measuring the copy number of the MEL-18 gene, the mRNA expression level of the MEL-18 gene or a MEL-18 protein expression/activity level. Specifically, when the individual has the copy number and/or mRNA expression level of the MEL-18 gene, which are lower than the predetermined values, the individual may be defined as having low sensitivity to HER2-targeted drugs, or having resistance to HER2-targeted drugs. In addition, when the individual receives the administration of HER2-targeted drugs, it may be expected that the prognosis of treatment with HER2-targeted drugs will be poor, considering that the individual has drug resistance to the administered HER2-targeted drug. Accordingly, to increase the sensitivity or reduce resistance to HER2-targeted drugs in the individual, it may be considered that it is necessary to administer ADAM10 and/or ADAM17 inhibitor(s), or co-administer ADAM10 and/or ADAM17 inhibitor(s) with HER2-targeted drugs; or administer (or prescribe) the MEL-18 gene, MEL-18 gene expression activators, the MEL-18 protein or a MEL-18 protein activator.

The kit includes a diagnostic kit based on a conventional gene copy number, and mRNA expression and protein quantitative analyses without limitation. For example, the kit may be a RT-PCR kit, a DNA chip kit, a protein kit or an array kit. For a RT-PCR kit, in addition to primer pairs specific to the MEL-18 gene and/or the HER2 gene, a test tube or another suitable container, a reaction buffer, a deoxynucleotide (dNTP), enzymes such as Taq-polymerase and reverse transcriptase, a DNase or RNase inhibitor, and sterile water may be generally included as components of the kit. In addition, conventional technology for a kit or system for companion diagnostics may be applied to the present invention.

In addition, the present invention relates to an anti-cancer pharmaceutical composition, which includes one or more selected from the group consisting of MEL-18 gene, MEL-18 gene expression activators, MEL-18 proteins, MEL-18 protein activators, ADAM10 gene inhibitors, ADAM10 protein activity inhibitors, ADAM17 gene inhibitors, and ADAM17 protein activity inhibitors as an active ingredient, for treating subjects with HER2-positive cancers as well as having the copy number of MEL-18 gene, the mRNA expression level of the MEL-18 gene, and/or the expression level of MEL-18 protein, which are/is lower than predetermined value(s); and/or having or being expected to have drug resistance to HER2-targeted drugs.

In addition, the present invention relates to a pharmaceutical composition, which includes one or more selected from the group consisting of MEL-18 gene, MEL-18 gene expression activators, MEL-18 proteins, MEL-18 protein activators, ADAM10 gene inhibitors, ADAM10 protein activity inhibitors, ADAM17 gene inhibitors, and ADAM17 protein activity inhibitors as an active ingredient, for inhibiting or improving resistance to HER2-targeted drugs in subjects with HER2-positive cancers.

In addition, the present invention provides a pharmaceutical composition, which includes one or more selected from the group consisting of MEL-18 gene, MEL-18 gene expression activators, MEL-18 proteins, MEL-18 protein activators, ADAM10 gene inhibitors, ADAM10 protein activity inhibitors, ADAM17 gene inhibitors, and ADAM17 protein activity inhibitors, for assisting treatment of HER2+ cancer patients with HER2-targeted drugs.

All descriptions regarding the composition for companion diagnostics, the companion diagnostic method and the kit for companion diagnostics may also be applied mutatis mutandis to the pharmaceutical composition of the present invention.

The MEL-18 gene may be included in the composition in the form of a vector system including the MEL-18 gene, and the composition may be administered in the form of a gene therapeutic agent.

The MEL-18 gene expression activator may also be a protein, compound or nucleic acid molecule, which can promote the expression of the MEL-18 gene, or the nucleic acid molecule may be included in the composition in the form of a vector system.

The MEL-18 protein may be administered by itself, or administered in the form of a vector system including an mRNA sequence capable of encoding the protein. The MEL-18 protein activator may be a protein, compound or nucleic acid molecule which can promote the activity of the protein, and the nucleic acid molecule may be included in the composition while being included in a vector system in the form of a gene therapeutic agent. The implementation of the gene therapeutic agent or vector system may be carried out according to a method conventionally known in the technical field of the present invention.

In addition, the pharmaceutical composition of the present invention may include one or more selected from the group consisting of ADAM10 gene inhibitors, ADAM10 protein activity inhibitors, ADAM17 gene inhibitors, and ADAM17 protein activity inhibitors. When subjects with HER2-positive cancers, wherein subjects have the copy number of MEL-18 gene, the mRNA expression level of the MEL-18 gene, and/or the expression level of MEL-18 protein, which are/is lower than predetermined value(s); and/or subjects have or expected to have drug resistance to HER2-targeted drugs, are treated with ADAM10 gene inhibitors, ADAM10 protein activity inhibitors, ADAM17 gene inhibitors and ADAM17 protein activity inhibitors, or co-treated with an ADAM10/17 inhibitor and HER2-targeted drugs, resistance of the subject against HER2-targeted drugs may be inhibited, drug sensitivity and a therapeutic effect may be improved, and a prognosis may be improved. The ADAM10 gene and/or ADAM17 gene inhibitor inhibits the expression of ADAM10 and/or ADAM17 gene(s), and the inhibition includes all of prevention of transcription by regulating gene transcription, prevention of protein expression by inhibiting a process of translation from the mRNA of a gene to a protein, and degradation of a protein and/or mRNA itself. Therefore, the gene inhibitor includes an inhibitor of the expression of the mRNA of a gene and an inhibitor of the expression of a protein encoded by the gene.

The inhibitor may be one or more selected from the group consisting of an antisense nucleotide, microRNA (miRNA), small interfering RNA (siRNA), short hairpin RNA (shRNA), a compound and a protein, which complementarily bind to ADAM10, ADAM17, or ADAM10 and ADAM17 genes.

The ADAM10 or ADAM17 protein activity inhibitor may be one or more selected from the group consisting of a compound, a peptide, a peptide mimetic, an aptamer and an antibody, which specifically act on ADAM10, ADAM17, or ADAM10 and ADAM17 proteins. It is important that the present invention elucidate that resistance to HER2-targeted drugs varies according to the copy number/expression of the MEL-18 gene, and thus the drug resistance may be inhibited or improved by amplifying or activating MEL-18 to improve resistance of subjects with the loss or reduced expression or activity of the MEL-18 gene, or inhibiting the amplification, expression or activity of ADAM10 and/or ADAM17. Therefore, as the present invention newly reveals that resistance to HER2-targeted drugs may be improved or inhibited by inhibition of ADAM10 and/or ADAM17, and suggests a novel therapeutic approach that can be co-treated with HER2-targeted drugs, the ADAM10 and/or ADAM17 inhibitor(s) or activator(s) may be widely included in the present invention without limitation to a specific type of agent such as a compound, an antibody or the like.

In a specific example, the ADAM10 and/or ADAM17 protein activity inhibitor(s) may be one or more selected from the group consisting of INCB3619, INCB7839, WAY-022, TMI-2, CGS 27023, GW280264, INCB8765 and GI254023, but the present invention is not limited thereto.

INCB3619 and INCB7839 are dual inhibitors (Incyte Corporation, Wilmington, Del.), which can inhibit both ADAM10 and ADAM17, and WAY-022 (Wyeth-Aherst, Pearl River, N.Y.), TMI-2 or PF-5480090 (Pfizer) is an ADAM17 inhibitor. GI254023 is an ADAM10 inhibitor (Glaxo Smith Kline), and GW280264 is an ADAM10/ADAM17 inhibitor (Glaxo Smith Kline). Specific details of each of the above inhibitors can be found with reference to contents known in the technical field of the present invention, for example, those described in [Duffy et al, Clin Proteomics. 2011 Jun. 9; 8(1):9].

INCB3619 is methyl (6S,7S)-7-(hydroxycarbamoyl)-6-(4-phenyl-3,6-dihydro-2H-pyridine-1-carbonyl)-5-azaspiro[2.5]octane-5-carboxylate (Incyte), which may be represented by Formula 1 below and has CAS No. 791826-72-7. It is a dual inhibitor that can inhibit both ADAM10 and ADAM17. According to the present invention, when subjects without amplification of the MEL-18 gene or subjects with low expression of the MEL-18 gene are co-treated with INCB3619, resistance to HER2-targeted drugs may be improved, and a therapeutic effect of HER2-targeted drugs may be enhanced.

[Formula 1]

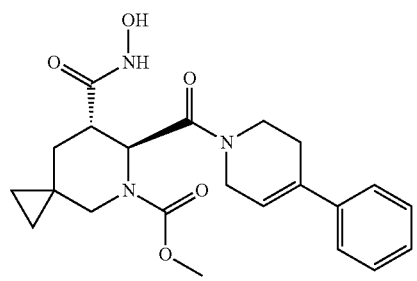

INCB7839, also called aderbasib, is (6S,7S)-7-[(hydroxyamino)carbonyl]-6-[(4-phenyl-1-piperazinyl)carbonyl]-5-azaspiro[2.5]octane-5-carboxylic acid methyl ester (Incyte), which is represented by Formula 2 below and has CAS No. 7918228-58-5. INCB7839 is also a dual inhibitor that can inhibit both of ADAM10 and ADAM17. Although it has been reported that INCB7839 improves a clinical therapeutic effect of Herceptin in a group of HER2+ metastatic breast cancer patients expressing p95-HER2, the clinical trial has been reported to have failed. However, according to the present invention, when subjects without amplification of the MEL-18 gene or subjects with low expression of the MEL-18 gene are co-treated with INCB7839 and HER2-targeted drugs, resistance to the HER2-targeted drug may be improved, and the therapeutic effect of the HER2-targeted drug may be enhanced.

[Formula 2]

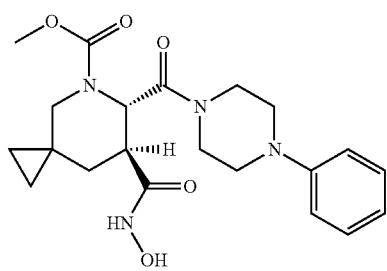

WAY-022 (Wyeth-Aherst, Pearl River, N.Y.) or TMI-2 (or PF-5480090; Pfizer) is an ADAM17-selected inhibitor, and PF-5480090 is represented by Formula 3 below. When an individual without the amplification of the MEL-18 gene or an individual with the low expression of the MEL-18 gene is treated with HER2-targeted drugs as well as WAY-022 or TMI-2 (PF-5480090) according to the present invention, resistance to HER2-targeted drugs may be improved, and the therapeutic effect of the HER2-targeted drug may be enhanced.

[Formula 3]

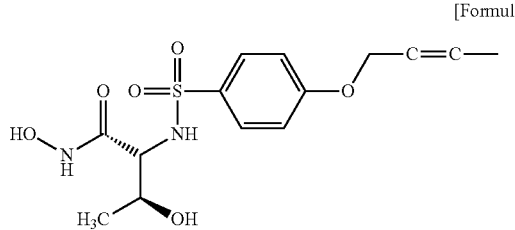

GW280264, also known as GW280264X, has a compound name of benzyl N-[(5S)-5-[[(2R,3S)-3-(Formylhydroxyamino)-2-(2-methylpropyl)-1-oxohexyl]amino]-6-oxo-6-(2-thiazolylamino)hexyl]-carbamate, which is represented by Formula 4 below and has CAS No. 866924-39-2. GW280264 may inhibit ADAM17. When an individual without amplification of the MEL-18 gene or an individual with low expression of the MEL-18 gene is co-treated with GW280264 as well as HER2-targeted drugs according to the present invention, resistance to the HER2-targeted drug may be improved, and the therapeutic effect of the HER2-targeted drug may be enhanced.

[Formula 4]

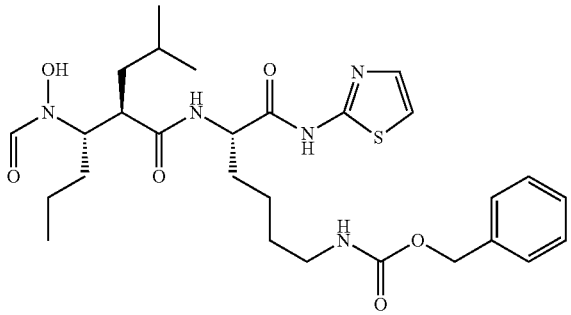

GI254023, also known as GI254023X, is (2R)—N-[(1S)-2,2-dimethyl-1-[(methylamino)carbonyl]-propyl]-2-[(1S)-1-[formyl(hydroxy)amino]ethyl]-5-phenylpentanamide, which may be represented by Formula 5 below. GI254023 is an ADAM10-selected inhibitor, and has about 100-fold selectivity to ADAM10 with respect to ADAM17. When an individual without amplification of the MEL-18 gene or an individual with low expression of the MEL-18 gene is co-treated with GI254023 as well as HER2-targeted drugs, resistance to the HER2-targeted drug may be improved, and a therapeutic effect of the HER2-targeted drug may be enhanced.

[Formula 5]

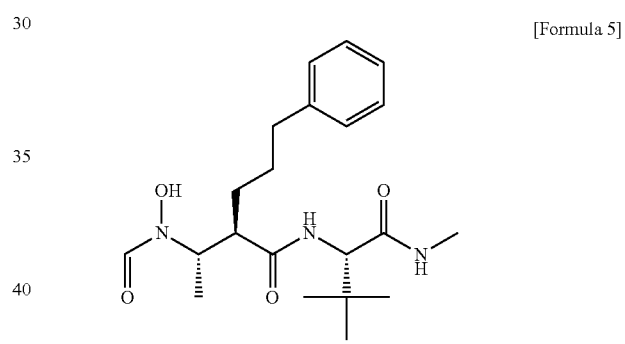

INCB8765 (Incyte Corporation) is a small molecule containing a hydroxamate moiety, which has a compound name of (1R,3S,4S)-3-[(hydroxyamino)carbonyl]-4-[(4-phenylpiperidin-1-yl)carbonyl]cyclohexyl pyrrolidine-1-carboxylate. INCB 8765 may inhibit ADAM10 via a zinc-binding mechanism. Accordingly, when an individual without amplification of the MEL-18 gene or an individual with low expression of the MEL-18 gene is co-treated with INCB8765 as well as HER2-targeted drugs according to the present invention, resistance to the HER2-targeted drug may be improved, and the therapeutic effect of the HER2-targeted drug may be enhanced.

In one exemplary embodiment of the present invention, when GW280264 inhibiting both ADAM10 and ADAM17 in a HER2+ breast cancer patient is co-administered with trastuzumab, it was confirmed that resistance to trastuzumab is improved and resistance induction is inhibited in MEL-18-depleted BT474 cells, resulting in improving an antitumor effect by trastuzumab. In addition, specific signaling systems for activities of MEL-18 and ADAM10/17 were confirmed.

In such an aspect, the composition of the present invention may be co-administered simultaneously or sequentially with HER2-targeted drugs.

The term "co-administration" or "co-treatment" used herein means administration of two or more types of drugs together. The co-administration includes simultaneous or sequential administration of two or more drugs. When the pharmaceutical composition of the present invention is administered in combination with the HER2-targeted drug, resistance induced by the inhibitor may be improved, the generation of resistance by the inhibitor may be inhibited, and the effect of a conventional therapeutic agent may also be improved.

The present invention also provides a composition for screening a drug that improves resistance to HER2-targeted drugs or is co-administered with HER2-targeted drugs, which includes one or more selected from the group consisting of MEL-18 gene, MEL-18 protein, ADAM10 gene, ADAM10 protein, ADAM17 gene or ADAM17 protein.

The present invention also provides a method of screening a drug for improving resistance to HER2-targeted drugs or which is co-administered with HER2-targeted drugs, which include: contacting candidate materials with one or more selected from the group consisting of MEL-18 gene; MEL-18 protein; ADAM10 gene; ADAM10 protein; ADAM17 gene and ADAM17 protein; and selecting a candidate increasing the copy number of the MEL-18 gene; the mRNA expression level of the MEL-18 gene; or the expression level of a protein expressed therefrom, or inhibiting the mRNA expression level of ADAM10 and/or ADAM17 gene(s) or the expression level of a protein expressed therefrom.

As described above, when the expression level of the MEL-18 gene or protein is improved or the ADAM10 and/or ADAM17 protein or gene is/are inhibited, the activation of ErbB signaling inducing resistance to HER2-targeted drugs may be inhibited, and thus a material promoting the expression level of the MEL-18 gene or protein or a material inhibiting the ADAM10 and/or ADAM17 protein or gene may be selected as a candidate material of a medicine for inhibiting or improving resistance to HER2-targeted drugs.

Confirmation of the reaction between a protein or mRNA and a candidate material may use conventional methods used to confirm protein-protein, protein-compound, DNA-DNA, DNA-RNA, DNA-protein, DNA-compound, RNA-protein, and RNA-compound reactions. For example, a hybridization test for confirming in vitro binding between the MEL-18 gene and a candidate material, a method of measuring the expression rate of the gene through Northern blotting following the reaction between mammalian cells and a test material, quantitative PCR or quantitative real-time PCR, a method of introducing the gene into cells by linking a reporter gene, reacting the gene with a test material, and then measuring the expression rate of a reporter protein, a method measuring activity after reacting the MEL-18 protein with a candidate material, yeast two-hybrid, searching for a phage-displayed peptide clone binding to the MEL-18 protein, high throughput screening (HTS) using natural substance and chemical libraries, drug hit HTS, cell-based screening, or a screening method using DNA array may be used.

The composition for screening may include distilled water or buffer which stably maintains the structure of a nucleic acid or protein, in addition to the active ingredient. In addition, the composition for screening may include, for an in vivo experiment, cells expressing MEL-18, or cells containing a plasmid expressing MEL-18 in the presence of a promoter capable of regulating a transcription rate. In addition, the composition for screening may further include Dvl according to a method of confirming the reaction between candidate materials, in addition to the active ingredient.

In the screening method of the present invention, a test material may be an individual nucleic acid, protein, extract, natural substance or compound which is assumed to have potential as a drug for inhibiting or improving resistance to HER2-targeted drugs according to a conventional selection method or randomly selected.

The present invention also provides a method of treating subjects with HER2-positive cancers, which includes administering a pharmaceutical composition including one or more selected from the group consisting of MEL-18 gene, MEL-18 gene expression activators, MEL-18 proteins, MEL-18 protein activators, ADAM10 gene inhibitors, ADAM10 protein activity inhibitors, ADAM17 gene inhibitors and ADAM17 protein activity inhibitors to subjects with HER2-positive cancers, wherein subjects have the copy number of MEL-18 gene, the mRNA expression level of the MEL-18 gene, and/or the expression level of MEL-18 protein, which are/is lower than predetermined value(s); and/or subjects have or expected to have drug resistance to HER2-targeted drugs.

All descriptions regarding the present invention may also be applied mutatis mutandis to the treating method described above.

The treating method may further include co-administering HER2-targeted drugs to subjects receiving administration of the pharmaceutical composition.

In addition, the treating method may further include measuring the copy number of the MEL-18 gene, the mRNA expression level of the MEL-18 gene, or the expression level of a protein encoded by the MEL-18 gene from a sample obtained from subjects with HER2-positive cancers before administration of the pharmaceutical composition. This step is for companion diagnostics for HER2-targeted drugs by measuring MEL-18 as a companion diagnostic marker for the HER2-targeted drug.

The administration may include all methods for oral administration or parenteral administration, and may be performed by a method conventionally used in the art to which the present invention belongs. In addition, in co-administration, a first drug may be administered by parenteral administration, a second drug may be administered by oral administration, and thus, the drugs may be administered through different routes.

In the present invention, when ADAM10 and 17 inhibitors are co-administered with trastuzumab to subjects with HER2+ breast cancer and having resistance to HER2-targeted drugs, it was confirmed through exemplary embodiments that resistance to trastuzumab is improved, and the therapeutic effect of trastuzumab is further enhanced.

In addition, the present invention provides a use of an agent for measuring the copy number of MEL-18 gene, the mRNA expression level of the MEL-18 gene, and/or the expression level of MEL-18 protein from a sample obtained from subjects with HER2-positive cancers for companion diagnostics for the HER2-targeted drug.

In addition, the present invention provides a use of an agent for measuring the copy number of MEL-18 gene, the mRNA expression level of the MEL-18 gene, and/or the expression level of MEL-18 protein to prepare a composition for diagnosing subjects with HER2-positive cancers, wherein subjects have the copy number of MEL-18 gene, the mRNA expression level of the MEL-18 gene, and/or the expression level of MEL-18 protein, which are/is lower than predetermined value(s); and/or subjects have or expected to have drug resistance to HER2-targeted drugs.

In addition, the present invention provides a use of an agent for measuring the copy number of MEL-18 gene, the mRNA expression level of the MEL-18 gene, and/or the expression level of MEL-18 protein to prepare a composition for companion diagnostics for HER2-targeted drugs for subjects with HER2-positive cancers, wherein subjects have the copy number of MEL-18 gene, the mRNA expression level of the MEL-18 gene, and/or the expression level of MEL-18 protein, which are/is lower than predetermined value(s); and/or subjects have or expected to have drug resistance to HER2-targeted drugs.

In addition, the present invention provides a use of an agent for measuring the copy number of MEL-18 gene; the mRNA expression level of the MEL-18 gene; or the expression level of MEL-18 protein from a sample obtained from subjects with HER2-positive cancers for preparing a kit for companion diagnostics for HER2-targeted drugs.

In addition, the present invention provides an application of one or more selected from the group consisting of MEL-18 gene, MEL-18 gene expression activators, MEL-18 proteins, MEL-18 protein activators, ADAM10 gene inhibitors, ADAM10 protein activity inhibitors, ADAM17 gene inhibitors and ADAM17 protein activity inhibitors to prepare drugs for treating subjects with HER2-positive cancers, wherein subjects have the copy number of MEL-18 gene, the mRNA expression level of the MEL-18 gene, and/or the expression level of MEL-18 protein, which are/is lower than predetermined value(s); and/or subjects have or expected to have drug resistance to HER2-targeted drugs.

All descriptions regarding the present invention may also be applied mutatis mutandis to the applications of the present invention.

Hereinafter, the present invention will be described in detail with reference to examples and experimental examples. The following examples and experimental examples are merely provided to exemplify the present invention, and are not intended to limit the scope of the present invention.

EXAMPLES

Materials and Experimental Methods

1. Fluorescence In Situ Hybridization

Primary human breast cancer acquired from 230 breast cancer patients (HER2-positive cases, n=54; HER2-cases, n=176) was used for experiments at Hanyang University Medical Center from January 2000 to December 2009 under the approval of the Institutional Review Board of Hanyang University.

To treat a protein-degradable slide before hybridization, a section was deparaffinated, air-dried, dehydrated and denatured in a 70% formamide-2×SSC solution at 74° C. for 5 minutes. The resulting section was hybridized with a selected DNA probe (PCGF2 FISH probe red 5-ROX dUTP, green 5-fluorescein dUTP chromosome 17 control probe; Empire Genomics, Buffalo, N.Y., USA) in a humid chamber at 37° C. overnight, washed, and counterstained with 0.2 μmol/L DAPI in a antifade solution. Gene signals per cell were evaluated in 50 tumor nuclei for each TMA core. The average gene copy number and the gene:CEP ratio were calculated separately for each core, and the gene was considered amplified when the average gene copy number was more than 6.0 (>6.0). Ambiguous cases were independently scored by two pathologists (SEL and WSK).

In addition, 213 HER2-positive invasive breast cancer tissues of patients receiving trastuzumab treatment and surgically resected at Konkuk University Medical Center from January 2010 to December 2016 were enrolled under the approval of the Institutional Review Board of Konkuk University Medical Center (Seoul, Korea) for experiments. Consent had been previously acquired from the patients. After manufacturing tissue microarrays, sections were deparaffinated, dehydrated and denatured. After overnight hybridization at 37° C. in a humid chamber with DNA probes (PCGF2 FISH probe red 5-ROX dUTP, green 5-fluorescein dUTP chromosome 17 control probe; Empire Genomics, Buffalo, N.Y., USA), the slides were counterstained with 0.2 μmol/L DAPI. Gene signals per cell were evaluated in 50 tumor nuclei for each case: the average gene copy number and the gene: CEP ratio were separately calculated for each nucleus, and the tumor was considered amplified when the average gene copy number was higher than 6.0.

2. Cell Culture and Drugs

All cells were purchased from American Type Culture Collection (ATCC, Manassas, Va., USA). Human breast cancer cells were cultured in an RPMI-1640 medium (Welgene, Daegu, Korea) containing 10% fetal bovine serum (FBS). The 293T cells were cultured in DMEM (Welgrene) supplemented with 10% FBS. All cells were incubated at 37° C. in a humidified 5% $CO_2$ incubator. Trastuzumab (Herceptin) was purchased from Roche (Basel, Switzerland), and GW280264 was obtained from Aobious (Gloucester, Mass., USA).

3. Antibodies

Antibodies used in the experiments of the present invention were commercially purchased: MEL-18(H-115, sc-10744X), phospho-EGFR(Tyr1173, sc-12351), EGFR (1005, sc-03), HER2(3B5, sc-33684)(H-224, sc-9001), HER3(C-17, sc-285), HES1(H-140, sc-25392), RING1B(N-32, sc101109), Polymerase II(H-224, sc-9001), normal mouse IgG(sc-2025), normal rabbit IgG(sc-2027), goat anti-mouse IgG-HRP(sc-2005), goat anti-rabbit IgG-HRP(sc-2030), and donkey anti-goat IgG-HRP(sc-2020) were purchased from Santa Cruz Biotechnology (Santa Cruz, Calif., USA); beta-actin(C4, MAB1501R), phospho-HER2 (Tyr1248, 06-229), H3ac(06-599), and H3K27me3(07-499) were purchased from Merck Millipore (Billerica, Mass., USA); phospho-HER3(Tyr1289, 4791S), phospho-AKT (D9E, 4060S), AKT(92725), EZH2(D2C9, 5246S), and H2AK119ub(D27C4, 8240S) were purchased from Cell Signaling Technology (Beverly, Mass., USA); CBX7 (ab21873) and ADAM10(ab1997) were purchased from Abcam (Cambridge, UK); and ADAM17 (C2C3, GTX101358) was purchased from GeneTex (Irvine, Calif., USA).

4. Production of Stable Cells

To establish MEL-18-overexpressing cell lines, 293T cells were co-transfected with pLVX-MEL-18 or an empty vector construct using the Lipofectamine 2000 reagent (Invitrogen, Carlsbad, Calif., USA) as described in [J. Y. Lee et al, *J Clin Invest* 125, 1801-1814(2015)] (15). After 60 hours of transfection, the medium containing the lentiviruses was harvested, and transduced into target cells using 6 μm/ml polybrene (Sigma-Aldrich). To establish MEL-18-knockdown cell lines, lentiviruses encoding a GIPZ Human Lentiviral MEL-18 shRNA Clone Gene Set (RHS4531-EG7703-V3LHS334758; 5'-AGACAAUGUCUUGAAGUGU-3'; SEQ ID NO: 25) were purchased from GE Dharmacon (Lafayette, Colo., USA), generated, and then infected into cells as described above.

5. Cell Viability Test

An in vitro toxicity test analysis kit (Sulforhodamine B based, TOX6) was purchased from Sigma-Aldrich (St. Louis, Mo., USA), and used according to the manufacturer's protocols. Cells (3×10³ cells/well) were cultured in a RPMI 1640 medium (Welgene) supplemented with or without 10 μm/ml trastuzumab, 1 μM GW280264, PBS and DMSO in a 96-well cell culture plate, and after three days, the medium was exchanged for fresh medium containing a drug. After five days, the cells were fixed by layering a TCA solution in the medium, and incubated at 4° C. for 1 hour. The fixed cells were washed with water several times, and stained with a 0.4% sulforhodamine B solution for 30 minutes. Subsequently, the stained cells were washed with a 1% acetic acid solution until remaining salts were no longer observed, and the incorporated dye was dissolved in a 10 mM Tris solution while gently stirring. The prepared plate was detected using a microplate reader at 490 nm.

6. Colony Formation Assay

Cells (1×10⁴ cells/well) were treated with or without 10 μm/ml trastuzumab, 1 μM GW280264 and vehicles for 1 week in a 24-well cell culture plate, and the medium was exchanged for a fresh medium every 3 days. After 2 weeks, the cells were fixed with a 4% formaldehyde solution for 5 minutes, washed with PBS, and stained with 0.02% crystal violet (C0775, Sigma-Aldrich) for 1 to 2 hours at room temperature and then washed again. The prepared plates were dried thoroughly, and the experiment was carried out.

7. Real-Time Quantitative PCR

Total RNA was isolated using the TRIzol reagent (Invitrogen) and reverse transcription-PCR (RT-PCR) was performed with an Access RT-PCR system (Promega, Madison, Wis., USA) according to the manufacturer's instructions. To measure a RNA expression level, quantitative RT-PCR (qRT-PCR) was performed using an Applied Biosystems 7300 Real-Time PCR system using SYBR Green dye (Applied Biosystems, Foster City, Calif., USA) as described in the manufacturer's instructions. Data was normalized with GAPDH expression.

Primers used in this experiment are as follows:

```
MEL-18,
                              (SEQ ID NO: 1)
5'-GTACTTCATCGACGCCACCACTATC-3'
and
                              (SEQ ID NO: 2)
5'-CTCGTCCTCGTACAGAACCTCCA-3';

ADAM10,
                              (SEQ ID NO: 3)
5'-GCTACGGGCACAAGTGACTA-3'
and
                              (SEQ ID NO: 4)
5'-AGACGTAAGCAGAAACCAGACA-3';

ADAM17,
                              (SEQ ID NO: 5)
5'-AGCTCCAAAACTGGACCACC-3'
and
                              (SEQ ID NO: 6)
5'-GCTGCTATTTGGGAAGGGGT-3';

BCL-2,
                              (SEQ ID NO: 7)
5'-GAGACAGCCAGGAGAAATCA-3'
and
                              (SEQ ID NO: 8)
5'-CCTGTGGATGACTGAGTACC-3';

TGF-alpha,
                              (SEQ ID NO: 9)
5'-TCAGTCAATTTGGCCGGGAT-3'
and
                              (SEQ ID NO: 10)
5'-GGGCAGGTTGGAAGAGATCA-3';

S100A9,
                              (SEQ ID NO: 11)
5'-ACACATCATGGAGGACCTGG-3'
and
                              (SEQ ID NO: 12)
5'-TCACCCTCGTGCATCTTCTC-3';

IGFBP3,
                              (SEQ ID NO: 13)
5'-AACTGTGGCCATGACTGAGG-3'
and
                              (SEQ ID NO: 14)
5'-AGTCTCCCTGAGCCTGACTT-3';

MDK,
                              (SEQ ID NO: 15)
5'-CTCCCGGAAAGGCACTGG-3'
and
                              (SEQ ID NO: 16)
5'-CACCTGGGGCGGTTTCC-3';

CMTM3,
                              (SEQ ID NO: 17)
5'-GTATCTGGGCAGCAGGTGTT-3'
and
                              (SEQ ID NO: 18)
5'-ACCAAGTGCAGACAAACCCA-3';

RALGAPA2,
                              (SEQ ID NO: 19)
5'-CACTCGAATGCCGTCAGACT-3'
and
                              (SEQ ID NO: 20)
5'-TGCGGTAGTCTCTGGAGTGT-3';

USP48,
                              (SEQ ID NO: 21)
5'-GGCCGTCTGTCTCTTGGTATT-3'
and
                              (SEQ ID NO: 22)
5'-TGCACCAAAGCAAAAAGCCT-3'
and GAPDH,
                              (SEQ ID NO: 23)
5'-GAAGGTGAAGGTCGGAGTC-3'
and
                              (SEQ ID NO: 24)
5'-GAAGATGGTGATGGGATTTC-3'.
```

8. Immunoblotting and Immunoprecipitation

Cells were lysed in RIPA buffer, and the lysates were subjected to immunoblotting and immunoprecipitation as described in [M. H. Cho et al, Nat Commun 6, 7821(2015)] (60). For immunoblotting, the cell lysates were separated by 6% to 15% SDS-polyacrylamide gel electrophoresis (PAGE) and transferred to nitrocellulose membranes. After blocking the membranes with 5% skin milk, the membranes were incubated with primary antibodies overnight at 4° C., and then reacted with horseradish peroxidase (HRP)-conjugated secondary antibodies for 1 hour at room temperature. Bands were visualized using an ECL detection system (GE Healthcare, Chalfont St. Giles, UK).

For immunoprecipitation, cell lysates (1 to 3 mg) were incubated with suitable antibodies (1 μm) overnight at 4° C. The samples were incubated again with protein agarose A or G (20 μL) for 2 hours at 4° C. and washed with pre-cooled PBS three times, and then 20 μL of β-mercaptoethanol-added 5× sample loading buffer was added to immunoprecipitated pellets. The samples were heated at 95° C. for 5 minutes, and then SDS-PAGE and immunoblotting were performed as described above.

9. Gene Expression Microarray Assay

To analyze different gene expression profiles between a control and MEL-18-knockdown BT474 cells, gene expression microarrays were performed as described in [J. Y. Lee et al, *J Clin Invest* 125, 1801-1814(2015)] according to the manufacturer's instructions using a HumanHT-12 v4 Expression BeadChip (Illumina). Total RNA was isolated from the cells, cDNA and biotinylated cRNA were generated using an Illumina Total Prep RNA amplification kit (Ambion). cRNA was hybridized on a HumanHT-12 v4 Expression BeadChip (Illumina), and then the chip was washed, dried and scanned with a bead array reader. Raw data was obtained using GenomeStudio version 2011.1 software (Illumina), and a call of presence/absence relied on a classification method based on detection P values (gene probes with detection P values of less than 0.05, present; all other genes, absent). The selected gene probe signal values were logarithmically transformed, and normalized using the quantile method. All gene probes displaying absolute fold changes of 1.5 or more between comparative controls were considered differentially expressed. The functional analysis of differentially expressed genes was performed using databases for Visualization and Integrated Discovery (DAVID) (61, 62) and Gene Set Enrichment Analysis (GSEA) (63, 64).

10. Use of Public Data

Two publicly available datasets, TCGA (37) and METABRIC (38), of human breast cancer patients were downloaded and analyzed through cBioportal (65, 66), and re-analyzed with the Python and R programming packages. The Cancer Cell Line Encyclopedia (CCLE) dataset was analyzed through cBioportal. A clinical dataset (GSE55348)(68, 69) for HER2+ breast cancer treated with adjuvant trastuzumab was downloaded from the GEO database (www.ncbi.nlm.nih.gov/geo), and re-analyzed (Probe ID used: PCGF2, ILMN_1809859; ADAM10, ILMN_1718946; ADAM17, ILMN_1765779). For the analysis of the relationship between MEL-18 amplification/mRNA expression and the OS and DFS of breast cancer patients, the Kaplan-Meier estimation method was used. A public dataset (GSE67868) (67) of Mel-18 ChIP-seq in mouse embryonic stem cells was obtained from GEO for re-analysis of MEL-18 protein-binding genes.

11. Chromatin Immunoprecipitation (ChIP) Assay

A ChIP assay was performed as described in [M. H. Cho et al, *Nat Commun* 6, 7821(2015)] (60). Cells were cross-linked with 1% formaldehyde at room temperature for 10 minutes, lysed in 200 μL of SDS lysis buffer, and sonicated using a Bioruptor (Cosmo Bio Co. Ltd, Tokyo, Japan). The cell lysate was incubated with specific antibodies overnight at 4° C., and then incubated with protein A- or G-agarose coupled to salmon sperm DNA (Millipore) for additional 2 hours. The immunoprecipitates were washed, eluted and reverse-crosslinked with 20 μL of 5M NaCl at 65° C. overnight. DNA fragments precipitated from the eluate were used for real-time quantitative PCR (qPCR) to analyze the intensity of a ChIP signal.

ChIP-qPCR was performed using the following specific primers: ADAM10 primer, 5'-GCTCGGAAAATTACATCTCGGAC-3' (SEQ ID NO: 26) and 5'-GCCCCAGTGATGCGAACATA-3' (SEQ ID NO: 27); and ADAM17 primer, 5'-GCCGCTTTCTACAGCTCCTTT-3' (SEQ ID NO: 28) and 5'-GCCTCCTTTGTCTTGATGCC-3' (SEQ ID NO: 29).

12. Phospho-Receptor Tyrosine Kinase (RTK) Assay

Kinase activity was detected in an RTK panel using a human phospho-RTK array kit (R&D Systems). Cells were harvested according to the manufacturer's protocol, washed with cold PBS and lysed with lysis buffer, and then a 100 to 200 μg lysate was incubated with a blocked membrane overnight at 4° C. The membrane was exposed to a chemiluminescent reagent, an image was captured, and quantification was performed using AlphaEaseFC software (Alpha Innotech, Inc., San Leandro, Calif., USA).

13. Enzyme-Linked Immunospecific assay (ELISA)

The levels of the HER ligands HB-EGF and heregulinl (heregulinl, NRG1-beta1, NRG1) were measured in cell culture supernatants using ELISA (BosterBio and R&D Systems) according to the manufacturer's protocols.

In the case of the R&D Systems kit, an ELISA plate was coated overnight with captured antibodies and blocked with 3% BSA for 1 hour. Subsequently, 100 μL of samples and standards were loaded, and the plate was maintained at room temperature for 2 hours. The plate wells were washed and incubated with detection antibodies for 2 hours, and then incubated with streptavidin labeled with horseradish peroxidase for 20 minutes.

In the case of the BosterBio ELISA kit, the antibody-coated plate was directly filled with samples and standards, and incubated for 90 minutes. Subsequently, the samples were removed, and the plate was incubated with biotinylated anti-human HB-EGF antibodies for 60 minutes and washed. The plate was incubated with an ABC solution for 30 minutes and washed. After this step, the plates for both kits were filled with a substrate solution for 20 minutes, the reaction was stopped using a stop solution for 20 minutes, and the absorbance was measured using a microplate reader at a wavelength of 450 nm. Each incubation for the BosterBio ELISA kit was performed at 37° C.

14. Mouse Xenograft Model

All animal experiments were approved by the Hanyang University Animal Care and Use Committee (Seoul, Korea). Four-week-old female NOD/SCID mice were purchased from Koatech (Pyeongtaek, Gyeonggi). For orthotopic xenografts, control and MEL-18-knockdown BT474 cells ($2 \times 10^6$) were resuspended in 150 uL of a 1:1 mixture of PBS/Matrigel, and directly injected into breast fat pads of the mice (left, control; right, MEL-18 shRNA). One day before the cell injection into the mice, estradiol pellets (0.72 mg, 60-day release; Innovative Research of America, Sarasota, Fla., USA) were provided. After a tumor size reached 100 mm$^3$, the mice were treated twice weekly with either a vehicle (PBS) or trastuzumab (20 mg/kg) by intraperitoneal injection. The tumor size was measured twice weekly, and the mice were monitored daily for clinical signs of toxicity during a treatment period.

The tumor size was calculated as follows: Volume (mm$^3$)=(a×b$^2$)/2, wherein a is the largest diameter, and b is a vertical diameter.

15. Immunohistochemistry

Formalin-fixed and paraffin-embedded tumor sections from xenografted mice were deparaffinized, rehydrated, and immunostained with suitable primary antibodies against MEL-18 (1:25), Ki-67 (1:150), ADAM10 (1:100), and ADAM17 (1:100) using an automated system, Leica Bond III (Leica Biosystems, Nusslock, Germany) with a Bond Polymer Refine Detection Kit (Leica Biosystems). Expression was graded according to the intensity and percentage of positive staining of tumor cells as follows: Intensity, 0 (no staining), 1 (weak), 2 (moderate) and 3 (strong); 0 (0%-5%), 1 (6%-25%), 2 (26%-50%), 3 (51%-75%) and 4 (>75%); the extent of staining, 0 (0%-5%), 1 (6%-25%), 2 (26%-50%), 3 (51%-75%), and 4 (>75%). To obtain a combined immunoreactive score (IRS), the score for intensity was multiplied by the score for extent. For survival analysis of breast cancer patients treated with trastuzumab (n=213) according to ADAM10 or ADAM17 expression, immunohistochemical analysis was performed as described above. When the intensity score was 2 or more, the expression status was considered positive.

16. Statistical Analysis

The statistical significance of the difference between a control and an experimental group was determined using the two-tailed Student's t-test. For multiple group comparison, following Welch ANOVA, a post-hoc LSD test for equal variances following non-equal distribution or one-way ANOVA was performed with the Dunnett's T3 test. Pearson's correlation was used for analysis of the correlation between MEL-18 expression and its amplification or HER2 expression. The Kaplan-Meier curves for OS and DFS analyses were evaluated using a long-rank test. These analyses were performed using SPSS software (ver. 12.0), the Python statistical package (https://www.python.org/) and the R statistical package (http://www.r-project.org/) or the Excel (Microsoft, Redmond, Wash., USA) software package. In all cases, P values of less than 0.05 (P value<0.05) were considered statistically significant.

Experimental Examples: Results

1. Clinical Meaning of MEL-18 Amplification in HER2-Positive Breast Cancer

Previous studies of the inventors have supported various tumor suppressive functions of MEL-18 in human breast cancer (4, 11-15), and indicate that MEL-18 loss is indicative of aggressive phenotype acquisition in breast cancer. To further define the significance of MEL-18 expression in human cancer, the genetic abnormality of PCGF2, which is a gene encoding MEL-18 located at 17q21 in breast cancer, and the genetic aberration of the MEL-18 gene were investigated in multiple breast cancer cohorts. In the Cancer Genome Atlas (TCGA; 37) and METABRIC datasets (38), there were low rates of deletion and no somatic mutations found in the MEL-18 gene, and in basal-like breast cancer, downregulation of a MEL-18 mRNA level was consistent with the previous studies (15) (FIG. 1A). Notably, the amplification of the MEL-18 gene occurred exclusively in HER2-amplified breast cancer, accounting for approximately half (FIG. 1A and Table 1).

TABLE 1

| Cohorts | HER2 expression | MEL-18 expression | |
|---|---|---|---|
| | | Positive | Negative |
| HYU (n = 230) | Positive (n = 54) | 23 cases (42.6%) | 31 cases (57.4%) |
| | Negative (n = 176) | 0 case (0%) | 176 cases (90%) |
| TCGA (n = 817) | Positive (n = 105) | 47 cases (44.8%) | 58 cases (55.2%) |
| | Negative (n = 712) | 2 cases (6%) | 710 cases (94%) |

TABLE 1-continued

| Cohorts | HER2 expression | MEL-18 expression | |
|---|---|---|---|
| | | Positive | Negative |
| METABRIC (n = 1980) | Positive (n = 298) | 146 cases (49.0%) | 152 cases (51.0%) |
| | Negative (n = 1682) | 4 cases (0.2%) | 1678 cases (99.8%) |

Figure 1B:
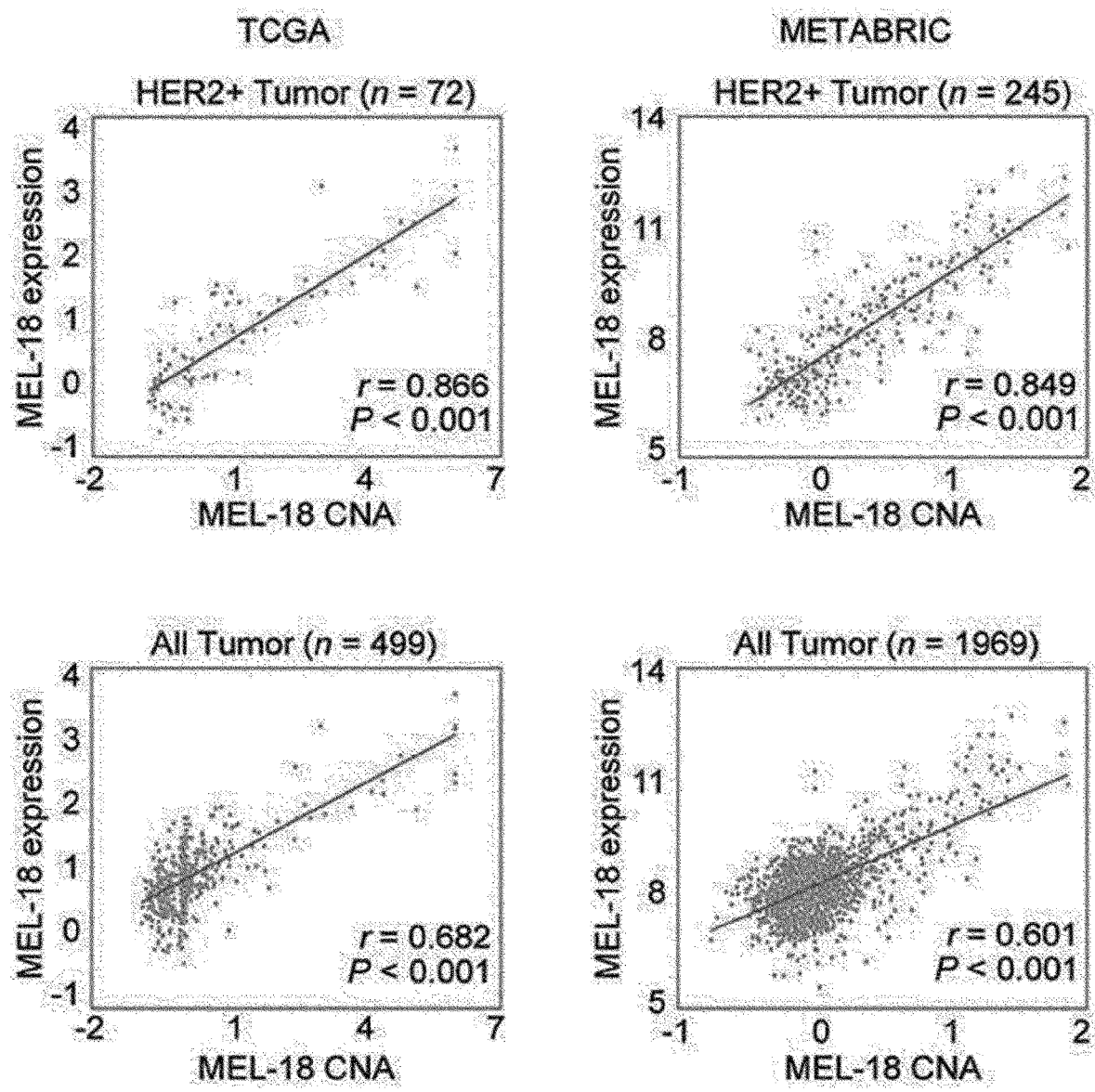
FIG. 1B shows that MEL-18 is associated with positive survival results in HER2+ breast cancer, and scatterplots showing the correlation between MEL-18 expression and amplification in the indicated datasets. The r value was calculated through Pearson's correlation coefficient analysis.
Figure 1C:
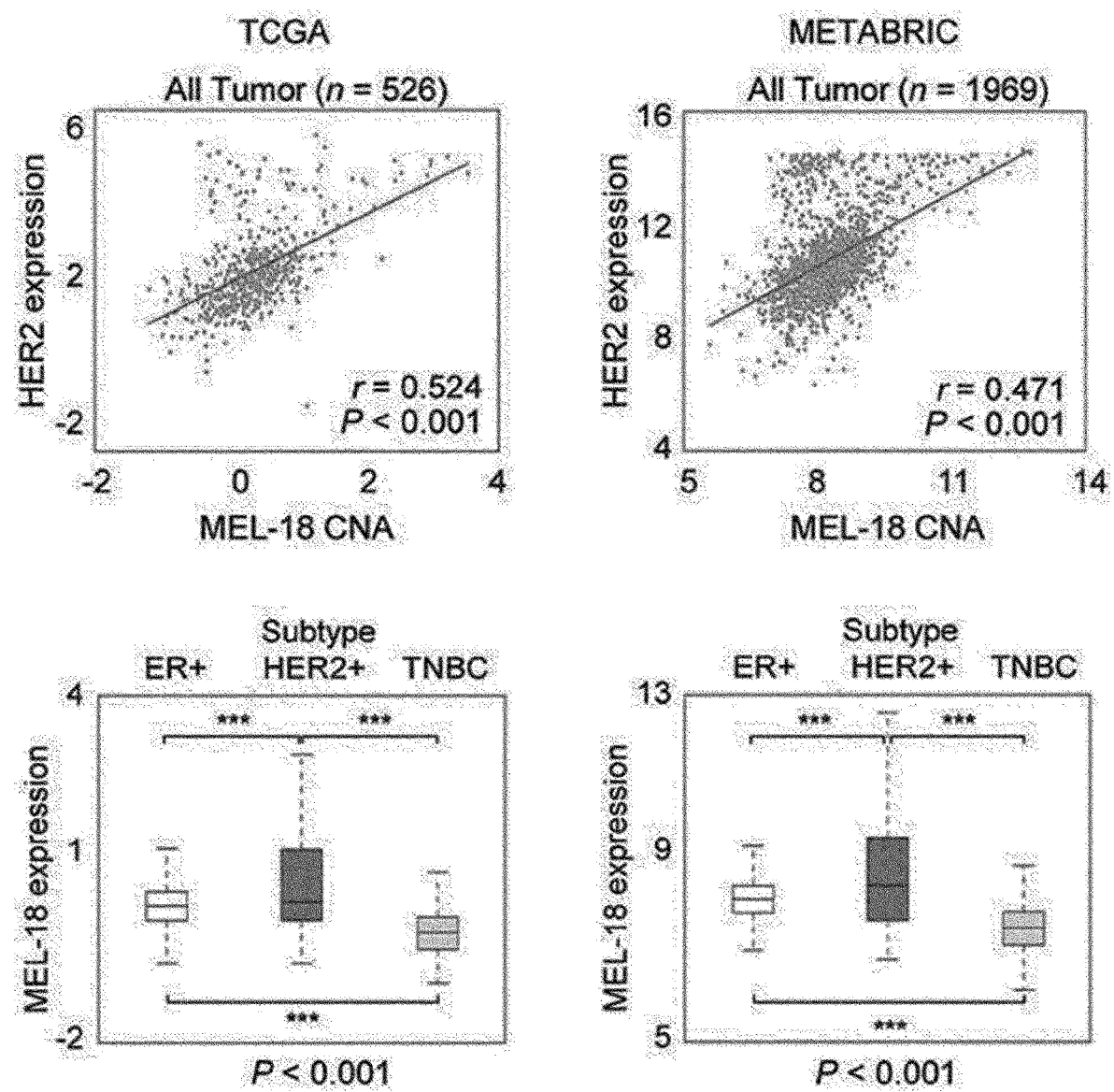
FIG. 1C shows that MEL-18 is associated with positive survival results in HER2+ breast cancer, and scatterplots showing the correlation between MEL-18 expression and HER2 expression (top) and boxplots of MEL-18 expression levels in different breast cancer subtypes from the indicated datasets (bottom). Based on one-way ANOVA, ***$P<0.001$.
Figure 1D:
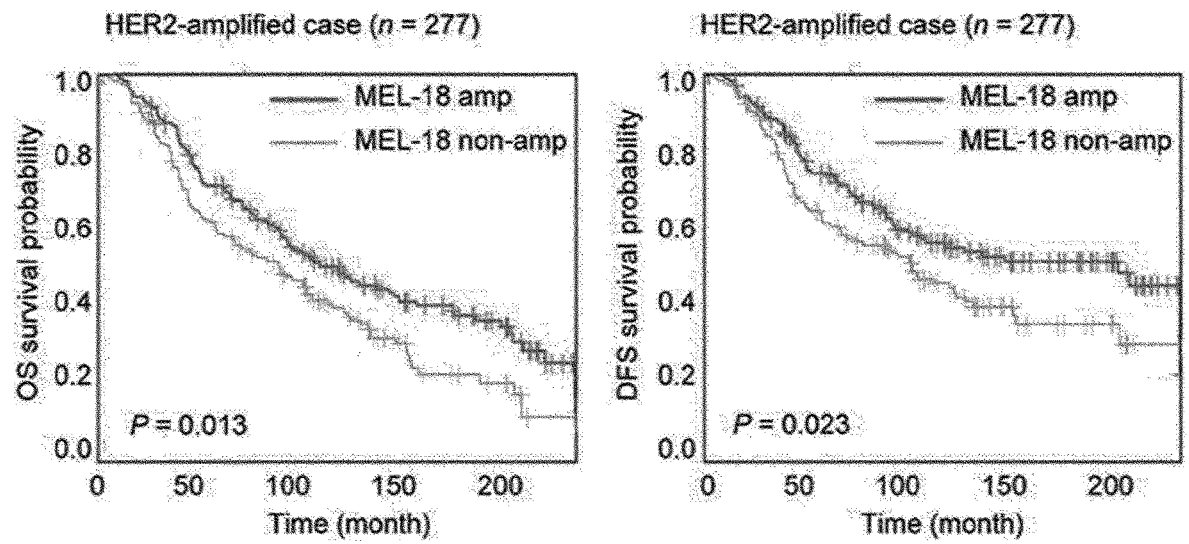
FIG. 1D shows that MEL-18 is associated with positive survival results in HER2+ breast cancer, and graphs showing OS and DFS analysis results relative to MEL-18 amplification among 277 HER2-amplified breast cancer cases from METABRIC. Data was analyzed using the Kaplan-Meier method with the log-rank test.
Figure 1E:
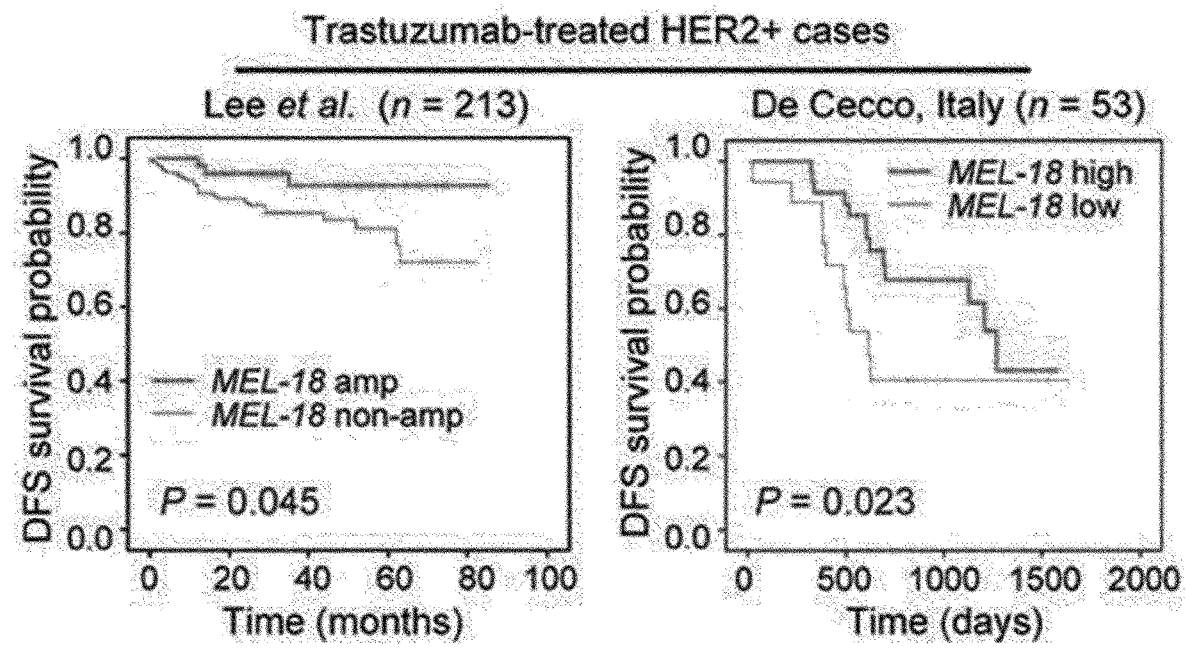
FIG. 1E shows DFS (disease-free survival) analysis of breast cancer cases treated with trastuzumab (left, clinical cohort, n=213; right, GSE55348, n=53) according to MEL-18 amplification (left) or mRNA expression (right). GSE55348 (cohort from GEO) was divided into two groups according to the $66^{th}$ percentile of MEL-18 expression (high, >66%; low, <33%). Data was analyzed using the Kaplan-Meier method (left) or Gehan-Breslow-Wilcoxon test (right) with the log-rank test.
Figure 7A:
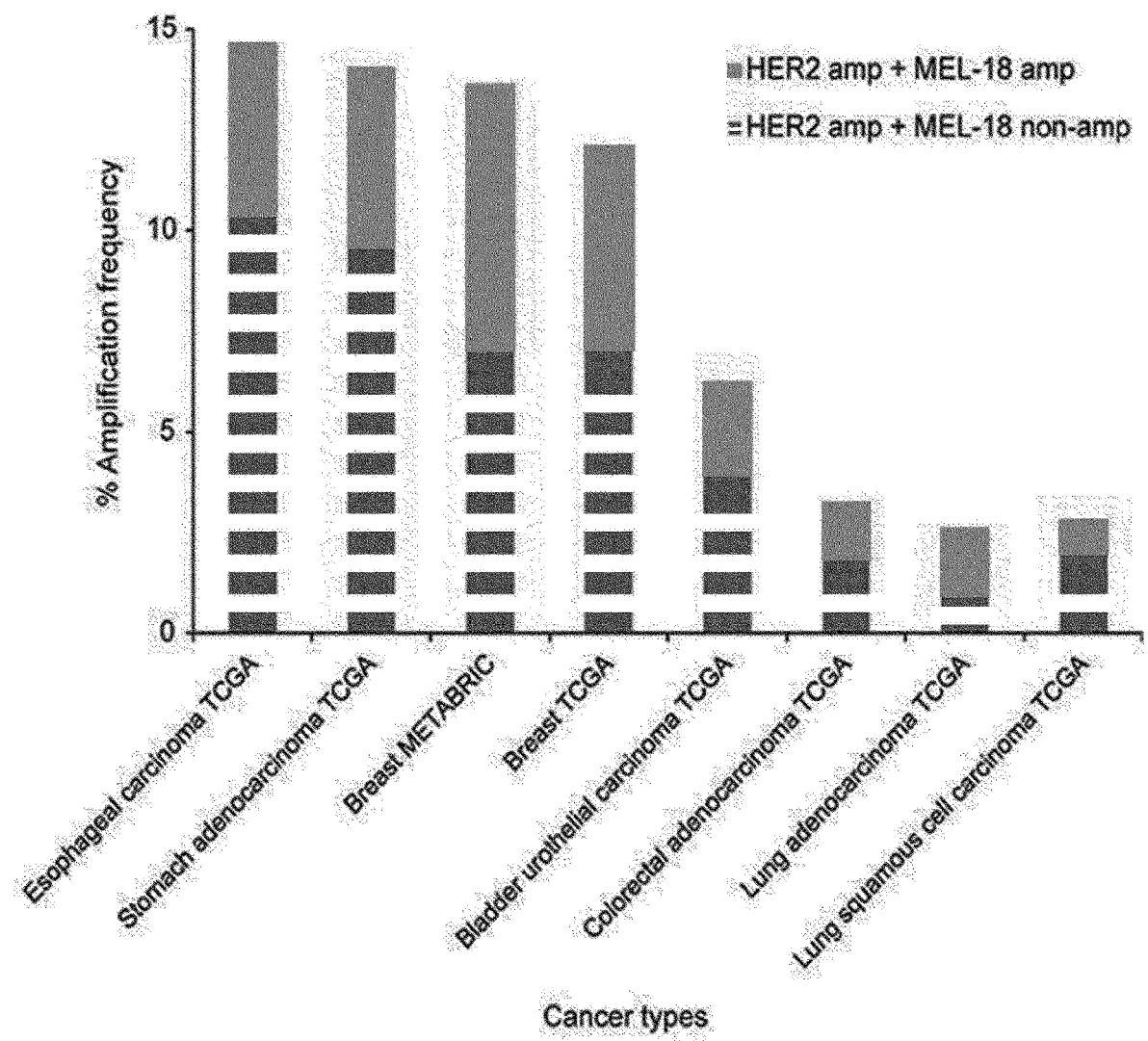
FIG. 7A shows MEL-18 amplification patterns in various types of human cancer according to an exemplary embodiment of the present invention, and graphs showing the percentage of MEL-18 amplification in HER2 amplification cases of various cancer type public datasets. Here, amp represents an amplified case; and non-amp represents a non-amplified case.
Figure 7B:
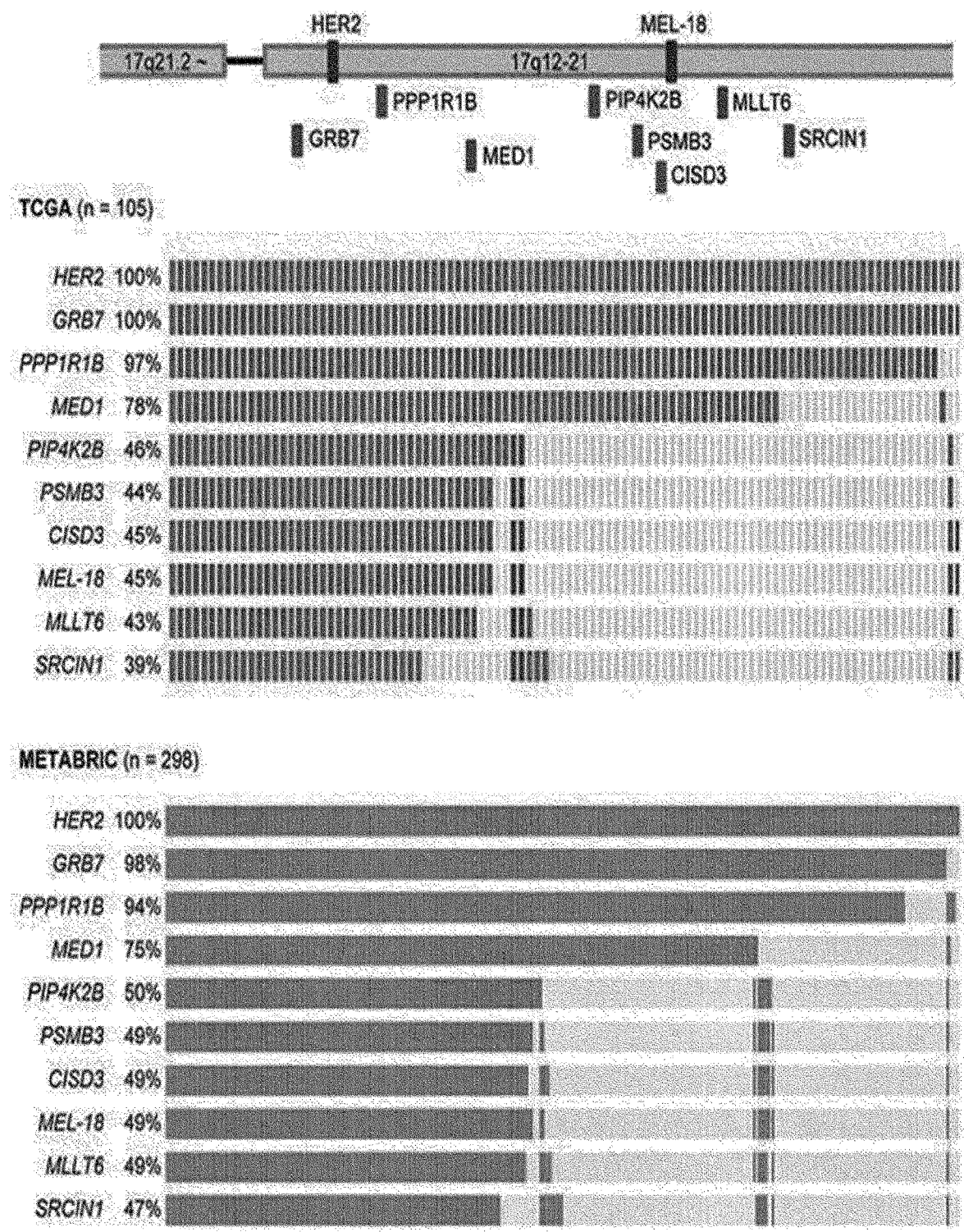
FIG. 7B shows MEL-18 amplification patterns in various types of human cancer according to an exemplary embodiment of the present invention, and graphs showing the co-amplification percentage of different genes located in a 17q12-21 amplicon with HER2 gene and distances from the HER2 gene locus.

In FISH analysis of the cohorts, almost a half of the HER2-positive breast cancer patients exhibited MEL-18 amplification (FIG. 1A). Other than breast cancer, according to HER2-positive status, similar rates of MEL-18 amplification occurred in other types of cancer (FIG. 7A). The frequency of the MEL-18 gene amplification in the 17q12-21 amplicon was dependent on the distance from the HER2 gene (FIG. 7B). From TCGA and METABRIC datasets, it was confirmed that MEL-18 gene amplification was closely associated with the increased MEL-18 mRNA expression level in breast cancer patients (FIG. 1B). In addition, the positive correlation between MEL-18 and HER2 expression was confirmed from these cohorts (FIG. 1C), and MEL-18 expression was higher in the HER2 subtype, compared to other subtypes (FIG. 1C). In the survival analysis of HER2-positive breast cancer patients using METABRIC datasets, MEL-18-amplified patients had much higher overall survival (OS) and disease-free survival (DFS) rates (P=0.013 and P=0.023, respectively; FIG. 1D). In addition, MEL-18 amplification or high MEL-18 expression was associated with favorable DFS in patients receiving trastuzumab treatment. Collectively, such result supported the clinical significance of MEL-18 in HER2-positive breast cancer as an indicator of a favorable survival outcome associated with a response to anti-HER2 therapy.

2. MEL-18 Amplification-Induced Trastuzumab Sensitivity in HER2-Positive Breast Cancer Based on previous studies supporting the role of MEL-18 knockdown in the regulation of CSC and EMT associated with resistance to an anticancer agent (13, 14), MEL-18 is likely to be involved in a response to trastuzumab, and is estimated to affect the prognosis of HER2-positive breast cancer. To confirm this, an experiment was performed.

Figure 2A:
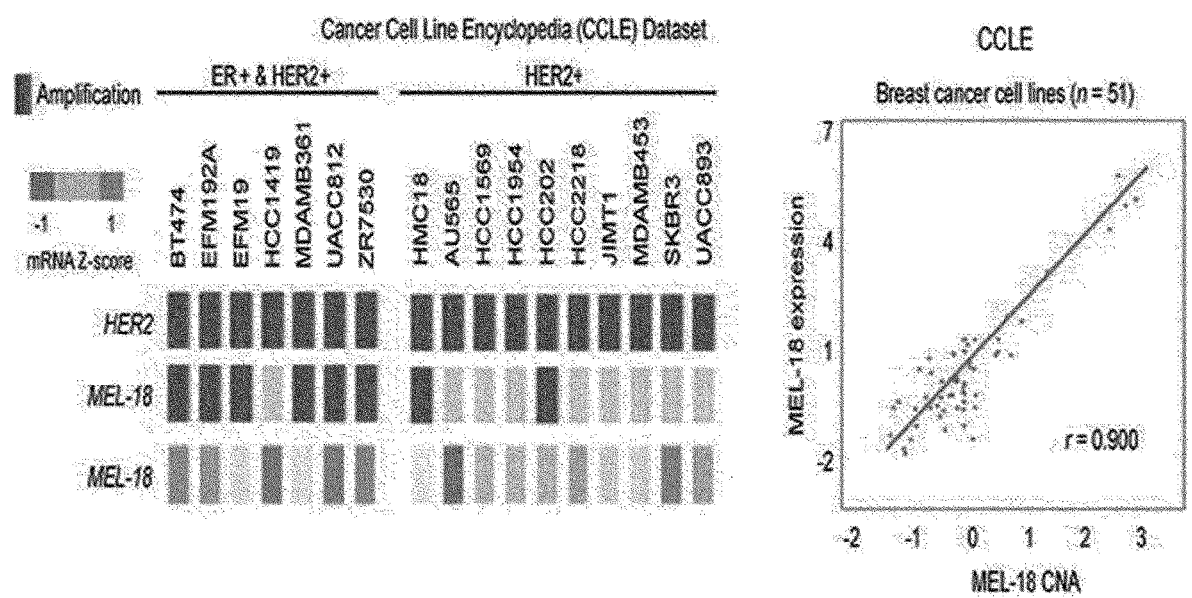
FIG. 2A shows the result confirming that MEL-18 inhibition induces trastuzumab resistance in HER2+ breast cancer according to an exemplary embodiment of the present invention, in which the data shows MEL-18 amplification and expression in HER2-amplified breast cancer cell lines (left) and a scatterplot shows the correlation between MEL-18 expression and amplification, obtained by the Pearson's correlation coefficient analysis (right).
Figure 2B:
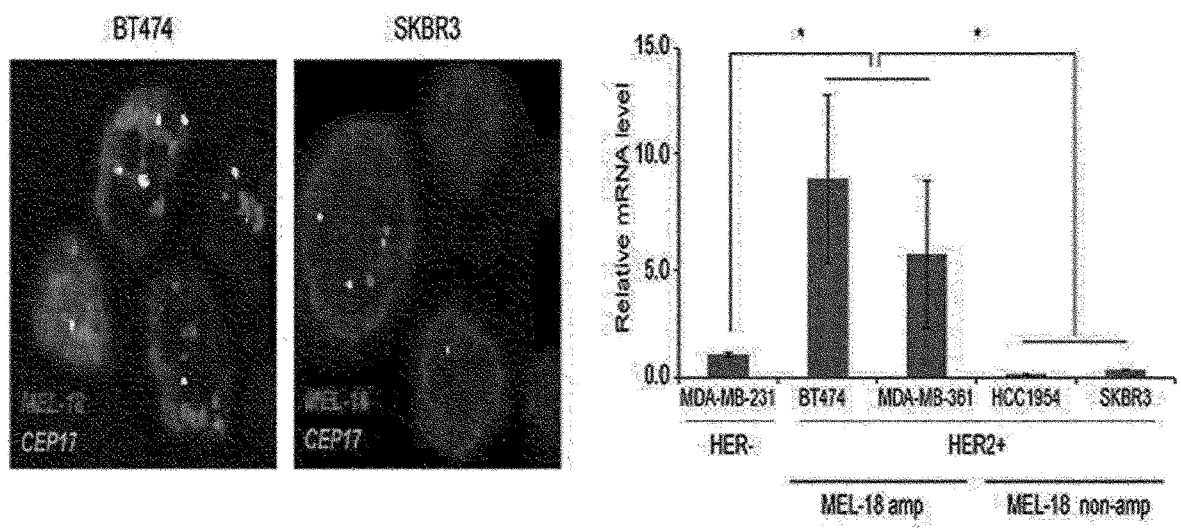
FIG. 2B shows the result confirming that MEL-18 inhibition induces trastuzumab resistance in HER2+ breast cancer according to an exemplary embodiment of the present invention, in which an image of the MEL-18 amplification status measured by FISH in each type of breast cancer cell lines (BT474, SKBR3) (left), and MEL-18 mRNA levels in respective breast cancer cell lines (BT474, MDA-MB-361, HCC1954 and SKBR3) (right; mean±SD (n=3), *$P<0.05$ (Welch's ANOVA)) are shown.

To confirm the functional relevance of MEL-18 amplification in HER2-positive breast cancer, genetic variation and mRNA levels of MEL-18 were examined in various types of HER2-positive breast cancer cell lines. Half of HER2-positive cell lines in the Cancer Cell Line Encyclopedia (CCLE) dataset, consistent with clinical data, exhibited MEL-18 amplification and mRNA expression correlated therewith, which is the same as confirmed by FISH and qRT-PCR analysis (FIG. 2A and FIG. 2B).

Afterward, in respective various MEL-18-amplified and MEL-18-nonamplified, HER2-positive breast cancer cell lines (BT474, ZR-75-30, SKBR2 and HCC-1419), lentiviral MEL-18 knockdown and overexpression systems (FIG. 2C), and responses of these cells to trastuzumab treatment were compared.

Figure 2C:
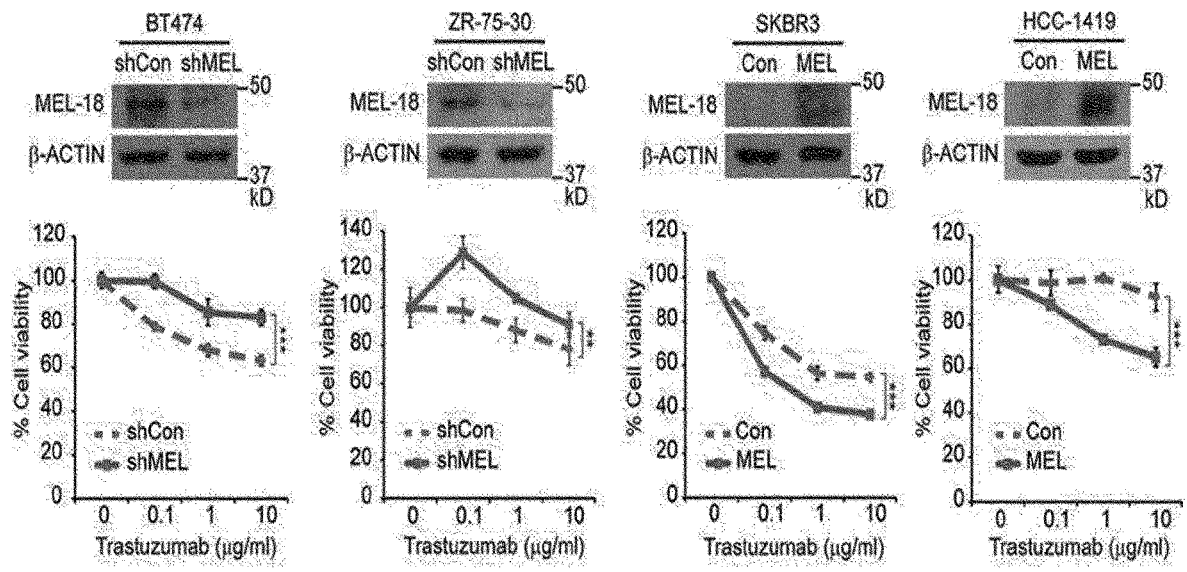
FIG. 2C shows the effect of MEL-18 on trastuzumab resistance in HER2+ breast cancer cell lines according to an exemplary embodiment of the present invention. Stable knockdown or overexpression of MEL-18 in each cell line was confirmed by immunoblotting (top). Cell survival after treatment with trastuzumab (m/m1) or a vehicle (Con) for 5 days was analyzed using the SRB analysis (bottom). shCon represents a shRNA control; shMEL represents MEL-18 shRNA; Con represents an empty vector; and MEL represents MEL-18.
Figure 2D:
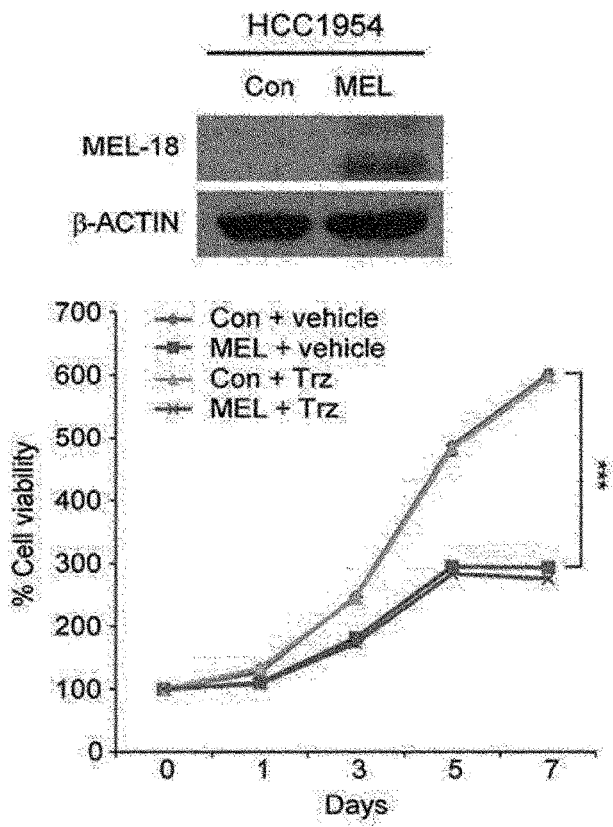
FIG. 2D shows the result confirming that MEL-18 inhibition induces trastuzumab resistance in HER2+ breast cancer according to an exemplary embodiment of the present invention, and graphs showing cell survival after treatment with 10 μg/ml of trastuzumab (Trz) or a vehicle (mean±SD (n=3), ***$P<0.001$ control (Con)(one-way ANOVA)).
Figure 2E:
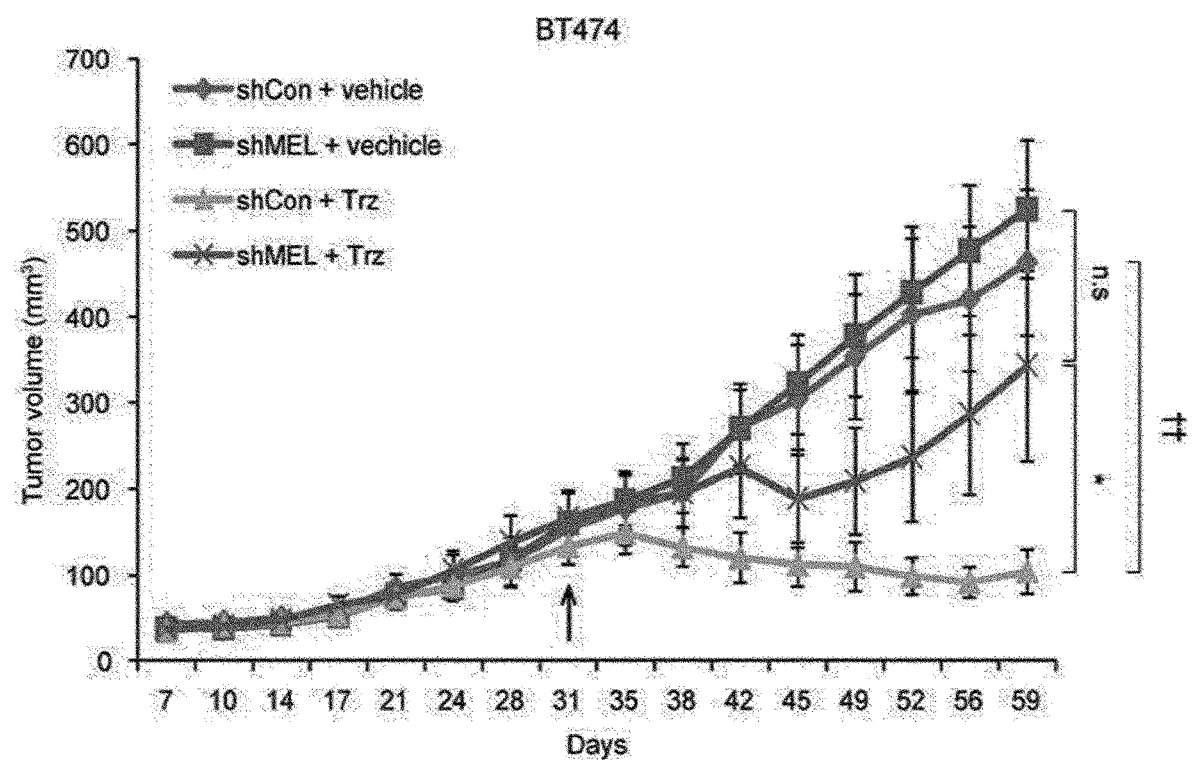
FIG. 2E shows the result confirming that MEL-18 inhibition induces trastuzumab resistance in HER2+ breast cancer according to an exemplary embodiment of the present invention, and tumor growth curves for NOD/SCID mice injected with a control or MEL-18 knockdown BT474 cells (Arrows indicate the time when treatment was started with trastuzumab or a vehicle; mean±SEM (n=7); *$P<0.05$ relative to the control (Con or shCon); and ††$P<0.01$ relative to the vehicle-treated control (one-way ANOVA)).
Figure 2F:
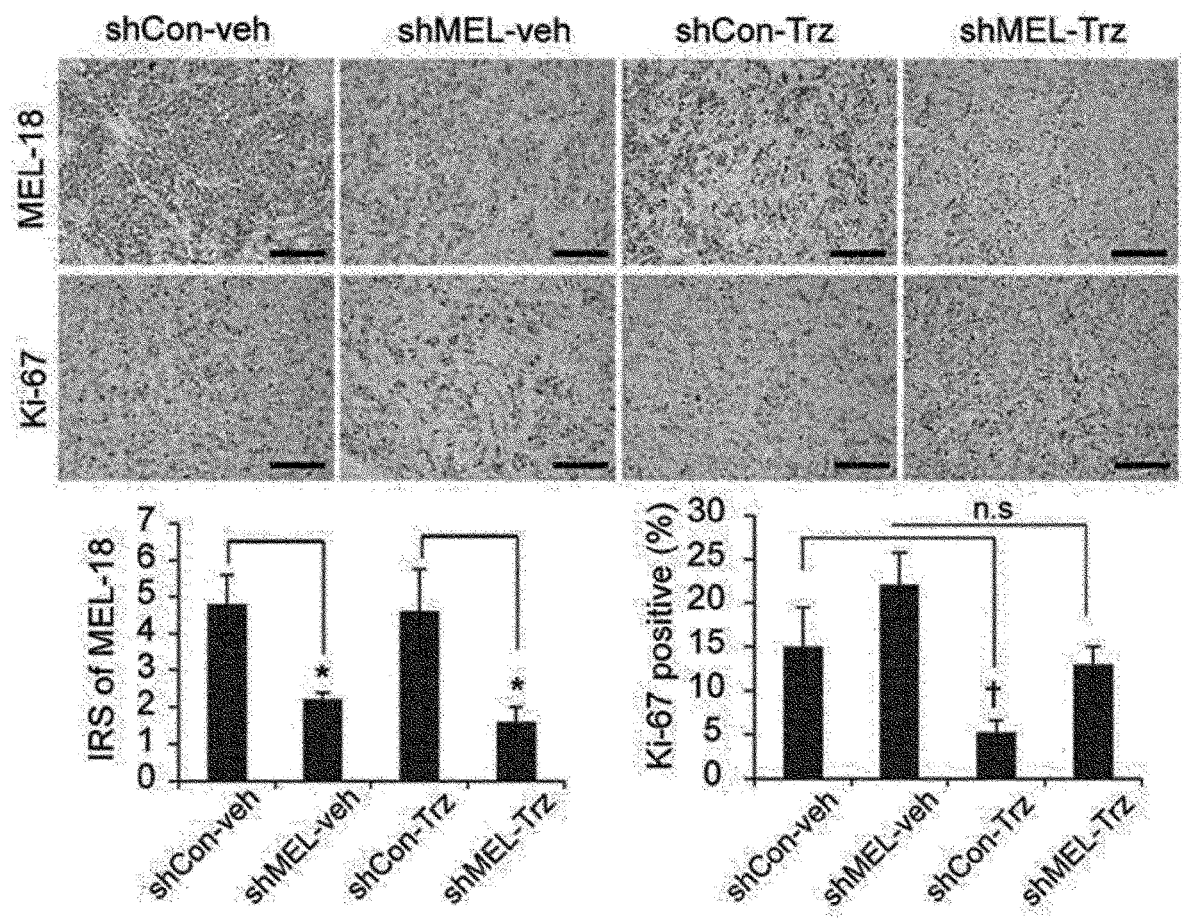
FIG. 2F shows the immunohistochemistry results for MEL-18 and Ki-67 in the xenografted tumors from each group according to an exemplary embodiment of the present invention (mean±SD, n=5). IRS, immunoreactive score. The scale bar, 100 μm. *$P<0.05$ relative to the shCon and †$P<0.05$ relative to the vehicle (one-way ANOVA and post-hoc LSD test).

As shown in FIGS. 2C, 2D and 2E, similar to the results obtained by in vitro cell viability analysis, the shRNA-mediated knockdown of MEL-18 induced trastuzumab resistance, whereas MEL-18 overexpression increased trastuzumab sensitivity in these cells (FIG. 2C). Specifically, shRNA-mediated inhibition of MEL-18 in BT474 cells induced trastuzumab resistance, whereas MEL-18-overexpressing SKBR3 cells exhibited a higher growth inhibitory effect than trastuzumab-treated control cells. In HCC-1954 cells having trastuzumab resistance due to I3KH1047R mutation, MEL-18 overexpression did not make the cells sensitive to trastuzumab, but brought a considerable decrease in cell growth (FIG. 2D). Like the in vitro results, although orthotopic mouse xenograft models of MEL-18-knockdown BT474 cells exhibited increased promoted tumor growth regardless of trastuzumab treatment, control mice responded to trastuzumab (FIGS. 2E and 2F). Such a result shows that MEL-18 loss mediates trastuzumab resistance, and indicates that MEL-18 amplification can be a predictor for trastuzumab sensitivity in HER2-positive breast cancer.

3. Confirmation of MEL-18 Effect on Activation of ErbB Family Receptor

Next, the role of MEL-18 in regulation of trastuzumab responses in HER2-positive breast cancer was examined, and the result is shown in FIGS. 3A, 3B, 3C, 8A and 8B.

Figure 3A:
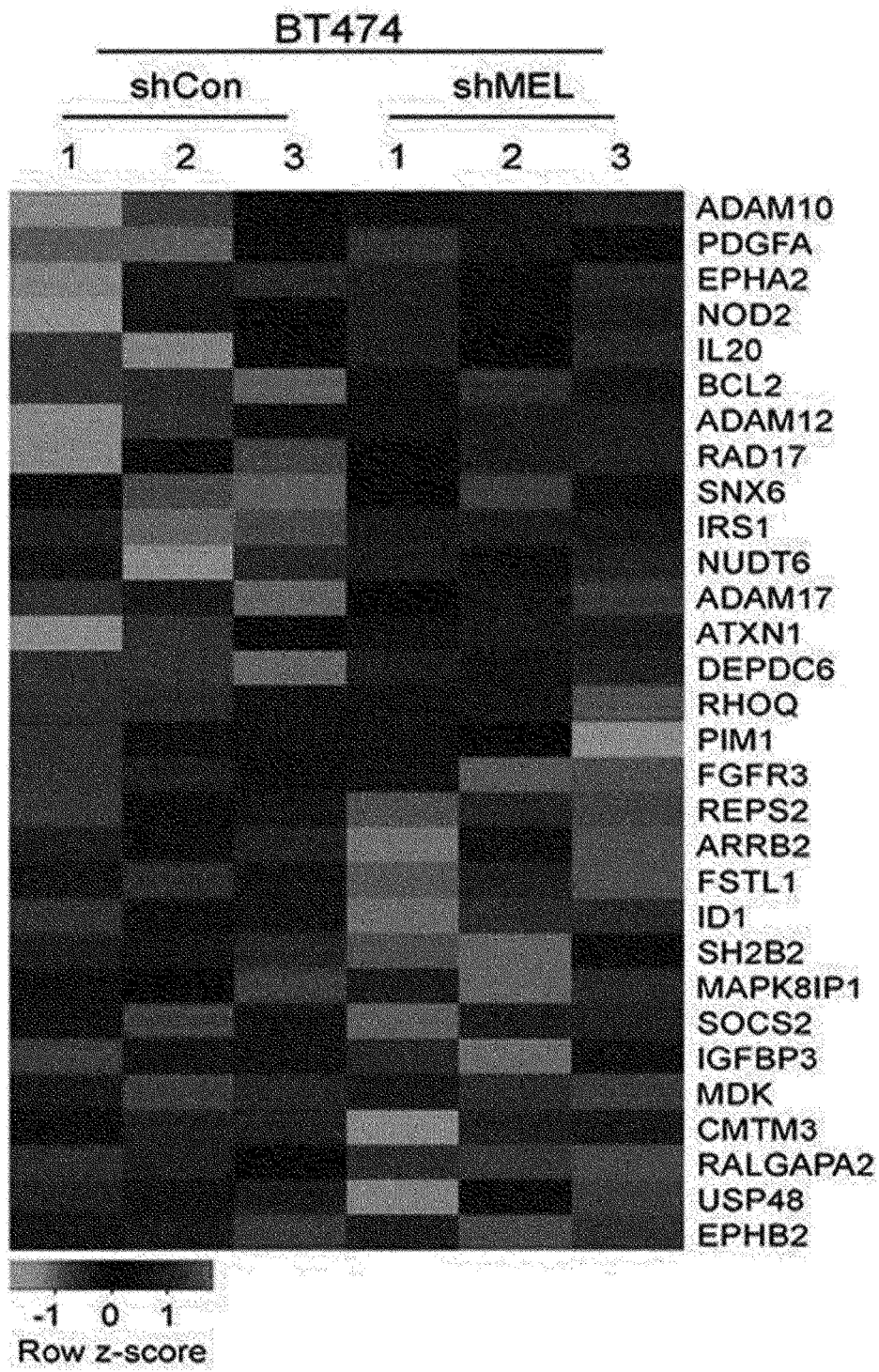
FIG. 3A shows that MEL-18 regulates ErbB phosphorylation and downstream signals according to an exemplary embodiment of the present invention, and a heatmap image obtained from the microarray analysis showing the differential expression of RTK signal-associated markers in a control (shCon) and MEL-18 shRNA (shMEL).
Figure 3B:
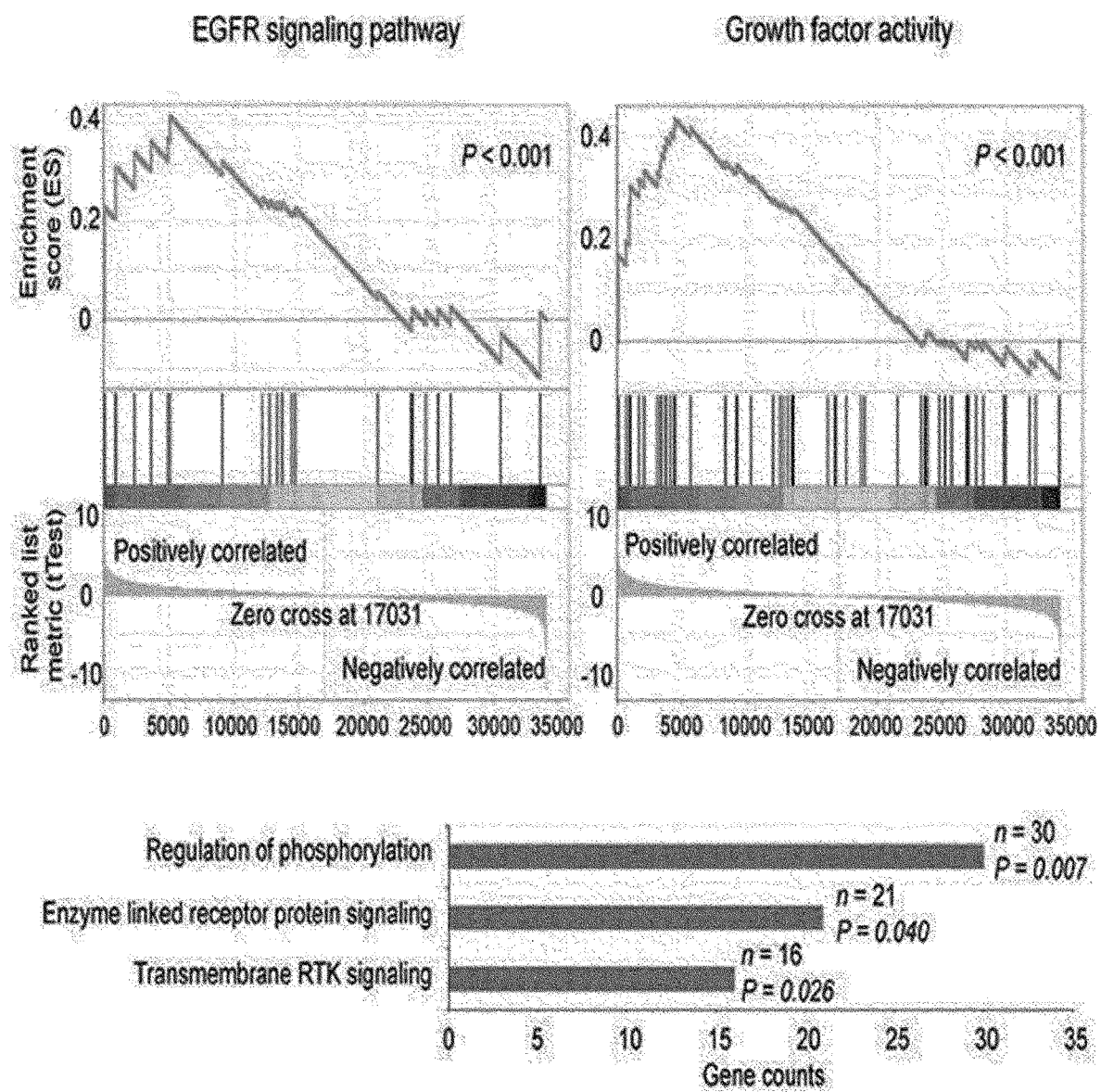
FIG. 3B shows that MEL-18 regulates ErbB phosphorylation and downstream signals according to an exemplary embodiment of the present invention, showing that the correlation of the gene expression profile of BT474/shMEL-18 cells with each gene set (top) and the result of gene ontology (GO) analysis of MEL-18 target genes (bottom).
Figure 3C:
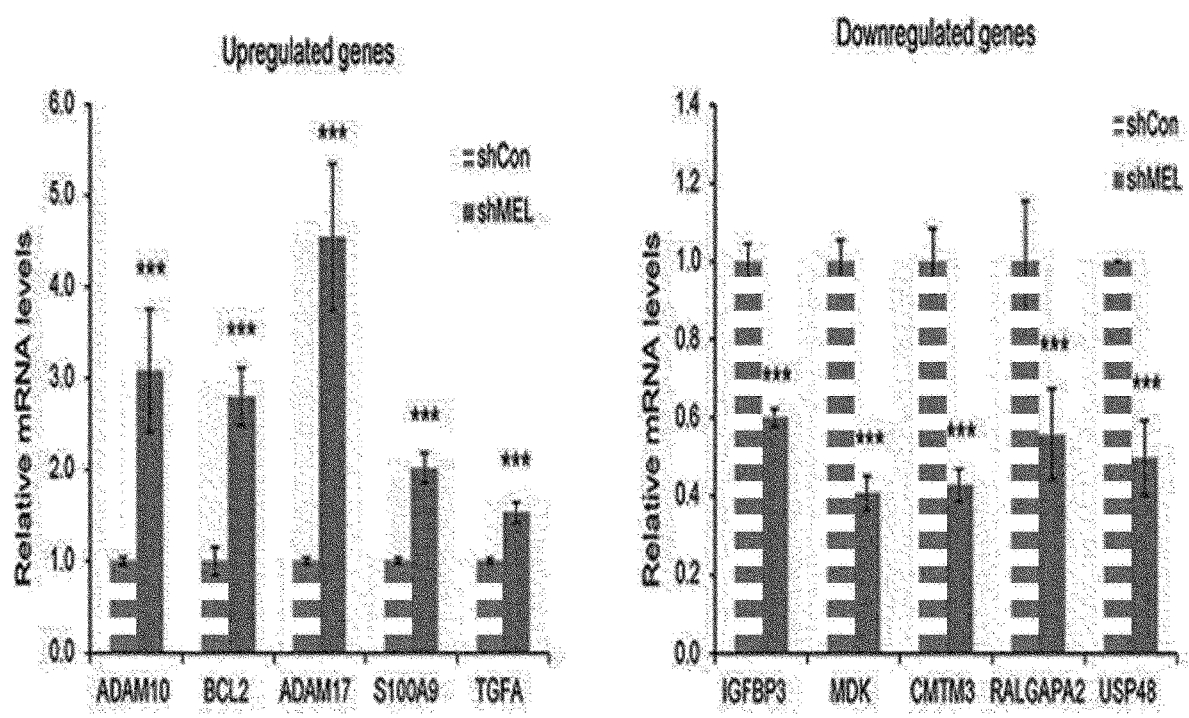
FIG. 3C shows that MEL-18 regulates ErbB phosphorylation and downstream signals according to an exemplary embodiment of the present invention, and the expression of each gene measured by qRT-PCR (data is expressed as mean±SD (n=3), and based on the two-tailed Student's t test, ***$P<0.001$ vs. control (shCon or Con).
Figure 8B:
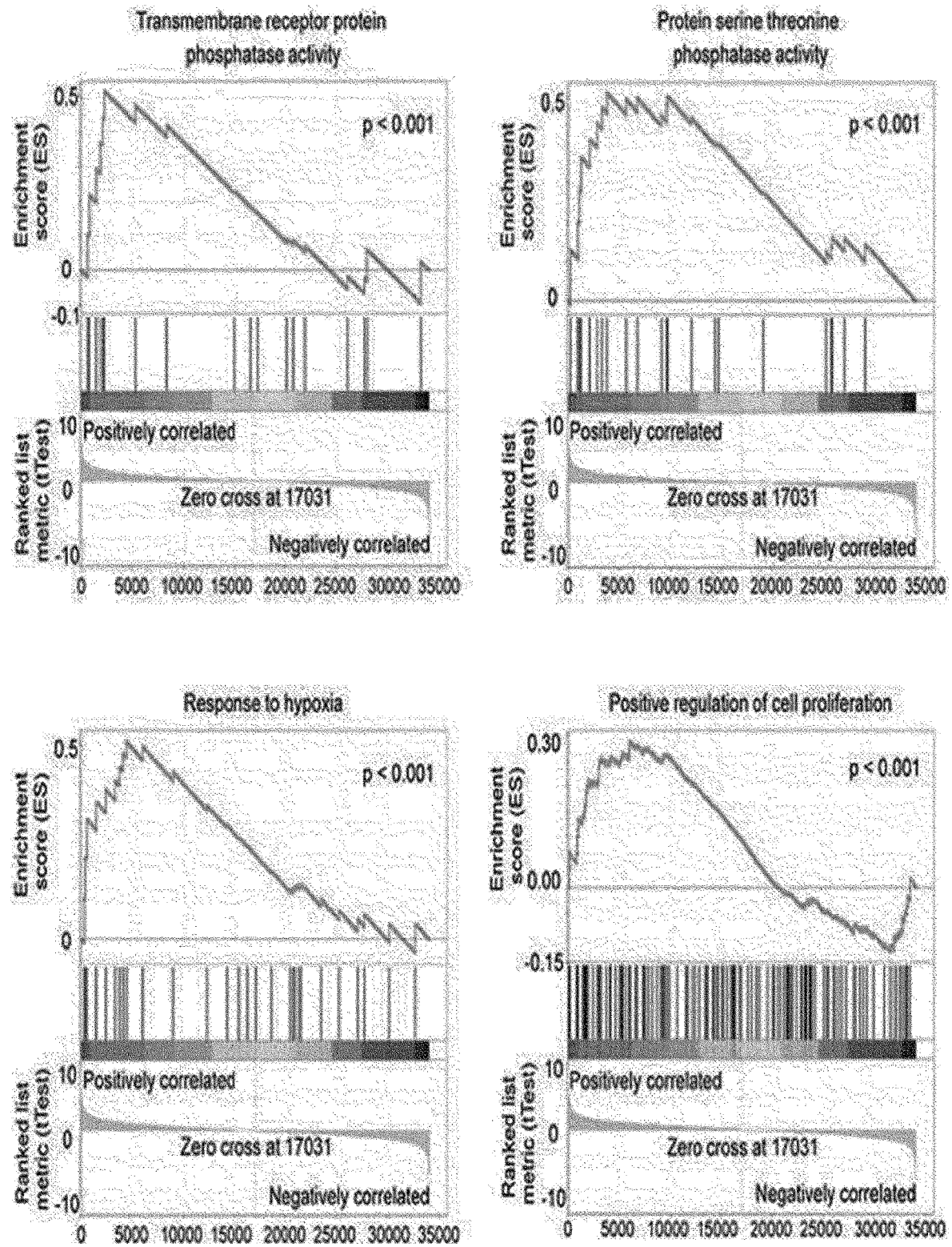
FIG. 8B shows the function of a MEL-18 target gene analyzed by a microarray using GSEA according to an exemplary embodiment of the present invention, and plots of gene sets having the statistically positive correlation with MEL-18 knockdown derived from different cancer occurring pathways.
Figure 9A:
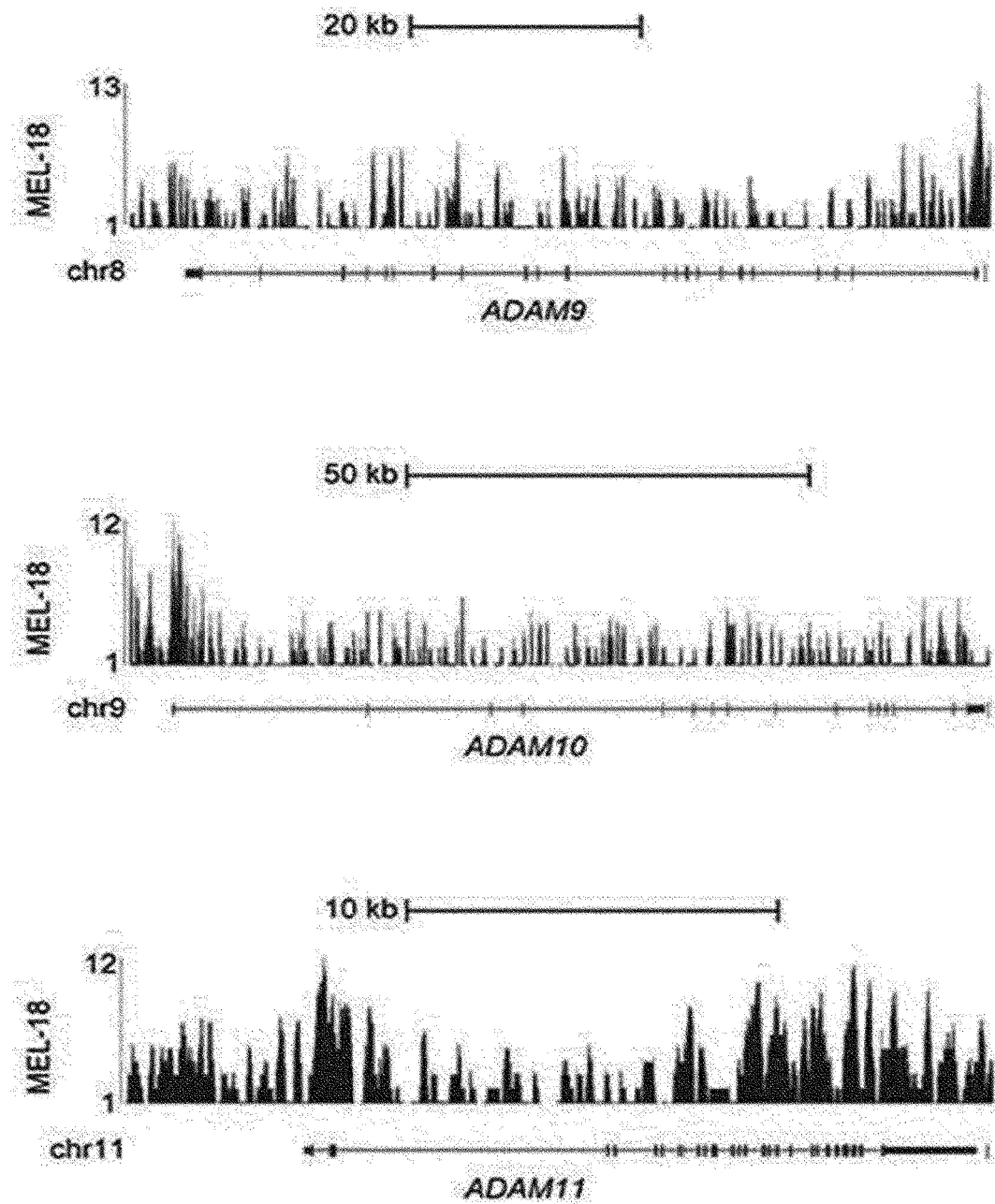
FIGS. 9A and 9B show the results of ChIP-seq analysis for MEL-18 binding to promoter sites of ADAM family genes, and the example of a peak map for ChIP-seq data of MEL-18 targets from mouse embryonic stem cells (GSE67868).
Figure 9B:
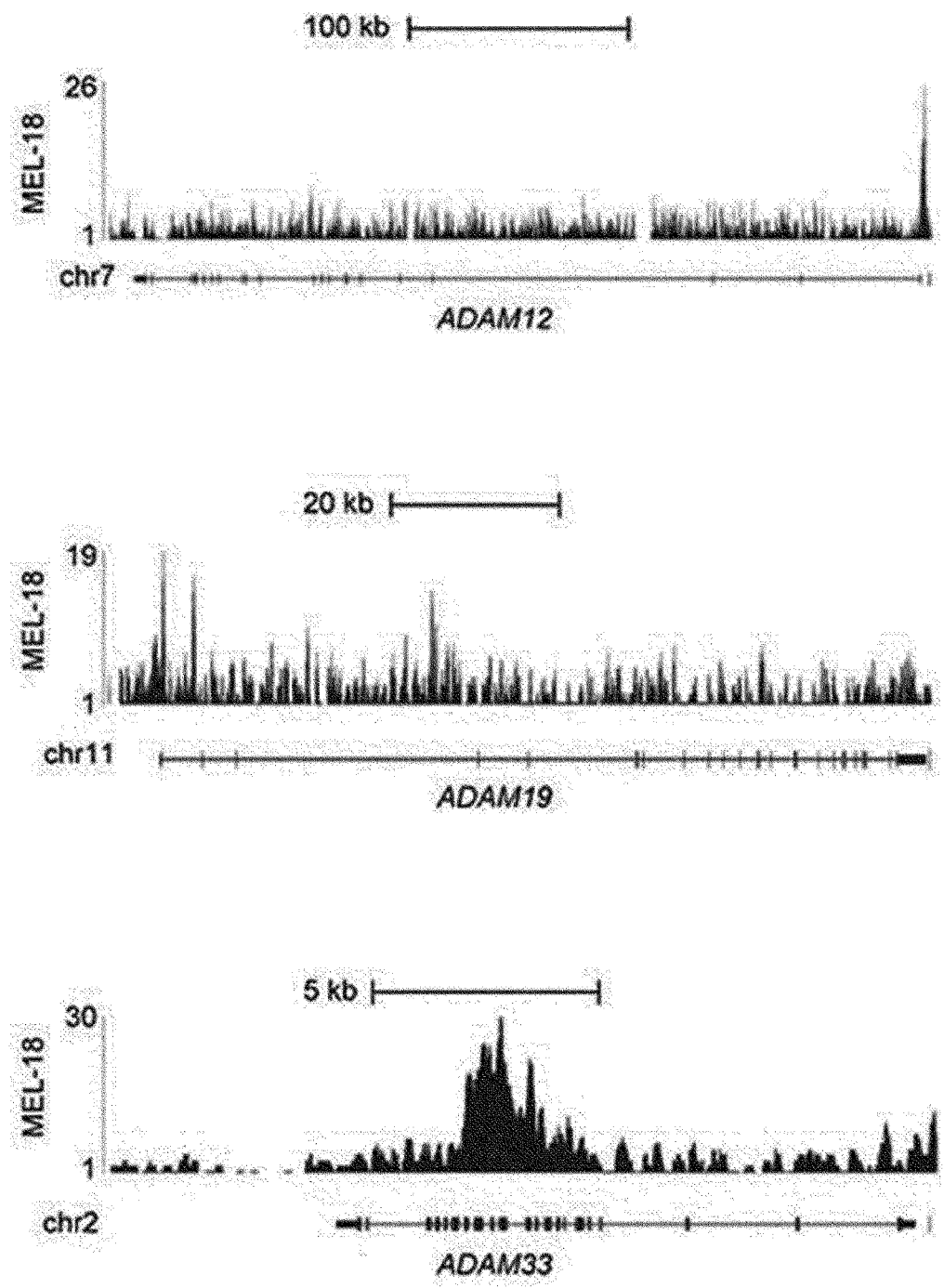

Gene expression microarray analysis showed different gene expression profiles between a control and MEL-18-knockdown HER2-positive breast cancer cells (FIG. 3A), and here, gene sets associated with EGFR signaling and growth factor activity, and different oncogenesis pathways were significantly increased (FIG. 3B, and FIGS. 8A and 8B). Changes in MEL-18 targeted gene expression involved in ADAM10, ADAM17, S100A9, TGF- and BCL-2 pathways were proved by qRT-PCR (FIG. 3C).

To further confirm whether microarray MEL-18 changes the activity of an EGFR-related signaling pathway as suggested in the microarray analysis, under MEL-18 expression, phosphorylation profiles of several RTKs were measured using phospho-RTK array and immunoblotting.

Figure 3D:
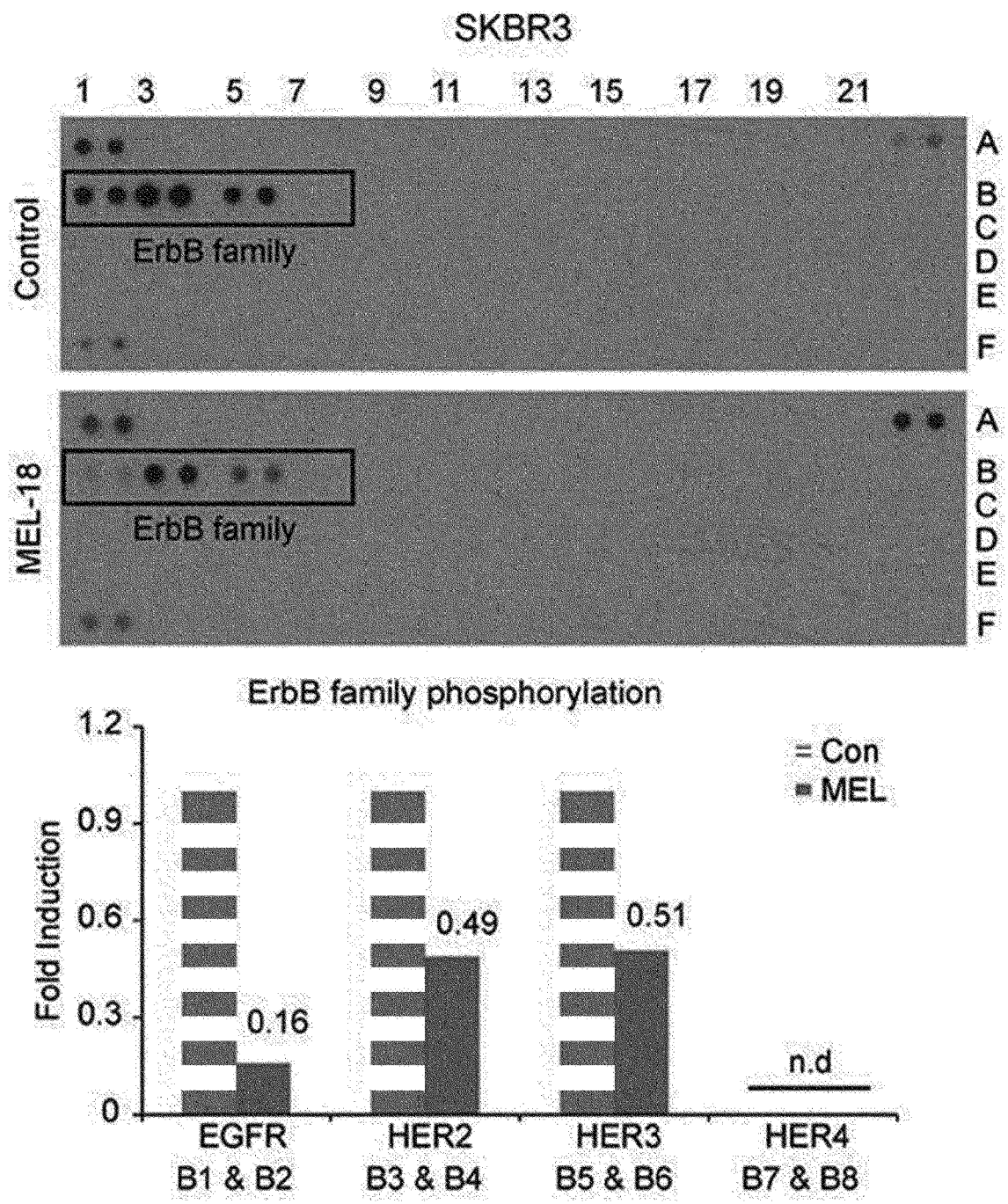
FIG. 3D shows that MEL-18 regulates ErbB phosphorylation and downstream signals according to an exemplary embodiment of the present invention, showing phosphorylation-RTK analysis results for SKBR3 cells expressing MEL-18 or the control representing different phosphorylation levels of RTK (spot analysis, top) and changes in relative band intensity measured using the AlphaEaseFC Software (bar graph, bottom).
Figure 3E:
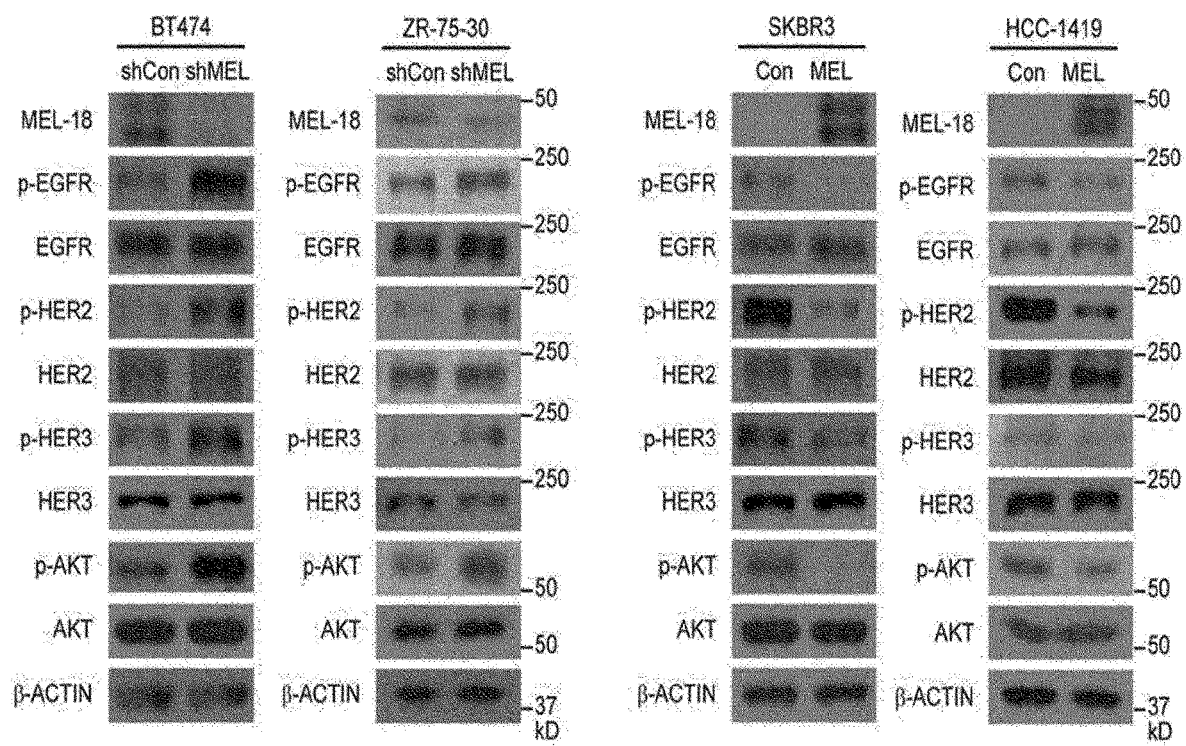
FIG. 3E shows that MEL-18 regulates ErbB phosphorylation and downstream signals according to an exemplary embodiment of the present invention, and shows immunoblotting results for MEL-18-knockdown (shMEL) or MEL-18-overexpressing (MEL) breast cancer cells (BT474, ZR-75-30, SKBR3, HCC-1419) and control cells (shCon and Con), representing RTK and downstream phosphorylation changes and relative expression.

As shown in FIGS. 3D and 3E, in MEL-18-overexpressing SKBR3 cells, compared with control cells, the phosphorylation levels of EGFR, HER2 and HER3, constituting the ErbB family, were significantly reduced, but expression levels were not reduced (FIGS. 3D and 3E). Similar effects were also observed in MEL-18-knockdown BT474 cells (FIG. 3E). Consequently, AKT phosphorylation was negatively regulated by MEL-18 in these cells, indicating that the ErbB-PI3K-AKT pathway is inhibited by MEL-18 (FIG. 3E). Therefore, it was concluded that MEL-18 inhibits the regulation of an ErbB signaling pathway by changing the kinase activity of the ErbB family.

4. Confirmation of Epigenetic Suppression of MEL-18-Mediated ErbB Ligand Sheddase ADAM10/17

To identify the molecular mechanism by which MEL-18 affects phosphorylation levels of ErbB family receptors, the expression of ADAM family sheddases for an ErbB ligand involved in ligand-dependent ErbB signaling activity and anti-HER2 therapy resistance was further confirmed.

Figure 4A:
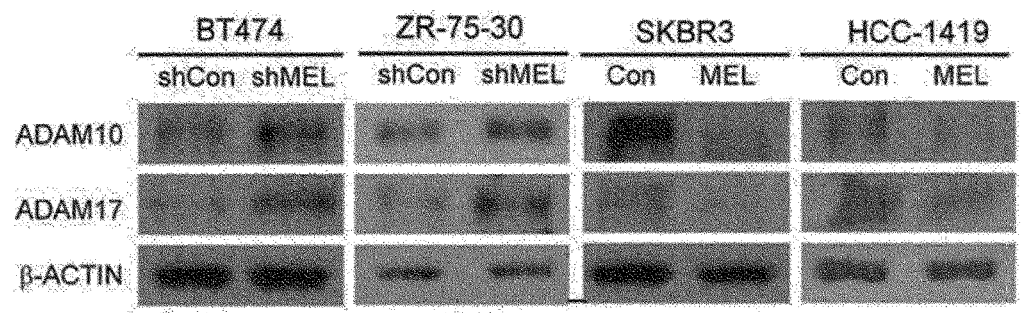
FIG. 4A shows the results obtained from by ADAM10 and ADAM17 downregulation by MEL-18 according to an exemplary embodiment of the present invention, and immunoblotting results showing changes in ADAM10 and ADAM17 expression at the protein level due to MEL-18 knockdown or overexpression. SKBR3 and HCC-1419 cell lines (MEL represents a MEL-18-overexpressing experimental group, and Con represents a control) dominantly expressed the mature form of ADAM10 (~65 kDa), and BT474 and ZR-75-30 cell lines (shMEL represents a MEL-18-knockdown experimental group, and shCon represents a control) expressed a pro form of ADAM10 (~80 kDa).
Figure 4B:
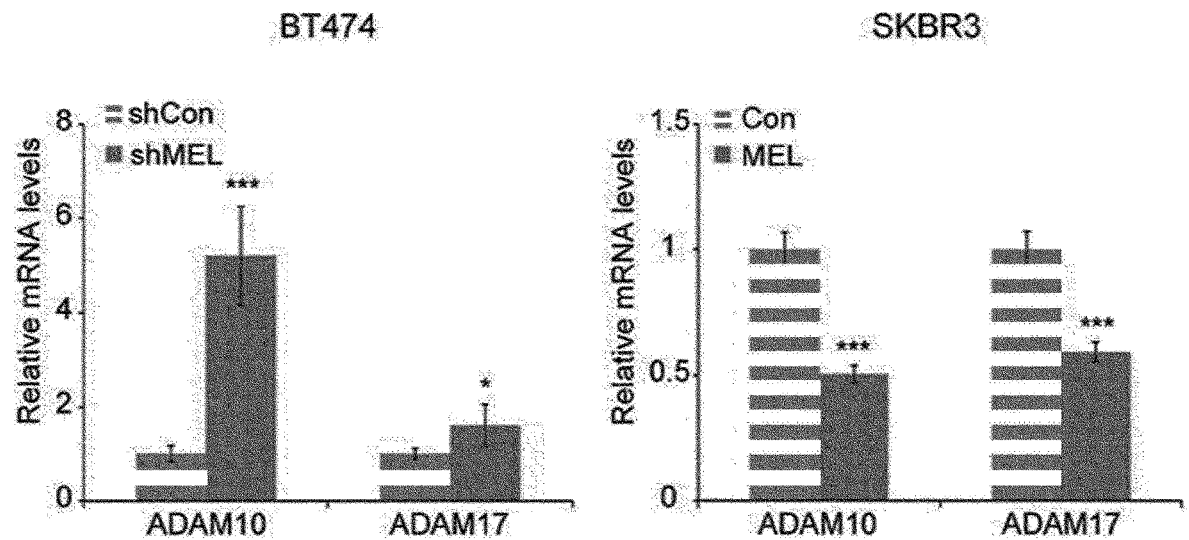
FIG. 4B shows the results obtained from by ADAM10 and ADAM17 downregulation by MEL-18 according to an exemplary embodiment of the present invention, and qRT-PCR results showing changes in mRNA levels of ADAM10 and ADAM17 in stable cell lines. In BT474 cells, shMEL represents a MEL-18-knockdown experimental group, shCon represents a control, and in SKBR3 cells, MEL represents a MEL-18-overexpressing experimental group, and Con represents a control. The qRT-PCR results are expressed as mean±SD of triplicate measurements, and based on the two-tailed Student's t test, *$P<0.05$ or ***$P<0.001$ relative to the control (shCon or Con).
Figure 4C:
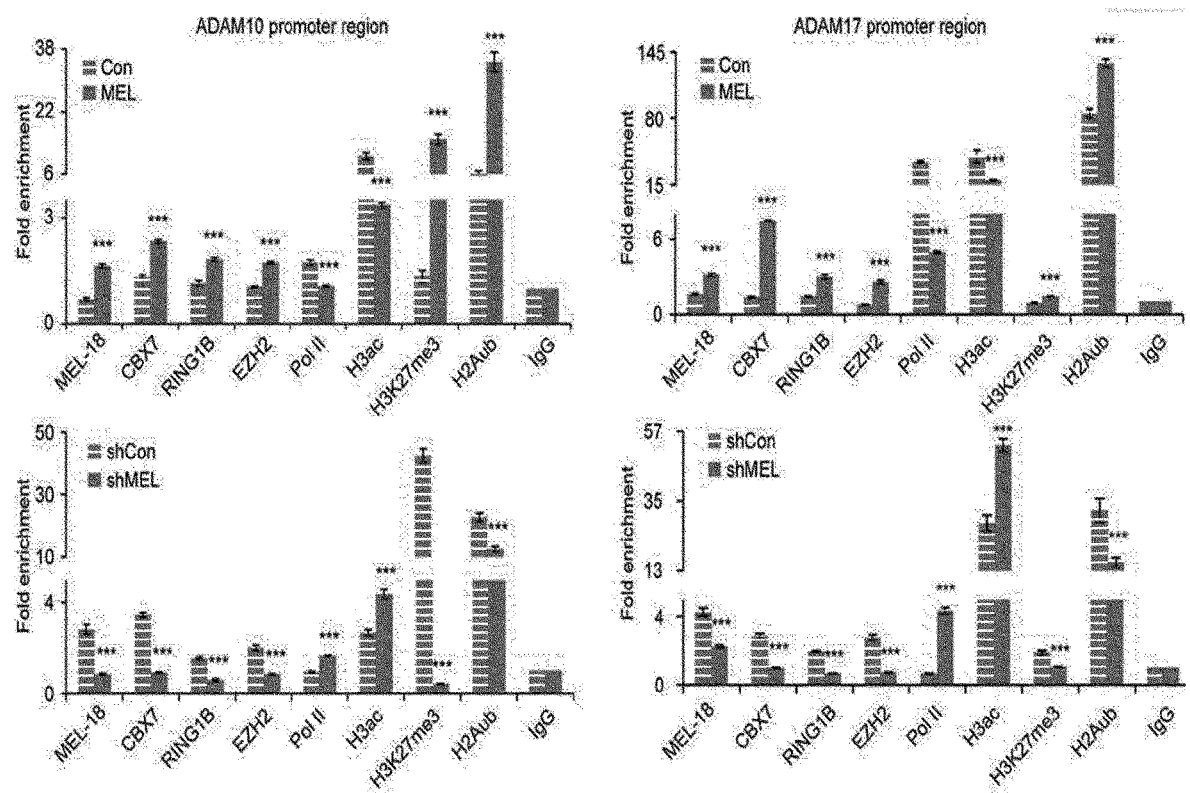
FIG. 4C shows the results obtained from by ADAM10 and ADAM17 downregulation by MEL-18 according to an exemplary embodiment of the present invention, and ChIP-qPCR analysis results showing the amount of proteins recruited to the promoter regions of ADAM10 and ADAM17 in a MEL-18-overexpressing (MEL) breast cancer cell line SKBR3 (top), a MEL-18-knockdown (shMEL) breast cancer cell line BT474 (bottom), and control cells (shCon and Con). Data is expressed as mean±SD of triplicate measurements, based on the two-tailed Student's t test, ***$P<0.001$ relative to the control (shCon or Con), and IgG is a negative control.

As shown in FIGS. 4A, 4B, 4C and 9, MEL-18 knockdown increased protein and mRNA levels of ADAM10 and ADAM17 in BT474 cells, whereas MEL-18 overexpression decreased their expression in SKBR3 cells (FIGS. 4A and 4B). This means that MEL-18 plays a role in regulation of gene transcription. Chromatin immunoprecipitation (ChIP) analysis confirmed an increase in MEL-18 binding to ADAM10 and ADAM17 promoter regions in HER2-positive human breast cancer cell lines (FIG. 4C). After MEL-18 binds to the promoters, transcriptional active marker RNA polymerase II (Pol II) was dissociated from regions thereof, and histone H3 acetylation (H3ac) was also decreased in MEL-18-overexpressing SKBR3 cells (FIG. 4C). In addition, MEL-18 changed the modification of PRC1- and PRC2-dependent histones at these regions. In PRC1 members, CBX7 and RING1B well known as MEL-18 binding partners (42, 43) were co-bonded in ADAM10 and ADAM17 promoter regions, and H2AK119ub levels increased dependently with MEL-18 expression levels. In addition, MEL-18 promotes the binding and enzymatic activity of EZH2, which is a catalyst subunit of PRC2 with respect to H3K27 in these regions. Similarly, PRC2-induced H3K27me3 and PRC1-mediated H2AK119ub were reduced in ADAM10 and ADAM17 promoters in MEL-18-knockdown BT474 cells (FIG. 4C).

Figure 4D:
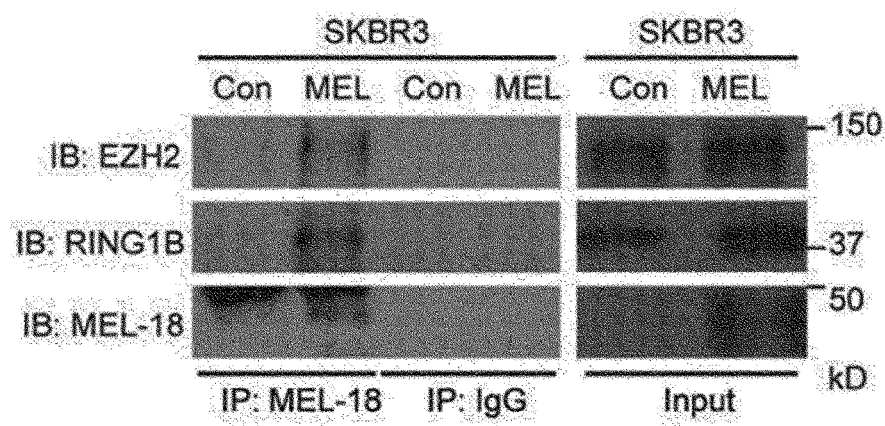
FIG. 4D shows the co-immunoprecipitation results for the binding levels of MEL-18 with EZH2 and RING1B according to ADAM10 and ADAM17 down regulation by MEL- according to an exemplary embodiment of the present invention. After immunoprecipitation (IP) with an antibody against MEL-18, immunoblotting (IB) was performed using the indicated antibody; a MEL-18-overexpressing (MEL) breast cancer cell line SKBR3 and control cells (Con).
Figure 4E:
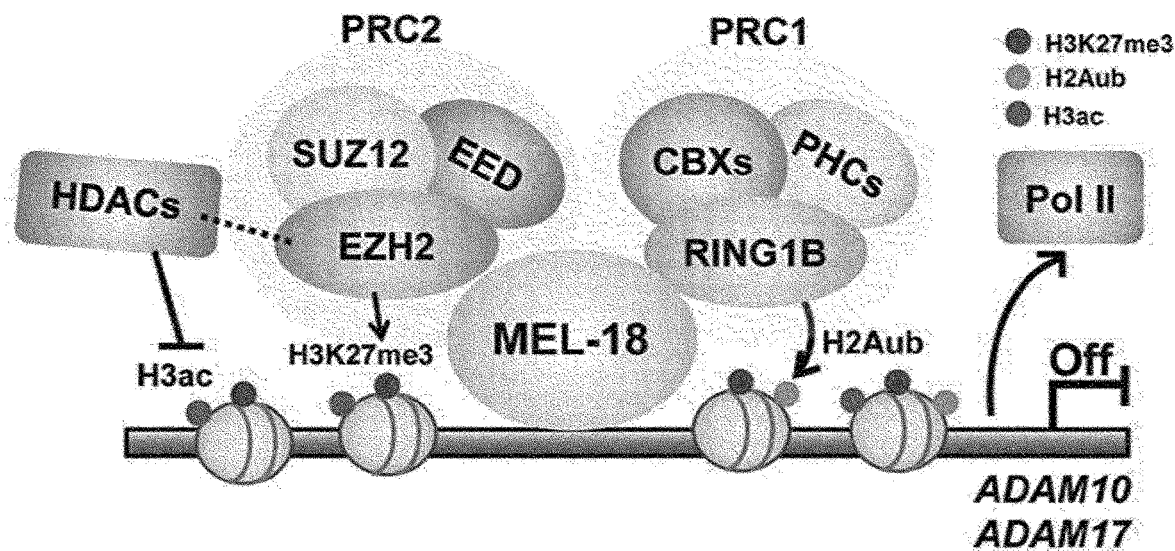
FIG. 4E shows a gene silencing model suggested by MEL-18 according to an exemplary embodiment of the present invention.

In addition, as shown in FIGS. 4D and 4E, co-immunoprecipitation analysis clearly confirmed that MEL-18-dependent EZH2 recruitment to target chromatin is caused by the interaction between MEL-18 and EZH2 proteins (FIG. 4D). This result shows that MEL-18 epigenetically suppresses the expression of ErbB ligand sheddases ADAM10 and ADAM17 by forming a transcription inhibitory complex in cooperation with PRC2 and PRC1 (FIG. 4E).

5. Role of ADAM10/17 in Mediation of MEL-18 Loss-Induced Trastuzumab Resistance

To verify whether changes in the expression of ADAM10 and ADAM17 by MEL-18 play a role in ligand-dependent ErbB signaling associated with trastuzumab resistance, the effect of MEL-18 on the production of ErbB ligands was investigated.

Figure 5A:
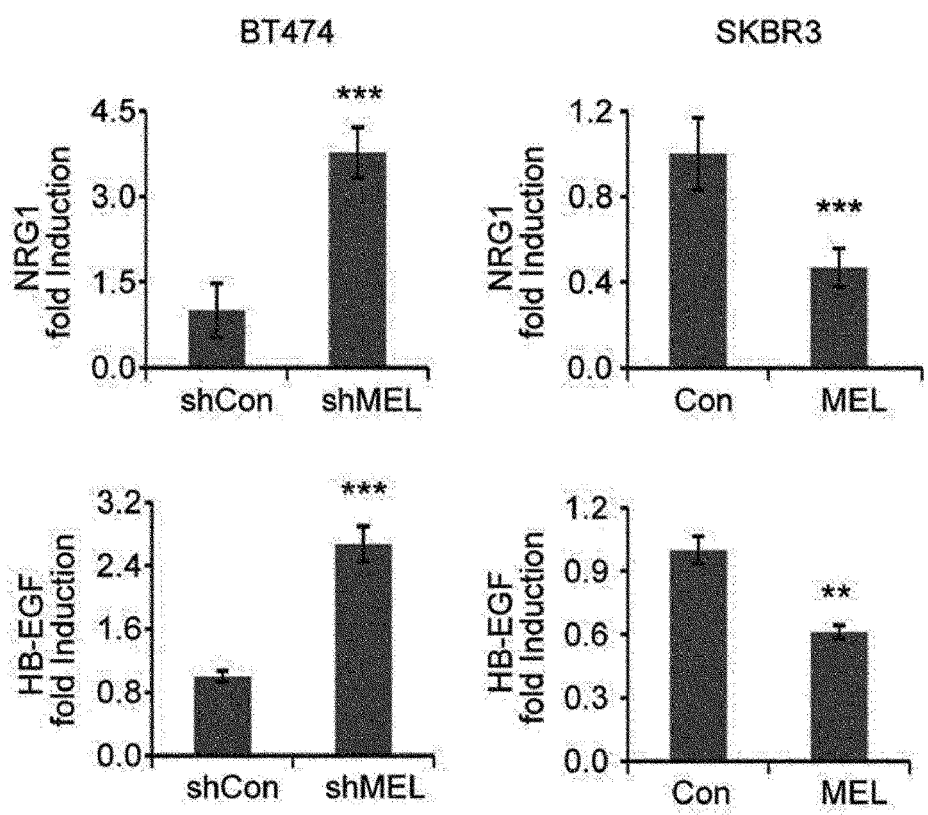
FIG. 5A shows that ADAM10/17 expression increased by MEL-18 knockdown increases ErbB phosphorylation and induces trastuzumab resistance in HER2+ breast cancer according to an exemplary embodiment of the present invention, and the ELISA results confirming the protein levels of NRG1 ligands present in the culture medium supernatant of SKBR3 cell lines (MEL is a MEL-18-overexpressing experimental group, and Con is a control) or BT474 cell lines (shMEL is a MEL-18-knockdown experimental group, and shCon is a control). Data is expressed as mean±SD of triplicate measurements, based on the two-tailed Student's t test $P<0.01$,*$P<0.001$ relative to the control (shCon or Con).
Figure 5B:
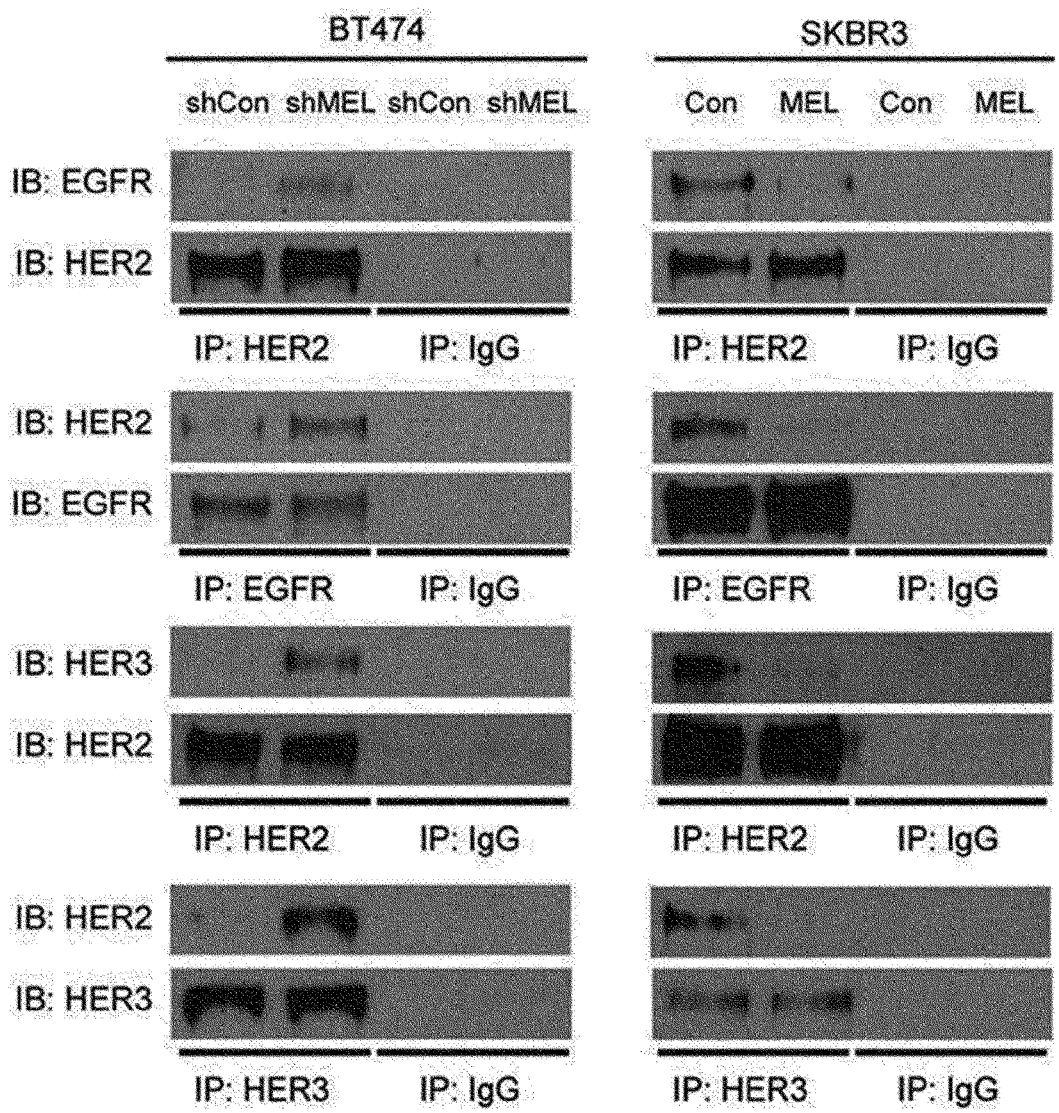
FIG. 5B shows that ADAM10/17 expression increased by MEL-18 knockdown increases ErbB phosphorylation and induces trastuzumab resistance in HER2+ breast cancer according to an exemplary embodiment of the present invention, and the results of immunoprecipitation and immunoblotting for SKBR3 cell lines (MEL is a MEL-18-overexpressing experimental group, and Con is a control) and BT474 cell lines (shMEL is a MEL-18-knockdown experimental group, and shCon is a control), performed to confirm a dimerization status between HER2 and EGFR.

As shown in FIGS. 5A and 5B, in MEL-18-knockdown BT474 cells, secreted HB-EGF and heregulin-1 (NRG1) levels and the amounts of ligands (17) specific for EGFR and HER3 increased (FIG. 5A). In contrast, the production of these ligands was reduced in response to MEL-18 overexpression in SKBR3 cells (FIG. 5A). In addition, the effect of MEL-18 on production of ErbB ligands led to a change in heterodimerization between ErbB family receptors. Co-immunoprecipitation analysis shows that MEL-18 knockdown in BT474 cells enhanced the binding of HER2 with EGFR and HER3, and MEL-18 overexpression in SKBR3 cells inhibits their dimerization (FIG. 5B).

Figure 5C:
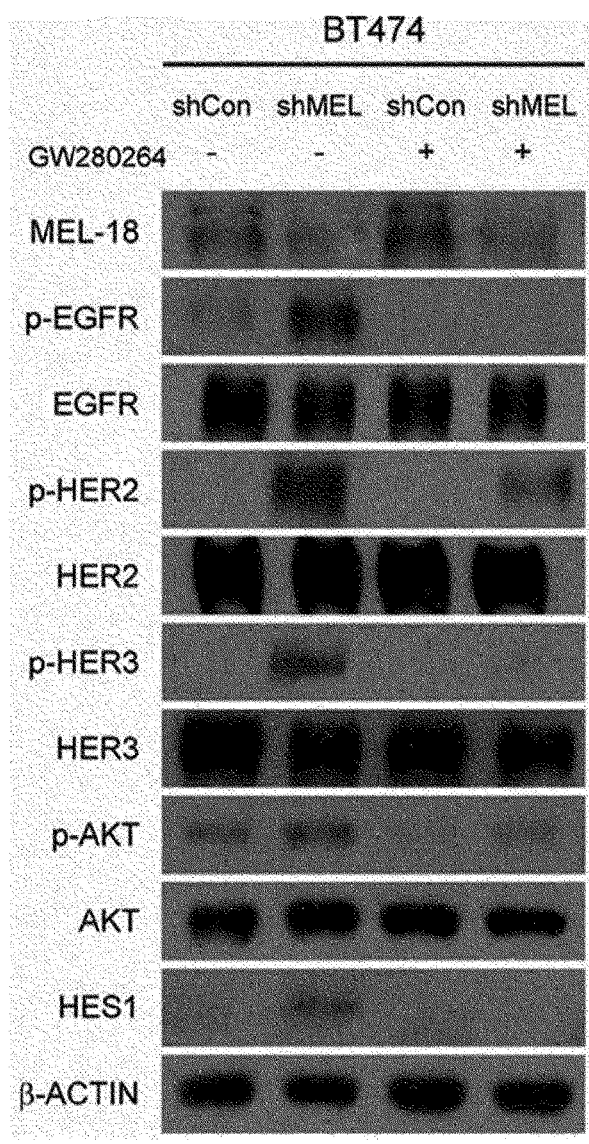
FIG. 5C shows that ADAM10/17 expression increased by MEL-18 knockdown increases ErbB phosphorylation and induces trastuzumab resistance in HER2+ breast cancer according to an exemplary embodiment of the present invention, and changes in the expression levels and phosphorylation of ErbB family proteins in lysates of BT474 cell lines obtained by treatment with 1 µM GW280264 (GW), which is an ADAM10/17 inhibitor, for 24 hours, measured by immunoblotting (shMEL is a MEL-18-knockdown experimental group, and shCon is a control).
Figure 5D:
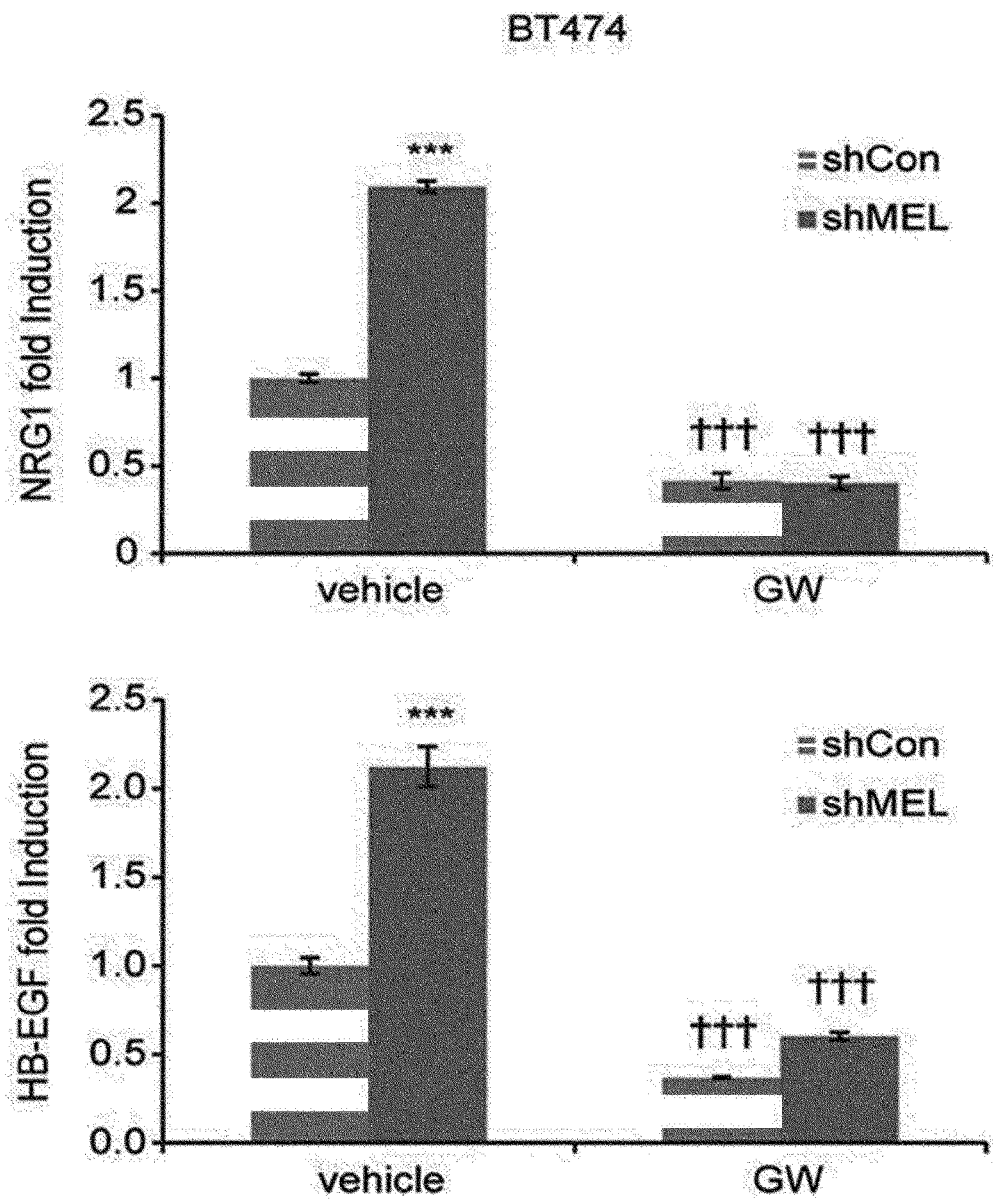
FIG. 5D shows that ADAM10/17 expression increased by MEL-18 knockdown increases ErbB phosphorylation and induces trastuzumab resistance in HER2+ breast cancer according to an exemplary embodiment of the present invention, and changes in the secretion levels of ErbB ligands after treatment of BT474 cell lines with GW280264 (GW) (shMEL is a MEL-18-knockdown experimental group, shCon is a control, and vehicle is a control).

In addition, as shown in FIGS. 5C and 5D, as a result of treatment with the ADAM10/17 dual inhibitor GW280264, such effects were mediated by the MEL-18 knockdown-mediated secretion of ErbB ligands and the sheddase activity of ADAM10 and ADAM17 reversing the activation of ErbB-PI3K-AKT signaling in BT474 cells (FIGS. 5C and 5D).

Figure 5E:
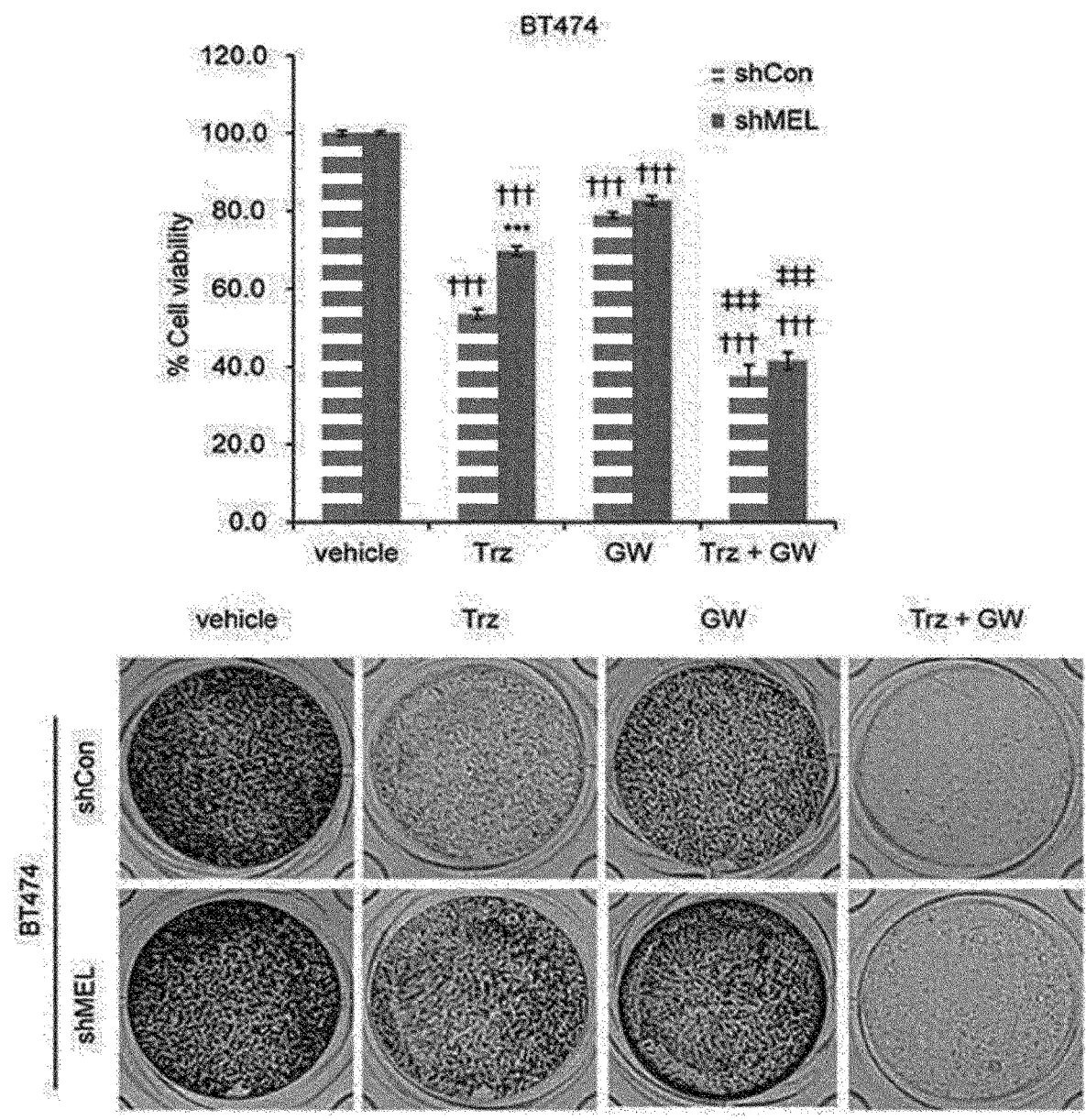
FIG. 5E shows that ADAM10/17 expression increased by MEL-18 knockdown increases ErbB phosphorylation and induces trastuzumab resistance in HER2+ breast cancer according to an exemplary embodiment of the present invention, and cell viability after treatment of BT474 cell lines with trastuzumab (Trz) and/or GW280264 (GW) or a vehicle for 5 days, confirmed by an SRB assay (top, graph) and a colony-forming assay (bottom, image). The SRB assay data is expressed as mean±SD (n=3), ***$P<0.001$ vs. a control (shCon), ††\$P<0.001$ vs. a vehicle-treated group and ‡$P<0.001$ were based on one-way ANOVA (shMEL is a MEL-18-knockdown experimental group, shCon is a control, vehicle is a control).

In addition, as shown in FIG. 5E, as a result of co-treatment of GW280264 with trastuzumab, it was confirmed that the anti-proliferative effect of trastuzumab in MEL-18-depleted BT474 cells was improved (FIG. 5E).

Figure 5F:
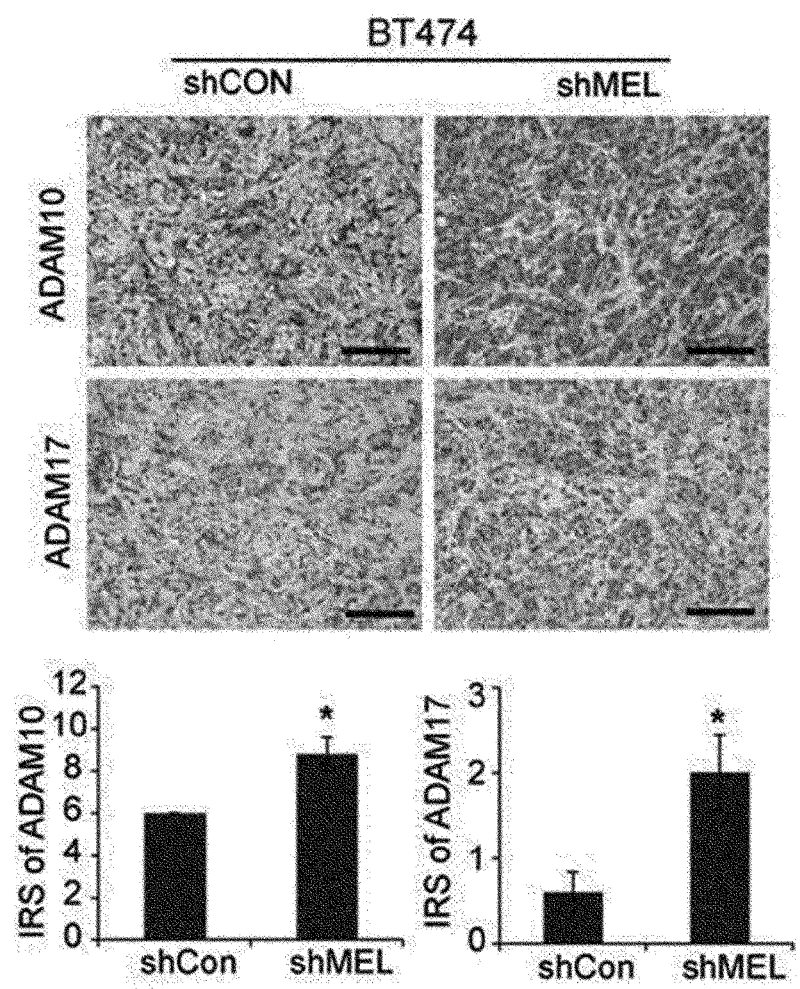
FIG. 5F shows that ADAM10/17 mediates MEL-18 loss-induced ErbB phosphorylation and trastuzumab resistance, and the results of immunohistochemical analysis for ADAM10 and ADAM17 expression in tumor tissues obtained from xenografted mice of each group. IRS is an immunoreactive score. The scale bar is 100 µm. Mean±SD (n=5). *$P<0.05$ vs. shCon (Student's t-test) (shMEL is a MEL-18-knockdown experimental group, and shCon is a control).
Figure 5G:
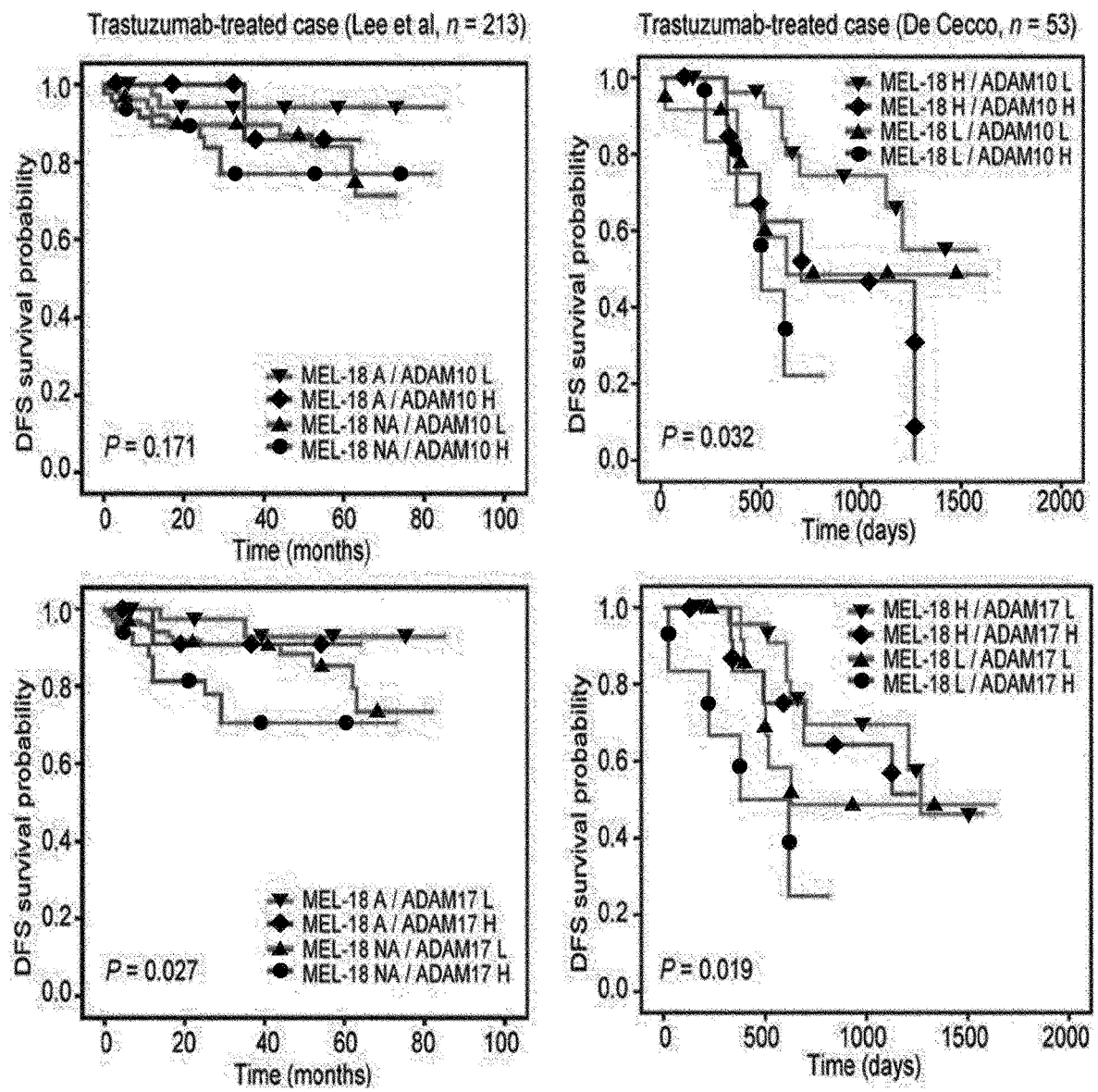
FIG. 5G shows the results of survival analysis of breast cancer patients treated with trastuzumab according to the amplification status (left) or expression levels (right) of MEL-18 in combination with ADAM10/17 expression (A, amplification; NA, non-amplification; H, high; L, low). In a cohort from public data (GSE55348, n=53), patients were divided into four groups by various quantile expressions of indicated genes (cutoffs of high expression group: MEL-18, 66$^{th}$ percentile; ADAM10: 25$^{th}$ percentile; ADAM17: 33th percentile). Data was analyzed using the Kaplan-Meier method with the log-rank test (left) or the Gehan-Breslow-Wilcoxon test (right).
Figure 6:
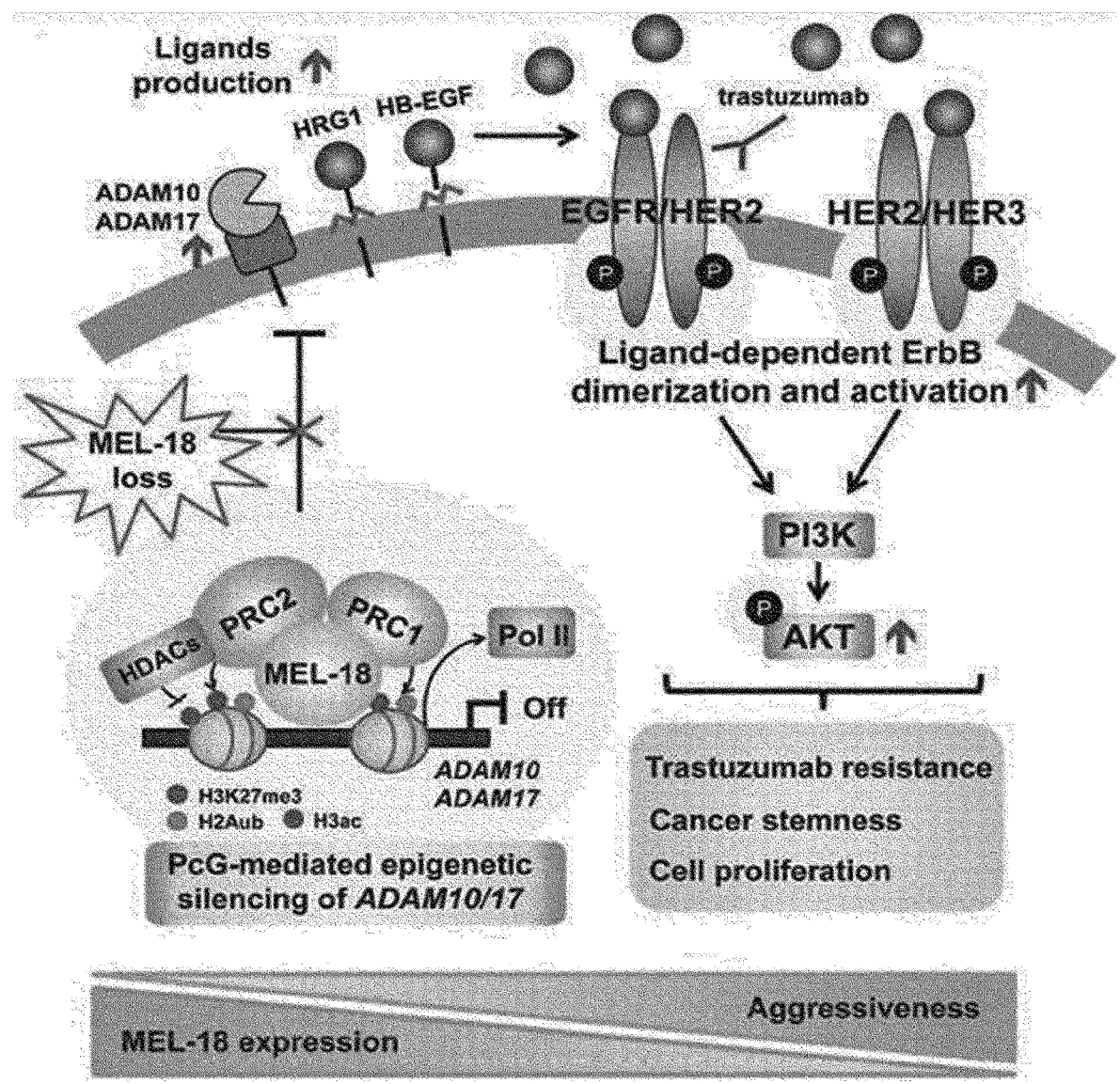
FIG. 6 shows a model suggested to regulate ErbB signaling and trastuzumab responses by MEL-18 in HER2+ breast cancer according to an exemplary embodiment of the present invention.

Moreover, consistent with the in vitro results, MEL-18 loss was associated with an increase in protein levels of ADAM10 and ADAM17 in breast tumors from xenograft mice (FIG. 5F). Particularly, in breast cancer patients (n=213) receiving trastuzumab treatment, a subgroup having MEL-18 amplification and a low expression level of ADAM17 had remarkably favorable disease-free survival (DFS), whereas a group having high ADAM17 expression and non-amplification of MEL-18 was associated with lower DFS (left, FIG. 5G). Patients showing low ADAM10 expression and MEL-18 amplification had a tendency toward a more favorable survival result. The analysis of a gene expression array from a public database also showed that trastuzumab-treated patients having overexpression of MEL-18 mRNA and underexpression of ADAM10 or ADAM17 mRNA showed prolonged relapse-free survival (right, FIG. 5G).

Therefore, this data indicated that ADAM10/17 sheddases triggerMEL-18 loss-induced trastuzumab resistance by mediating ErbB ligand production and receptor activation.

REFERENCES

1. M. Sauvageau, G. Sauvageau, Polycomb group proteins: multi-faceted regulators of somatic stem cells and cancer. Cell Stem Cell 7, 299-313 (2010).

2. H. Wang, L. Wang, H. Erdjument-Bromage, M. Vidal, P. Tempst, R. S. Jones, Y. Zhang, Role of histone H2A ubiquitination in Polycomb silencing. Nature 431, 873-878 (2004).
3. R. Cao, L. Wang, H. Wang, L. Xia, H. Erdjument-Bromage, P. Tempst, R. S. Jones, Y. Zhang, Role of histone H3 lysine 27 methylation in Polycomb-group silencing. Science 298, 1039-1043 (2002).
4. J. Y. Lee, G. Kong, MEL-18, a tumor suppressor for aggressive breast cancer. Oncotarget 6, 15710-15711 (2015).
5. W. J. Guo, M. S. Zeng, A. Yadav, L. B. Song, B. H. Guo, V. Band, G. P. Dimri, Mel-18 acts as a tumor suppressor by repressing Bmi-1 expression and down-regulating Akt activity in breast cancer cells. Cancer Res 67, 5083-5089 (2007).
6. L. Morey, A. Santanach, E. Blanco, L. Aloia, E. P. Nora, B. G. Bruneau, L. Di Croce, Polycomb Regulates Mesoderm Cell Fate-Specification in Embryonic Stem Cells through Activation and Repression Mechanisms. Cell Stem Cell 17, 300-315 (2015).
7. M. L. Riis, T. Luders, A. J. Nesbakken, H. S. Vollan, V. Kristensen, I. R. Bukholm, Expression of BMI-1 and Mel-18 in breast tissue—a diagnostic marker in patients with breast cancer. BMC Cancer 10, 686 (2010).
8. W. Wang, T. Yuasa, N. Tsuchiya, Z. Ma, S. Maita, S. Narita, T. Kumazawa, T. Inoue, H. Tsuruta, Y. Horikawa, M. Saito, W. Hu, O. Ogawa, T. Habuchi, The novel tumor-suppressor Mel-18 in prostate cancer: its functional polymorphism, expression and clinical significance. International journal of cancer 125, 2836-2843 (2009).
9. X. W. Zhang, Y. P. Sheng, Q. Li, W. Qin, Y. W. Lu, Y. F. Cheng, B. Y. Liu, F. C. Zhang, J. Li, G. P. Dimri, W. J. Guo, BMI1 and Mel-18 oppositely regulate carcinogenesis and progression of gastric cancer. Molecular cancer 9, 40 (2010).
10. B. H. Guo, X. Zhang, H. Z. Zhang, H. L. Lin, Y. Feng, J. Y. Shao, W. L. Huang, H. F. Kung, M. S. Zeng, Low expression of Mel-18 predicts poor prognosis in patients with breast cancer. Ann Oncol 21, 2361-2369 (2010).
11. J. Y. Lee, K. S. Jang, D. H. Shin, M. Y. Oh, H. J. Kim, Y. Kim, G. Kong, Mel-18 negatively regulates INK4a/ARF-independent cell cycle progression via Akt inactivation in breast cancer. Cancer Res 68, 4201-4209 (2008).
12. J. H. Park, J. Y. Lee, D. H. Shin, K. S. Jang, H. J. Kim, G. Kong, Loss of Mel-18 induces tumor angiogenesis through enhancing the activity and expression of HIF-1alpha mediated by the PTEN/PI3K/Akt pathway. Oncogene 30, 4578-4589 (2011).
13. H. Y. Won, J. Y. Lee, D. H. Shin, J. H. Park, J. S. Nam, H. C. Kim, G. Kong, Loss of Mel-18 enhances breast cancer stem cell activity and tumorigenicity through activating Notch signaling mediated by the Wnt/TCF pathway. FASEB J 26, 5002-5013 (2012).
14. J. Y. Lee, M. K. Park, J. H. Park, H. J. Lee, D. H. Shin, Y. Kang, C. H. Lee, G. Kong, Loss of the polycomb protein Mel-18 enhances the epithelial-mesenchymal transition by ZEB1 and ZEB2 expression through the downregulation of miR-205 in breast cancer. Oncogene 33, 1325-1335 (2014).
15. J. Y. Lee, H. Y. Won, J. H. Park, H. Y. Kim, H. J. Choi, D. H. Shin, J. H. Kang, J. K. Woo, S. H. Oh, T. Son, J. W. Choi, S. Kim, H. Y. Kim, K. Yi, K. S. Jang, Y. H. Oh, G. Kong, MEL-18 loss mediates estrogen receptor-alpha downregulation and hormone independence. J Clin Invest 125, 1801-1814 (2015).
16. D. J. Slamon, G. M. Clark, S. G. Wong, W. J. Levin, A. Ullrich, W. L. McGuire, Human breast cancer: correlation of relapse and survival with amplification of the HER-2/neu oncogene. Science 235, 177-182 (1987).
17. Y. Yarden, G. Pines, The ERBB network: at last, cancer therapy meets systems biology. Nat Rev Cancer 12, 553-563 (2012).
18. M. F. Rimawi, R. Schiff, C. K. Osborne, Targeting HER2 for the treatment of breast cancer. Annu Rev Med 66, 111-128 (2015).
19. A. Pandiella, H. Lehvaslaiho, M. Magni, K. Alitalo, J. Meldolesi, Activation of an EGFR/neu chimeric receptor: early intracellular signals and cell proliferation responses. Oncogene 4, 1299-1305 (1989).
20. K. S. Spencer, D. Graus-Porta, J. Leng, N. E. Hynes, R. L. Klemke, ErbB2 is necessary for induction of carcinoma cell invasion by ErbB family receptor tyrosine kinases. J Cell Biol 148, 385-397 (2000).
21. H. Korkaya, A. Paulson, F. Iovino, M. S. Wicha, HER2 regulates the mammary stem/progenitor cell population driving tumorigenesis and invasion. Oncogene 27, 6120-6130 (2008).
22. D. J. Slamon, B. Leyland-Jones, S. Shak, H. Fuchs, V. Paton, A. Bajamonde, T. Fleming, W. Eiermann, J. Wolter, M. Pegram, J. Baselga, L. Norton, Use of chemotherapy plus a monoclonal antibody against HER2 for metastatic breast cancer that overexpresses HER2. N Engl J Med 344, 783-792 (2001).
23. C. L. Vogel, M. A. Cobleigh, D. Tripathy, J. C. Gutheil, L. N. Harris, L. Fehrenbacher, D. J. Slamon, M. Murphy, W. F. Novotny, M. Burchmore, S. Shak, S. J. Stewart, M. Press, Efficacy and safety of trastuzumab as a single agent in first-line treatment of HER2-overexpressing metastatic breast cancer. J Clin Oncol 20, 719-726 (2002).
24. K. H. Lan, C. H. Lu, D. Yu, Mechanisms of trastuzumab resistance and their clinical implications. Ann N Y Acad Sci 1059, 70-75 (2005).
25. A. D. Seidman, D. Berry, C. Cirrincione, L. Harris, H. Muss, P. K. Marcom, G. Gipson, H. Burstein, D. Lake, C. L. Shapiro, P. Ungaro, L. Norton, E. Winer, C. Hudis, Randomized phase III trial of weekly compared with every-3-weeks paclitaxel for metastatic breast cancer, with trastuzumab for all HER-2 overexpressors and random assignment to trastuzumab or not in HER-2 non-overexpressors: final results of Cancer and Leukemia Group B protocol 9840. J Clin Oncol 26, 1642-1649 (2008).
26. N. L. Spector, K. L. Blackwell, Understanding the mechanisms behind trastuzumab therapy for human epidermal growth factor receptor 2-positive breast cancer. J Clin Oncol 27, 5838-5847 (2009).
27. J. Anido, M. Scaltriti, J. J. Bech Serra, B. Santiago Josefat, F. R. Todo, J. Baselga, J. Arribas, Biosynthesis of tumorigenic HER2 C-terminal fragments by alternative initiation of translation. EMBO J 25, 3234-3244 (2006).
28. P. Nagy, E. Friedlander, M. Tanner, A. I. Kapanen, K. L. Carraway, J. Isola, T. M. Jovin, Decreased accessibility and lack of activation of ErbB2 in JIMT-1, a herceptin-resistant, MUC4-expressing breast cancer cell line. Cancer Res 65, 473-482 (2005).
29. C. A. Ritter, M. Perez-Tones, C. Rinehart, M. Guix, T. Dugger, J. A. Engelman, C. L. Arteaga, Human breast cancer cells selected for resistance to trastuzumab in vivo overexpress epidermal growth factor receptor and ErbB ligands and remain dependent on the ErbB receptor network. Clin Cancer Res 13, 4909-4919 (2007).

30. M. J. Duffy, J. Crown, M. Mullooly, ADAM10 and ADAM17: New players in trastuzumab resistance. Oncotarget 5, 10963-10964 (2014).
31. A. B. Motoyama, N. E. Hynes, H. A. Lane, The efficacy of ErbB receptor-targeted anticancer therapeutics is influenced by the availability of epidermal growth factor-related peptides. Cancer Res 62, 3151-3158 (2002).
32. Y. Nagata, K. H. Lan, X. Zhou, M. Tan, F. J. Esteva, A. A. Sahin, K. S. Klos, P. Li, B. P. Monia, N. T. Nguyen, G. N. Hortobagyi, M. C. Hung, D. Yu, PTEN activation contributes to tumor inhibition by trastuzumab, and loss of PTEN predicts trastuzumab resistance in patients. Cancer Cell 6, 117-127 (2004).
33. Y. Lu, X. Zi, Y. Zhao, D. Mascarenhas, M. Pollak, Insulin-like growth factor-I receptor signaling and resistance to trastuzumab (Herceptin). J Natl Cancer Inst 93, 1852-1857 (2001).
34. J. Baselga, S. M. Swain, Novel anticancer targets: revisiting ERBB2 and discovering ERBB3. Nat Rev Cancer 9, 463-475 (2009).
35. H. J. Burstein, A. M. Storniolo, S. Franco, J. Forster, S. Stein, S. Rubin, V. M. Salazar, K. L. Blackwell, A phase II study of lapatinib monotherapy in chemotherapy-refractory HER2-positive and HER2-negative advanced or metastatic breast cancer. Ann Oncol 19, 1068-1074 (2008).
36. J. Baselga, J. Cortes, S. B. Kim, S. A. Im, R. Hegg, Y. H. Im, L. Roman, J. L. Pedrini, T. Pienkowski, A. Knott, E. Clark, M. C. Benyunes, G. Ross, S. M. Swain, C. S. Group, Pertuzumab plus trastuzumab plus docetaxel for metastatic breast cancer. N Engl J Med 366, 109-119 (2012).
37. N. Cancer Genome Atlas, Comprehensive molecular portraits of human breast tumours. Nature 490, 61-70 (2012).
38. C. Curtis, S. P. Shah, S. F. Chin, G. Turashvili, O. M. Rueda, M. J. Dunning, D. Speed, A. G. Lynch, S. Samarajiwa, Y. Yuan, S. Graf, G. Ha, G. Haffari, A. Bashashati, R. Russell, S. McKinney, M. Group, A. Langerod, A. Green, E. Provenzano, G. Wishart, S. Pinder, P. Watson, F. Markowetz, L. Murphy, I. Ellis, A. Purushotham, A. L. Borresen-Dale, J. D. Brenton, S. Tavare, C. Caldas, S. Aparicio, The genomic and transcriptomic architecture of 2,000 breast tumours reveals novel subgroups. Nature 486, 346-352 (2012).
39. M. Gijsen, P. King, T. Perera, P. J. Parker, A. L. Harris, B. Larijani, A. Kong, HER2 phosphorylation is maintained by a PKB negative feedback loop in response to anti-HER2 herceptin in breast cancer. PLoS Biol 8, e1000563 (2010).
40. E. A. Ebbing, J. P. Medema, H. Damhofer, S. L. Meijer, K. K. Krishnadath, M. I. van Berge Henegouwen, M. F. Bijlsma, H. W. van Laarhoven, ADAM10-mediated release of heregulin confers resistance to trastuzumab by activating HER3. Oncotarget 7, 10243-10254 (2016).
41. K. Feldinger, D. Generali, G. Kramer-Marek, M. Gijsen, T. B. Ng, J. H. Wong, C. Strina, M. Cappelletti, D. Andreis, J. L. Li, E. Bridges, H. Turley, R. Leek, I. Roxanis, J. Capala, G. Murphy, A. L. Harris, A. Kong, ADAM10 mediates trastuzumab resistance and is correlated with survival in HER2 positive breast cancer. Oncotarget 5, 6633-6646 (2014).
42. L. Tavares, E. Dimitrova, D. Oxley, J. Webster, R. Poot, J. Demmers, K. Berstarosti, S. Taylor, H. Ura, H. Koide, A. Wutz, M. Vidal, S. Elderkin, N. Brockdorff, RYBP-PRC1 complexes mediate H2A ubiquitylation at polycomb target sites independently of PRC2 and H3K27me3. Cell 148, 664-678 (2012).
43. J. Vandamme, P. Volkel, C. Rosnoblet, P. Le Faou, P. O. Angrand, Interaction proteomics analysis of polycomb proteins defines distinct PRC1 complexes in mammalian cells. Mol Cell Proteomics 10, M110 002642 (2011).
44. P. J. Lamy, F. Fina, C. Bascoul-Mollevi, A. C. Laberenne, P. M. Martin, L. Ouafik, W. Jacot, Quantification and clinical relevance of gene amplification at chromosome 17q12-q21 in human epidermal growth factor receptor 2-amplified breast cancers. Breast Cancer Res 13, R15 (2011).
45. M. S. Mano, D. D. Rosa, E. De Azambuja, G. F. Ismael, V. Durbecq, The 17q12-q21 amplicon: Her2 and topoisomerase-IIalpha and their importance to the biology of solid tumours. Cancer Treat Rev 33, 64-77 (2007).
46. R. Tamaskovic, M. Schwill, G. Nagy-Davidescu, C. Jost, D. C. Schaefer, W. P. Verdurmen, J. V. Schaefer, A. Honegger, A. Pluckthun, Intermolecular biparatopic trapping of ErbB2 prevents compensatory activation of PI3K/AKT via RAS-p010 crosstalk. Nat Commun 7, 11672 (2016).
47. J. L. Christenson, E. C. Denny, S. E. Kane, t-Darpp overexpression in HER2-positive breast cancer confers a survival advantage in lapatinib. Oncotarget 6, 33134-33145 (2015).
48. S. Hamel, A. Bouchard, C. Ferrario, S. Hassan, A. Aguilar-Mahecha, M. Buchanan, L. Quenneville, W. Miller, M. Basik, Both t-Darpp and DARPP-32 can cause resistance to trastuzumab in breast cancer cells and are frequently expressed in primary breast cancers. Breast Cancer Res Treat 120, 47-57 (2010).
49. J. Cui, K. Germer, T. Wu, J. Wang, J. Luo, S. C. Wang, Q. Wang, X. Zhang, Cross-talk between HER2 and MED1 regulates tamoxifen resistance of human breast cancer cells. Cancer Res 72, 5625-5634 (2012).
50. J. Malapeira, C. Esselens, J. J. Bech-Serra, F. Canals, J. Arribas, ADAM17 (TACE) regulates TGFbeta signaling through the cleavage of vasorin. Oncogene 30, 1912-1922 (2011).
51. M. Mullooly, P. M. McGowan, S. A. Kennedy, S. F. Madden, J. Crown, O. D. N, M. J. Duffy, ADAM10: a new player in breast cancer progression Br J Cancer 113, 945-951 (2015).
52. P. M. McGowan, B. M. Ryan, A. D. Hill, E. McDermott, N. O'Higgins, M. J. Duffy, ADAM-17 expression in breast cancer correlates with variables of tumor progression. Clin Cancer Res 13, 2335-2343 (2007).
53. G. Murphy, The ADAMs: signalling scissors in the tumor microenvironment. Nat Rev Cancer 8, 929-941 (2008).
54. X. Liu, J. S. Fridman, Q. Wang, E. Caulder, G. Yang, M. Covington, C. Liu, C. Marando, J. Zhuo, Y. Li, W. Yao, K. Vaddi, R. C. Newton, P. A. Scherle, S. M. Friedman, Selective inhibition of ADAM metalloproteases blocks HER-2 extracellular domain (ECD) cleavage and potentiates the anti-tumor effects of trastuzumab. Cancer Biol Ther 5, 648-656 (2006).
55. L. Witters, P. Scherle, S. Friedman, J. Fridman, E. Caulder, R. Newton, A. Lipton, Synergistic inhibition with a dual epidermal growth factor receptor/HER-2/neu tyrosine kinase inhibitor and a disintegrin and metalloprotease inhibitor. Cancer Res 68, 7083-7089 (2008).
56. T. A. Yap, L. Yan, A. Patnaik, I. Fearen, D. Olmos, K. Papadopoulos, R. D. Baird, L. Delgado, A. Taylor, L. Lupinacci, R. Riisnaes, L. L. Pope, S. P. Heaton, G.

Thomas, M. D. Garrett, D. M. Sullivan, J. S. de Bono, A. W. Tolcher, First-in-man clinical trial of the oral pan-AKT inhibitor MK-2206 in patients with advanced solid tumors. J Clin Oncol 29, 4688-4695 (2011).
57. M. Kanno, M. Hasegawa, A. Ishida, K. Isono, M. Taniguchi, mel-18, a Polycomb group-related mammalian gene, encodes a transcriptional negative regulator with tumor suppressive activity. EMBO J 14, 5672-5678 (1995).
58. R. Cao, Y. Tsukada, Y. Zhang, Role of Bmi-1 and Ring1A in H2A ubiquitylation and Hox gene silencing. Mol Cell 20, 845-854 (2005).
59. S. Elderkin, G. N. Maertens, M. Endoh, D. L. Mallery, N. Morrice, H. Koseki, G. Peters, N. Brockdorff, K. Hiom, A phosphorylated form of Mel-18 targets the Ring1B histone H2A ubiquitin ligase to chromatin. Mol Cell 28, 107-120 (2007).
60. M. H. Cho, J. H. Park, H. J. Choi, M. K. Park, H. Y. Won, Y. J. Park, C. H. Lee, S. H. Oh, Y. S. Song, H. S. Kim, Y. H. Oh, J. Y. Lee, G. Kong, DOT1L cooperates with the c-Myc-p300 complex to epigenetically derepress CDH1 transcription factors in breast cancer progression. Nat Commun 6, 7821 (2015).
61. W. Huang da, B. T. Sherman, R. A. Lempicki, Systematic and integrative analysis of large gene lists using DAVID bioinformatics resources. Nat Protoc 4, 44-57 (2009).
62. W. Huang da, B. T. Sherman, R. A. Lempicki, Bioinformatics enrichment tools: paths toward the comprehensive functional analysis of large gene lists. Nucleic Acids Res 37, 1-13 (2009).
63. V. K. Mootha, C. M. Lindgren, K. F. Eriksson, A. Subramanian, S. Sihag, J. Lehar, P. Puigserver, E. Carlsson, M. Ridderstrale, E. Laurila, N. Houstis, M. J. Daly, N. Patterson, J. P. Mesirov, T. R. Golub, P. Tamayo, B. Spiegelman, E. S. Lander, J. N. Hirschhorn, D. Altshuler, L. C. Groop, PGC-1alpha-responsive genes involved in oxidative phosphorylation are coordinately downregulated in human diabetes. Nat Genet 34, 267-273 (2003).
64. A. Subramanian, P. Tamayo, V. K. Mootha, S. Mukherjee, B. L. Ebert, M. A. Gillette, A. Paulovich, S. L. Pomeroy, T. R. Golub, E. S. Lander, J. P. Mesirov, Gene set enrichment analysis: a knowledge-based approach for interpreting genome-wide expression profiles. Proc Natl Acad Sci USA 102, 15545-15550 (2005).
65. E. Cerami, J. Gao, U. Dogrusoz, B. E. Gross, S. O. Sumer, B. A. Aksoy, A. Jacobsen, C. J. Byrne, M. L. Heuer, E. Larsson, Y. Antipin, B. Reva, A. P. Goldberg, C. Sander, N. Schultz, The cBio cancer genomics portal: an open platform for exploring multidimensional cancer genomics data. Cancer Discov 2, 401-404 (2012).
66. J. Gao, B. A. Aksoy, U. Dogrusoz, G. Dresdner, B. Gross, S. O. Sumer, Y. Sun, A. Jacobsen, R. Sinha, E. Larsson, E. Cerami, C. Sander, N. Schultz, Integrative analysis of complex cancer genomics and clinical profiles using the cBioPortal. Sci Signal 6, pl1 (2013).
67. Morey L, Santanach A, Blanco E, et al. Polycomb Regulates Mesoderm Cell Fate-Specification in Embryonic Stem Cells through Activation and Repression Mechanisms. Cell Stem Cell 2015; 17(3):300-15.
68. Castagnoli L, Iezzi M, Ghedini G C, et al. Activated d16HER2 homodimers and SRC kinase mediate optimal efficacy for trastuzumab. Cancer Res 2014; 74(21):6248-59.
69. Triulzi T, De Cecco L, Sandri M, et al. Whole-transcriptome analysis links trastuzumab sensitivity of breast tumors to both HER2 dependence and immune cell infiltration. Oncotarget 2015; 6(29):28173-82.

The invention claimed is:

1. A companion diagnostic and treatment method for HER2-targeted drugs in a subject with Human epidermal growth factor receptor 2 (HER2)-positive cancer comprising:

measuring a copy number of MEL-18 gene; an mRNA expression level of the MEL-18 gene; and/or an expression level of MEL-18 protein in a sample obtained from the subject with HER2-positive cancer; and if the copy number of the MEL-18 gene; the mRNA expression level of the MEL-18 gene; and/or the expression level of the MEL-18 protein measured in the sample are/is lower than predetermined value(s) predicting a response of the subject to HER2-targeted drugs as follows:

(a) administration of ADAM10 and/or ADAM17 inhibitor(s) is needed,
(b) possibility of manifesting drug resistance to HER2-targeted drugs is high,
(c) sensitivity to HER2-targeted drugs is low, and
(d) prognosis after treatment with HER2-targeted drugs is poor; and co-administering HER2-targeted drugs with ADAM10 and/or ADAM17 inhibitor(s) to the subject with HER2-positive cancer.

2. The method of claim 1, wherein the copy number of the MEL-18 gene; the mRNA expression level of the MEL-18 gene; or the expression level of the MEL-18 protein is measured by a method selected from the group consisting of fluorescent in situ hybridization (FISH), comparative genomic hybridization (CGH-based array), a single nucleotide polymorphism (SNP) array, sequence assembly comparison, paired-end sequencing, multiplex ligation dependent probe amplification (MLPA), multiplex amplifiable probe hybridization (MAPH), quantitative multiplex PCR of short fluorescent fragments (QMPSF), microsatellite genotyping, Southern blotting, immunohistochemistry (IHC), polymerase chain reaction (PCR), quantitative PCR (qPCR), quantitative real-time PCR (qRT-PCR), real-time PCR, and microarray-based comparative genomic hybridization and ligase chain reaction (LCR).

3. The method of claim 1, wherein the copy number of the MEL-18 gene and/or the mRNA expression level of the MEL-18 gene is measured by using an agent selected from the group consisting of a sense primer, an antisense primer, and a probe, which complementarily bind to the MEL-18 gene or mRNA thereof.

4. The method of claim 1, wherein the expression level of MEL-18 protein is measured by using an agent selected from the group consisting of an antibody, and an aptamer and a probe, which specifically bind to the MEL-18 protein.

5. The method of claim 1, wherein the HER2-targeted drugs are selected from the group consisting of trastuzumab, pertuzumab, and trastuzumab emtansine (T-DMI).

6. The method of claim 1, wherein the HER2-positive cancer are selected from the group consisting of breast cancer, gastric cancer, lung cancer, esophageal carcinoma, bladder cancer, and colon cancer.

7. A method of treating human epidermal growth factor receptor 2 (HER2)-positive cancer comprising:

measuring the copy number of the MEL-18 gene, the mRNA expression level of the MEL-18 gene, or the expression level of a protein encoded by the MEL-18 gene in a sample obtained from the subject with HER2-positive cancer; and administering a therapeutically effective amount of a pharmaceutical composition to the subject with HER2-positive cancer, wherein the pharmaceutical composition comprises one or more selected from the group consisting of MEL-18 gene, MEL-18 gene expression activators, MEL-18 proteins, and MEL-18 protein activators, and one or more selected from the group consisting of ADAM10 gene inhibitors, ADAM10 protein activity inhibitors, ADAM17 gene inhibitors, ADAM17 protein activity inhibitors, and ADAM10/ADAM17 dual inhibitors; and wherein the subject has the copy number of MEL-18 gene, the mRNA expression level of the MEL-18 gene, and/or the expression level of MEL-18 protein, which are/is lower than predetermined value(s); and the subject has or is expected to have drug resistance to HER2-targeted drugs.

8. The method of claim 7, further comprising:

co-administering HER2-targeted drugs to the subject receiving treatment with the pharmaceutical composition.

9. The method of claim 7, wherein the gene inhibitor is one or more selected from the group consisting of an antisense nucleotide, microRNA (miRNA), small interfering RNA (siRNA), short hairpin RNA (shRNA), and a compound and a protein, which complementarily bind to ADAM10, ADAM17, or ADAM10 and ADAM17 genes; and/or wherein the protein activity inhibitor is one or more selected from the group consisting of a compound, a peptide, a peptide mimetic, an aptamer, and an antibody, which specifically act on ADAM10, ADAM17, or ADAM10 and ADAM17 proteins.

10. The method of claim 7, wherein the ADAM10 or ADAM17 protein activity inhibitor is one or more selected from the group consisting of INCB3619, INCB7839, WAY-022, TMI-2, CGS 27023, GW280264, INCB8765, and GI254023.

11. The method of claim 7, wherein the HER2-positive cancer is selected from the group consisting of breast cancer, gastric cancer, lung cancer, esophageal carcinoma, bladder cancer, and colon cancer.

12. The method of claim 7, wherein the HER2-targeted drugs are selected from the group consisting of trastuzumab, pertuzumab, and trastuzumab emtansine (T-DMI).

13. A method for inhibiting or improving resistance of a subject with HER2-positive cancer with respect to HER2-targeted drugs comprising:

measuring a copy number of the MEL-18 gene, an mRNA expression level of the MEL-18 gene, or an expression level of a protein encoded by the MEL-18 gene in a sample obtained from the subject with HER2-positive cancer; and administering a therapeutically effective amount of a pharmaceutical composition to the subject with HER2-positive cancer, wherein the pharmaceutical composition comprises one or more selected from the group consisting of MEL-18 gene, MEL-18 gene expression activators, MEL-18 proteins, and MEL-18 protein activators, and one or more selected from the group consisting of ADAM10 gene inhibitors, ADAM10 protein activity inhibitors, ADAM17 gene inhibitors, ADAM17 protein activity inhibitors, and ADAM10/ADAM17 dual inhibitors, and wherein the subject has the copy number of MEL-18 gene, the mRNA expression level of the MEL-18 gene, and/or the expression level of MEL-18 protein, which are/is lower than predetermined value(s); and the subject has or is expected to have drug resistance to HER2-targeted drugs.

14. The method of claim 13, wherein the ADAM10 and/or ADAM17 protein activity inhibitor(s) are one or more selected from the group consisting of INCB3619, INCB7839, WAY-022, TMI-2, CGS 27023, GW280264, INCB8765, and GI254023.

15. The method of claim 13, wherein the pharmaceutical composition is co-administered with HER2-targeted drugs simultaneously or sequentially.

* * * * *